(12) United States Patent
Durrant et al.

(10) Patent No.: US 10,072,073 B2
(45) Date of Patent: Sep. 11, 2018

(54) GLYCANS AS FUNCTIONAL CANCER TARGETS AND ANTIBODIES THERETO

(71) Applicant: The University of Nottingham, Nottingham (GB)

(72) Inventors: Lindy Gillian Durrant, Nottingham (GB); Jiaxin Chua, Nottingham (GB); Tina Rose Parsons, Nottingham (GB)

(73) Assignee: The University of Nottingham, Nottingham (GB)

( * ) Notice: Subject to any disclaimer, the term of this patent is extended or adjusted under 35 U.S.C. 154(b) by 0 days.

(21) Appl. No.: 15/033,568

(22) PCT Filed: Oct. 31, 2014

(86) PCT No.: PCT/GB2014/053240
§ 371 (c)(1),
(2) Date: Apr. 29, 2016

(87) PCT Pub. No.: WO2015/063500
PCT Pub. Date: May 7, 2015

(65) Prior Publication Data
US 2016/0264652 A1 Sep. 15, 2016

(30) Foreign Application Priority Data

Nov. 1, 2013 (GB) .................................. 1319374.3

(51) Int. Cl.
| | |
|---|---|
| *C07K 16/18* | (2006.01) |
| *C07K 16/28* | (2006.01) |
| *C07K 16/30* | (2006.01) |
| *C07H 13/04* | (2006.01) |
| *G01N 33/574* | (2006.01) |
| *C07K 16/44* | (2006.01) |
| *A61K 39/00* | (2006.01) |

(52) U.S. Cl.
CPC .............. *C07K 16/18* (2013.01); *C07H 13/04* (2013.01); *C07K 16/2896* (2013.01); *C07K 16/30* (2013.01); *C07K 16/303* (2013.01); *C07K 16/3015* (2013.01); *C07K 16/3023* (2013.01); *C07K 16/3046* (2013.01); *C07K 16/3069* (2013.01); *C07K 16/44* (2013.01); *G01N 33/57492* (2013.01); *A61K 2039/505* (2013.01); *C07K 2317/21* (2013.01); *C07K 2317/24* (2013.01); *C07K 2317/52* (2013.01); *C07K 2317/56* (2013.01); *C07K 2317/565* (2013.01); *C07K 2317/567* (2013.01); *C07K 2317/73* (2013.01); *C07K 2317/732* (2013.01); *C07K 2317/734* (2013.01); *C07K 2317/77* (2013.01); *C07K 2317/92* (2013.01); *G01N 2400/50* (2013.01); *G01N 2440/38* (2013.01)

(58) Field of Classification Search
CPC ............ C07K 2317/24; C07K 2317/73; C07K 2317/56; C07K 2317/565
USPC .................................... 1/1; 424/133.1, 178.1
See application file for complete search history.

(56) References Cited

FOREIGN PATENT DOCUMENTS

WO    WO 2010/027364    3/2010

OTHER PUBLICATIONS

Chua et al., Clin Cancer Res; 21(13): 2963-74 (Published OnlineFirst Mar. 16, 2015)).*
Capurro et al., "Differential lytic and agglutinating activity of the anti-Lewis$^x$ monoclonal antibody FC-2.15 on human polymorphonuclear neutrophils and MCF-7 breast tumor cells. In vitro and ex vivo studies," *Cancer Immunol. Immunother.*, vol. 48, pp. 100-108, 1999.
Kitamura et al., "Specificity analysis of blood group Lewis-y (Le$^y$) antibodies generated against synthetic and natural Le$^y$ determinants," *Proc. Natl. Acad. Sci. USA*, vol. 91, pp. 12957-12961, 1994.
Rabu et al., "Glycans as targets for therapeutic antitumor antibodies," *Future Oncol.*, vol. 8, No. 8, pp. 943-960, 2012.
Sawada et al., "Human Monoclonal Antibodies to Sialyl-Lewis$^a$ (CA19.9) with Potent CDC, ADCC, and Antitumor Activity," *Clin. Cancer Res.*, vol. 17, No. 5, pp. 1024-1032, 2011.
Uetsuki et al., "Establishment and Characterization of Monoclonal Antibodies to Carbohydrate Antigens on Peanut Agglutinin Receptor Glycoprotein of Gastric Cancer KATO-III," *Hybridoma*, vol. 11, No, 4, pp. 425-435, 1992.

* cited by examiner

*Primary Examiner* — Lynn A Bristol
(74) *Attorney, Agent, or Firm* — Klarquist Sparkman, LLP

(57) ABSTRACT

A glycan having the structure galβ1-3GLcNacβ1-3Galβ1-4(Fucα1-3)GlcNAc (LecLe$^x$) which is attached to a lipid or protein backbone, and isolated binding members capable of binding thereto.

16 Claims, 39 Drawing Sheets
Specification includes a Sequence Listing.

Figure 1a: Amino acid and nucleotide sequence of FG88.2 IgG3 heavy chain

```
                                                                    ----------------- LEADER -----------------
                                              M   Y   L   G   L   N   Y   V   F   I   V   F   L   L   N   G   V   Q   S
                                       -19  atg tac ttg gga ctg aac tat gta ttc ata gtt ttt ctc tta aat ggt gtc cag agt <---------------------------- FR1 - IMGT ----------------------------->
        1    E   V   K   L   E   E   S   G   G       G   L   V   Q   P   G   G   S   M   K   L   S   C   A   A   S   G   F   T   F
  88_2H      gaa gtg aag ctt gag gag tct gga gga ... ggc ttg gtg caa cct gga gga tcc atg aaa ctc tct tgt gct gcc tct gga ttc act ttt ---- CDR1 - IMGT ........     <---------------------- FR2 - IMGT ----------------------->         ........ CDR2
        31                   S   D   A   W   M   N   W   V   R   Q   S   P   E   K   G   L   E   W   V   A   E   I   R   S   K   V
  88_2H      ... ... ... ... agt gac gcc tgg atg aac tgg gtc cgc cag tct cca gag aag ggg ctt gag tgg gtt gct gaa att aga agc aaa gtt

- IMGT ........     <---------------------------------------------------------------- FR3 - IMGT ----------------------
        61   I   N   P   A   I   Y   Y   A   E   S   V   K       E   R   F   T   I   L   R   D   D   S   K   S   S   V   Y   L   Q
  88_2H      att aat cct gca ata tac tat gct gag tct gtg aaa ... gag agg ttc acc ata tta aga gat gat tcc aaa agt agt gtc tac ctg caa ----------------------------------------->    ........ CDR3 - IMGT ........
        91   M   N   S   L   R   A   E   D   T   G   I   Y   Y   C   S   R   S   T   M   I   T   T   R   D   P   S   R   Y   F   D
  88_2H      atg aac agc tta aga gct gaa gac act gga att tat tac tgt tcc agg tct act atg att acg aca agg gac ccg tcc cgg tac ttc gat 121   V   W   G   A   G   T   T   V   T   V   S   S   A   T   T   T   A   P   S   V   Y   P   L   V   P   G   C   S   D   T
  88_2H      gtc tgg ggc gca ggg acc acg gtc acc gtc tcc tca gct aca aca aca gcc cca tct gtc tat ccc ttg gtc cct ggc tgc agt gac aca 151   S   G   S   S   V   T   L   G   C   L   V   K   G   Y   F   P   E   P   V   T   V   K   W   N   Y   G   A   L   S   S
  88_2H      tct gga tcc tcg gtg aca ctg gga tgc ctg gtc aaa ggc tac ttc cct gag ccg gta act gta aaa tgg aac tat gga gcc ctg tcc agc 181   G   V   R   T   V   S   S   V   L   Q   S   G   F   Y   S   L   S   S   L   V   T   V   P   S   S   T   W   P   S   Q
  88_2H      ggt gtg cgc aca gtc tca tct gtc ctg cag tct ggg ttc tat tcc ctc agc agc ttg gtg act gta ccc tcc agc acc tgg ccc agc cag 211   T   V   I   C   N   V   A   H   P   A   S   K   T   E   L   I   K   R   I   E   P   R   I   P   K   P   S   T   P   P
  88_2H      act gtc atc tgc aac gta gcc cac cca gcc agc aag act gag ttg atc aag aga atc gag cct aga ata ccc aag ccc agt acc ccc cca 241   G   S   S   C   P   P   G   N   I   L   G   G   P   S   V   F   I   F   P   P   K   P   K   D   A   L   M   I   S   L
  88_2H      ggt tct tca tgc cca cct ggt aac atc ttg ggt gga cca tcc gtc ttc atc ttc ccc cca aag ccc aag gat gca ctc atg atc tcc cta 271   T   P   K   V   T   C   V   V   V   D   V   S   E   D   D   P   D   V   H   V   S   W   F   V   D   N   K   E   V   H
  88_2H      acc ccc aag gtt acg tgt gtg gtg gtg gat gtg agc gag gat gac cca gat gtc cat gtc agc tgg ttt gtg gac aac aaa gaa gta cac 301   T   A   W   T   Q   P   R   E   A   Q   Y   N   S   T   F   R   V   V   S   A   L   P   I   Q   H   Q   D   W   M   R
  88_2H      aca gcc tgg aca cag ccc cgt gaa gct cag tac aac agt acc ttc cga gtg gtc agt gcc ctc ccc atc cag cac cag gac tgg atg agg 331   G   K   E   F   K   C   K   V   N   N   K   A   L   P   A   P   I   E   R   T   I   S   K   P   K   G   R   A   Q   T
  88_2H      ggc aag gag ttc aaa tgc aag gtc aac aac aaa gcc ctc cca gcc ccc atc gag aga acc atc tca aaa ccc aaa gga aga gcc cag aca 361   P   Q   V   Y   T   I   P   P   P   R   E   Q   M   S   K   K   K   V   S   L   T   C   L   V   T   N   F   F   S   E
  88_2H      cct caa gta tac acc ata ccc cca cct cgt gaa caa atg tcc aag aag aag gtt agt ctg acc tgc ctg gtc acc aac ttc ttc tct gaa 391   A   I   S   V   E   W   E   R   N   G   E   L   E   Q   D   Y   K   N   T   P   P   I   L   D   S   D   G   T   Y   F
  88_2H      gcc atc agt gtg gag tgg gaa agg aac gga gaa ctg gag cag gat tac aag aac act cca ccc atc ctg gac tca gat ggg acc tac ttc 421   L   Y   S   K   L   T   V   D   T   D   S   W   L   Q   G   E   I   F   T   C   S   V   V   H   E   A   L   H   N   H
  88_2H      ctc tac agc aag ctc act gtg gat aca gac agt tgg ttg caa gga gaa att ttt acc tgc tcc gtg gtg cat gag gct ctc cat aac cac 451   H   T   Q   K   N   L   S   R   S   P   G   K
  88_2H      cac aca cag aag aac ctg tct cgc tcc cct ggt aaa
```

Figure 1b: Amino acid and nucleotide sequence of FG88.2 mouse kappa light chain

```
                                                        _____ LEADER _____
                                        -20  M   S   V   L   T   Q   V   L   A   L   L   L   W   L   T   G   A   R   C
                                             atg agt gtg ctc act cag gtc ctg gcg ttg ctg ctg ctg tgg ctt aca ggt gcc aga tgt <---------------------------------------- FR1 - IMGT ---------------------------------------->
          1  D   I   Q   M   T   Q   S   P   T   S   L   S   A   S   V   G   E   T   V   T   I   T   C   R   T   S   E   N   I
88_2K     gac atc cag atg act cag tct cca acc tcc cta tct gca tct gtg gga gaa act gtc acc atc aca tgt cga aca agt gag aat att ...

.... CDR1 - IMGT ........              <--------------------- FR2 - IMGT --------------------->              CDR2
         31                           H   N   F   L   T   W   Y   Q   Q   K   Q   G   K   S   P   Q   V   L   V   Y   N   A
88_2K    ... ... ... ... ... ...    cac aat ttt tta aca tgg tat cag cag aaa cag gga aaa tct cct cag gtc ctg gtc tat aat gca ... ... ...

- IMGT              <------------------------------------------------------ FR3 - IMGT ------------------
         61                          K   T   L   P   D   G   V   P       S   R   F   S   G   S   G       S   G   T   Q   Y   S   L   K
88_2K    ... ... ... ... ... ...   aaa acc tta cca gat ggt gtc cca ... tca agg ttc agt ggc agt gga ... ... tca gga aca caa tat tct ctc aag ------------------------------------------------------>      ............... CDR3 - IMGT ...............
         91  I   N   S   L   Q   P   E   D   F   G   T   Y   Y   C   Q   H   F   W   S   S   P   W   T   F   G   G   G   T   K   L
88_2K    atc aac agc ctg cag cct gaa gat ttt ggg act tat tac tgt caa cat ttt tgg agt agt ccg tgg acg ttc ggt gga ggc acc aag ctg 121  E   I   K   R   A   D   A   A   P   T   V   S   I   F   P   P   S   S   E   Q   L   T   S   G   G   A   S   V   V   C
88_2K    gaa atc aaa cgg gct gat gct gca cca act gta tcc atc ttc cca cca tcc agt gag cag tta aca tct gga ggt gcc tca gtc gtg tgc 151  F   L   N   N   F   Y   P   K   D   I   N   V   K   W   K   I   D   G   S   E   R   Q   N   G   V   L   N   S   W   T
88_2K    ttc ttg aac aac ttc tac ccc aaa gac atc aat gtc aag tgg aag att gat ggc agt gaa cga caa aat ggc gtc ctg aac agt tgg act 181  D   Q   D   S   K   D   S   T   Y   S   M   S   S   T   L   T   L   T   K   D   E   Y   E   R   H   N   S   Y   T   C
88_2K    gat cag gac agc aaa gac agc acc tac agc atg agc agc acc ctc acg ttg acc aag gac gag tat gaa cga cat aac agc tat acc tgt 211  E   A   T   H   K   T   S   T   S   P   I   V   K   S   F   N   R   N   E   C
88_2K    gag gcc act cac aag aca tca act tca ccc att gtc aag agc ttc aac agg aat gag tgt
```

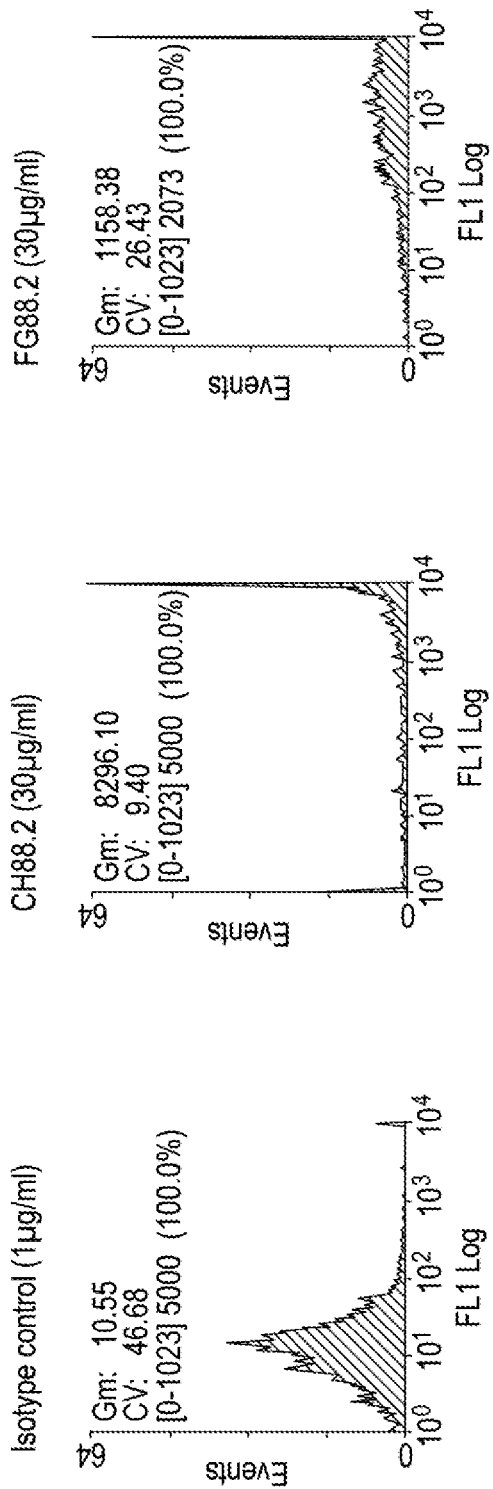
Fig 1c: Chimeric FG88.2 binds to the cell line C170 as assessed by flow cytometry Figure 1d: Amino acid and nucleotide sequence of FG88.2 human IgG1 heavy chain

```
                                                    _____ LEADER _____
                                                     M   Y   L   G   L   N   C   V   F   I   V   F   L   L   N   G   V   Q   S
                                                -19 atg tac ttg gga ctg aac tgt gta ttc ata gtt ttt ctc tta aat ggt gtc cag agt <----------------------------------- FR1 - IMGT -------------------------------------->
        1    E   V   K   L   E   E   S   G   G       G   L   V   Q   P   G   G   S   M   K   L   S   C   A   A   S   G   F   T   F
Ch88_2H     gaa gtg aaa ctc gag gag tct gga gga ... ggc ttg gtg caa cct gga gga tcc atg aaa ctc tct tgt gct gcc tct gga ttc act ttt ___ CDR1 - IMGT _____                <------------------- FR2 - IMGT -------------------->   _____ CDR2
        31                       S   D   A   W   M   N   W   V   R   Q   S   P   E   K   G   L   E   W   V   A   E   I   R   S   K   V
Ch88_2H     ... ... ... ... agt gac gcc tgg atg aac tgg gtc cgc cag tct cca gag aag ggg ctt gag tgg gtt gct gaa att aga agc aaa gtt

- IMGT _____        <------------------------------------------------------ FR3 - IMGT ------------------
        61   I   N   P   A   I   Y   Y   A   E   S   V   K       E   R   F   T   I   L   R   D   D   S   K   S   S   V   Y   L   Q
Ch88_2H     att aat cct gca ata tac tat gct gag tct gtg aaa ... gag agg ttc acc ata tta aga gat gat tcc aaa agt agt gtc tac ctg caa --------------------------------->          _____ CDR3 - IMGT _____
        91   M   N   S   L   R   A   E   D   T   G   I   Y   Y   C   S   R   S   T   M   I   T   T   R   D   P   S   R   Y   F   D
Ch88_2H     atg aac agc tta aga gct gaa gac act gga att tat tac tgt tcc agg tct act atg att acg aca agg gac ccg tcc cgg tac ttc gat 121   V   W   G   A   G   T   T   V   T   V   S   S   A   S   T   K   G   P   S   V   F   P   L   A   P   S   S   K   S   T
Ch88_2H     gtc tgg ggc gca ggg acc acg gtc acc gtc tcc agc gct tcc acc aag ggc cca tcg gtc ttc ccc ctg gca ccc tcc tcc aag agc acc 151   S   G   G   T   A   A   L   G   C   L   V   K   D   Y   F   P   E   P   V   T   V   S   W   N   S   G   A   L   T   S
Ch88_2H     tct ggg ggc aca gcg gcc ctg ggc tgc ctg gtc aag gac tac ttc ccc gaa ccg gtg acg gtg tcg tgg aac tca ggc gcc ctg acc agc 181   G   V   H   T   F   P   A   V   L   Q   S   S   G   L   Y   S   L   S   S   V   V   T   V   P   S   S   S   L   G   T
Ch88_2H     ggc gtg cac acc ttc ccg gct gtc cta cag tcc tca gga ctc tac tcc ctc agc agc gtg gtg acc gtg ccc tcc agc agc ttg ggc acc 211   Q   T   Y   I   C   N   V   N   H   K   P   S   N   T   K   V   D   K   K   V   E   P   K   S   C   D   K   T   H   T
Ch88_2H     cag acc tac atc tgc aac gtg aat cac aag ccc agc aac acc aag gtg gac aag aaa gtt gag ccc aaa tct tgt gac aaa act cac aca 241   C   P   P   C   P   A   P   E   L   L   G   G   P   S   V   F   L   F   P   P   K   P   K   D   T   L   M   I   S   R
Ch88_2H     tgc cca ccg tgc cca gca cct gaa ctc ctg ggg gga ccg tca gtc ttc ctc ttc ccc cca aaa ccc aag gac acc ctc atg atc tcc cgg 271   T   P   E   V   T   C   V   V   V   D   V   S   H   E   D   P   E   V   K   F   N   W   Y   V   D   G   V   E   V   H
Ch88_2H     acc cct gag gtc aca tgc gtg gtg gtg gac gtg agc cac gaa gac cct gag gtc aag ttc aac tgg tac gtg gac ggc gtg gag gtg cat 301   N   A   K   T   K   P   R   E   E   Q   Y   N   S   T   Y   R   V   V   S   V   L   T   V   L   H   Q   D   W   L   N
Ch88_2H     aat gcc aag aca aag ccg cgg gag gag cag tac aac agc acg tac cgt gtg gtc agc gtc ctc acc gtc ctg cac cag gac tgg ctg aat 331   G   K   E   Y   K   C   K   V   S   N   K   A   L   P   A   P   I   E   K   T   I   S   K   A   K   G   Q   P   R   E
Ch88_2H     ggc aag gag tac aag tgc aag gtc tcc aac aaa gcc ctc cca gcc ccc atc gag aaa acc atc tcc aaa gcc aaa ggg cag ccc cga gaa 361   P   Q   V   Y   T   L   P   P   S   R   D   E   L   T   K   N   Q   V   S   L   T   C   L   V   K   G   F   Y   P   S
Ch88_2H     cca cag gtg tac acc ctg ccc cca tcc cgg gat gag ctg acc aag aac cag gtc agc ctg acc tgc ctg gtc aaa ggc ttc tat ccc agc 391   D   I   A   V   E   W   E   S   N   G   Q   P   E   N   N   Y   K   T   T   P   P   V   L   D   S   D   G   S   F   F
Ch88_2H     gac atc gcc gtg gag tgg gag agc aat ggg cag ccg gag aac aac tac aag acc acg cct ccc gtg ctg gac tcc gac ggc tcc ttc ttc 421   L   Y   S   K   L   T   V   D   K   S   R   W   Q   Q   G   N   V   F   S   C   S   V   M   H   E   A   L   H   N   H
Ch88_2H     ctc tac agc aag ctc acc gtg gac aag agc agg tgg cag cag ggg aac gtc ttc tca tgc tcc gtg atg cat gag gct ctg cac aac cac 451   Y   T   Q   K   S   L   S   L   S   P   G   K
Ch88_2H     tac acg cag aag agc ctc tcc ctg tct ccg ggt aaa
```

Figure 1e: Amino acid and nucleotide sequence of FG88.2 human kappa light chain

```
                                                   _____ LEADER _____
                                         -20  N   S   V   L   T   Q   V   L   A   L   L   L   W   L   T   G   A   R   C
                                              atg agt gtg ctc act cag gtc ctg gcg ttg ctg ctg ctg tgg ctt aca ggt gcc aga tgt <----------------------------------- FR1 - IMGT ----------------------------------->
           1   D   I   Q   M   T   Q   S   P   T   S   L   S   A   S   V   G   E   T   V   T   I   T   C   R   T   S   E   N   I
    Ch88_2K    gac atc cag atg act cag tct cca acc tcc cta tct gca tct gtg gga gaa act gtc acc atc aca tgt cga aca agt gag aat att ...

.... CDR1 - IMGT ..........<-------------------------- FR2 - IMGT ---------------------------->............ CDR2
           31                          H   N   F   L   T   W   Y   Q   Q   K   Q   G   K   S   P   Q   V   L   V   Y   N   A
    Ch88_2K    ... ... ... ... ... cac aat ttt tta aca tgg tat cag cag aaa cag gga aaa tct cct cag gtc ctg gtc tat aat gca ... ... ...

- IMGT ..........|<----------------------------------------------------------------- FR3 - IMGT --------------------
           61                          K   T   L   P   D   G   V   P           S   R   F   S   G   S   G           S   G   T   Q   Y   S   L   K
    Ch88_2K    ... ... ... ... ... aaa acc tta cca gat ggt gtg cca ... tca agg ttc agt ggc agt gga ... ... tca gga aca caa tat tct ctc aag --------------------------------------->.............................. CDR3 - IMGT ..................
           91  I   N   S   L   Q   P   E   D   F   G   T   Y   Y   C   Q   R   F   W   S   S   P   W   T   F   G   G   G   T   K   L
    Ch88_2K    atc aac agc ctg cag cct gaa gat ttt ggg act tat tac tgt caa cat ttt tgg agt agt ccg tgg acg ttc ggt gga ggc acc aag ctg 121 E   I   K   R   T   V   A   P   S   V   F   I   F   P   P   S   D   E   Q   L   K   S   G   T   A   S   V   V   C   L
    Ch88_2K    gaa atc aaa cgt acg gta gcg cca tct gtc ttc atc ttc ccg cca tct gat gag cag ttg aaa tct gga act gcc tct gtt gtg tgc ctg L   N   N   F   Y   P   R   E   A   K   V   Q   W   K   V   D   N   A   L   Q   S   G   N   S   Q   E   S   V   T   E
    Ch88_2K    ctg aat aac ttc tat ccc aga gag gcc aaa gta cag tgg aag gtg gat aac gcc ctc caa tcg ggt aac tcc cag gag agt gtc aca gag Q   D   S   K   D   S   T   Y   S   L   S   S   T   L   T   L   S   K   A   D   Y   E   K   H   K   V   Y   A   C   E
    Ch88_2K    cag gac agc aag gac agc acc tac agc ctc agc agc acc ctg acg ctg agc aaa gca gac tac gag aaa cac aaa gtc tac gcc tgc gaa V   T   H   Q   G   L   S   S   P   V   T   K   S   F   N   R   G   E   C
    Ch88_2K    gtc acc cat cag ggc ctg agc tcg ccc gtc aca aag agc ttc aac agg gga gag tgt
```

Figure 2a: Amino acid and nucleotide sequence of FG88.7 IgG3 heavy chain

```
                                                  _____ LEADER _____
                                              M   Y   L   G   L   N   Y   V   F   I   V   F   L   L   N   G   V   Q   S
                                          -19 atg tac ttg gga ctg aac tat gta ttc ata gtt ttt ctc tta aat ggt gtc cag agt <---------------------------------- FR1 - IMGT ----------------------------------->
        1   E   V   K   L   E   E   S   G   G       G   L   V   Q   P   G   G   S   M   K   L   S   C   V   A   S   G   F   T   F
88_7H       gaa gtg aag ctt gag gag tct gga gga ... ggc ttg gtg caa cct gga gga tcc atg aaa ctc tct tgt gtt gcc tct gga ttc act ttt ____ CDR1 - IMGT _____              <--------------------- FR2 - IMGT --------------------->      _____ CDR2
       31                           S   D   A   W   M   N   W   V   R   Q   S   P   E   K   G   L   E   W   V   A   E   I   R   S   K   A
88_7H       ... ... ... ...         agt gac gcc tgg atg aac tgg gtc cgc cag tct cca gag aag ggg ctt gag tgg gtt gct gaa att aga agc aaa gct

- IMGT                  <---------------------------------------------------------- FR3 - IMGT -----------------
       61   I   N   P   A   I       Y   Y   A   E   S   V   K       G   R   F   T   I   L   R   D   D   S   K   S   S   V   Y   L   Q
88_7H       att aat cct gca ata     tac tat gct gag tct gtg aaa ... ggg agg ttc acc ata tta aga gat gat tcc aaa agt agt gtc tac ctg caa ---------------------------------->     _____                                               CDR3 - IMGT _____
       91   M   N   S   L   R   A   E   D   T   G   I   Y   Y   C   S   R   S   T   M   I   T   T   R   D   P   S   R   Y   F   D
88_7H       atg aac agc tta aga gct gaa gac act gga att tat tac tgt tcc agg tct act atg att acg aca agg gac ccg tcc cgg tac ttc gat _____
      121   V   W   G   A   G   T   T   V   T   V   S   S   A   T   T   T   A   P   S   V   Y   P   L   V   P   G   C   S   D   T
88_7H       gtc tgg ggc gca ggg acc acg gtc acc gtc tcc tca gct aca aca aca gcc cca tct gtc tat ccc ttg gtc cct ggc tgc agt gac aca 151   S   G   S   S   V   T   L   G   C   L   V   K   G   Y   F   P   E   P   V   T   V   K   W   N   Y   G   A   L   S   S
88_7H       tct gga tcc tcg gtg aca ctg gga tgc ctt gtc aaa ggc tac ttc cct gag ccg gta act gta aaa tgg aac tat gga gcc ctg tcc agc 181   G   V   R   T   V   S   S   V   L   Q   S   G   F   Y   S   L   S   S   L   V   T   V   P   S   S   T   W   P   S   Q
88_7H       ggt gtg cgc aca gtc tca tct gtc ctg cag tct ggg ttc tat tcc ctc agc agc ttg gtg act gta ccc tcc agc acc tgg ccc agc cag 211   T   V   I   C   N   V   A   H   P   A   S   K   T   E   L   I   K   R   I   E   P   R   I   P   K   P   S   T   P   P
88_7H       act gtc atc tgc aac gta gcc cac cca gcc agc aag act gag ttg atc aag aga atc gag cct aga atc ccc aag ccc agt acc ccc cca 241   G   S   S   C   P   P   G   N   I   L   G   G   P   S   V   F   I   F   P   P   K   P   K   D   A   L   M   I   S   L
88_7H       ggt tct tca tgc cca cct ggt aac atc ttg ggt gga cca tcc gtc ttc atc ttc ccc cca aag ccc aag gat gca ctc atg atc tcc cta 271   T   P   K   V   T   C   V   V   V   D   V   S   E   D   D   P   D   V   H   V   S   W   F   V   D   N   K   E   V   H
88_7H       acc ccc aag gtt acg tgt gtg gtg gtg gat gtg agc gag gat gac cca gat gtc cat gtc agc tgg ttt gtg gac aac aaa gaa gta cac 301   T   A   W   T   Q   P   R   E   A   Q   Y   N   S   T   F   R   V   V   S   A   L   P   I   Q   H   Q   D   W   M   R
88_7H       aca gcc tgg aca cag ccc cgt gaa gct cag tac aac agt acc ttc cga gtg gtc agt gcc ctc ccc atc cag cac cag gac tgg atg agg 331   G   K   E   F   K   C   K   V   N   N   K   A   L   P   A   P   I   E   R   T   I   S   K   P   K   G   R   A   Q   T
88_7H       ggc aag gag ttc aaa tgc aag gtc aac aac aaa gcc ctc cca gcc ccc atc gag aga acc atc tca aaa ccc aaa gga aga gcc cag aca 361   P   Q   V   Y   T   I   P   P   P   R   E   Q   M   S   K   K   K   V   S   L   T   C   L   V   T   N   F   F   S   E
88_7H       cct caa gta tac acc ata ccc cca cct cgt gaa caa atg tcc aag aag aag gtt agt ctg acc tgc ctg gtc acc aac ttc ttc tct gaa 391   A   I   S   V   E   W   E   R   N   G   E   L   E   Q   D   Y   K   N   T   P   P   I   L   D   S   D   G   T   Y   F
88_7H       gcc atc agt gtg gag tgg gaa agg aac gga gaa ctg gag cag gat tac aag aac act cca ccc atc ctg gac tca gat ggg acc tac ttc 421   L   Y   S   K   L   T   V   D   T   D   S   W   L   Q   G   E   I   F   T   C   S   V   V   H   E   A   L   H   N   H
88_7H       ctc tac agc aag ctc act gtg gat aca gac agt tgg ttg caa gga gaa att ttt acc tgc tcc gtg gtg cat gag gct ctc cat aac cac 451   H   T   Q   K   N   L   S   R   S   P   G   K
88_7H       cac aca cag aag aac ctg tct cgc tcc cct ggt aaa
```

Figure 2b: Amino acid and nucleotide sequence of FG88.7 kappa chain variable region

```
                                                  _____ LEADER _____
                                  -20  M   S   V   L   T   Q   V   L   A   L   L   L   L   W   L   T   G   A   R   C
                                       atg agt gtg ctc act cag gtc ctg gcg ttg ctg ctg ctg tgg ctt aca ggt gcc aga tgt <---------------------- FR1 - IMGT ---------------------->
            1   D   I   Q   M   T   Q   S   P   T   S   L   S   A   S   V   G   E   T   V   T   I   T   C   R   T   S   E   N   I
88_7K       gac atc cag atg act cag tct cca acc tcc cta tct gca tct gtg gga gaa act gtc acc atc aca tgt cga aca agt gag aat att ...

____ CDR1 - IMGT _____ <------------------- FR2 - IMGT ------------------>                      CDR2

31                              H   N   F   L   T   W   Y   Q   Q   K   Q   G   K   S   P   Q   V   L   V   Y   N   A
88_7K       ... ... ... ... ... cac aat ttt tta aca tgg tat cag cag aaa cag gga aaa tct cct cag gtc ctg gtc tat aat gca ... ... ...

- IMGT              <------------------------------------- FR3 - IMGT -------------------
            61                              K   T   L   P   D   G   V   P       S   R   F   S   G   S   G           S   E   T   Q   Y   S   L   K
88_7K       ... ... ... ... aaa acc tta cca gat ggt gtg cca ... tca agg ttc agt ggc agt gga ... ... tca gaa aca caa tat tct ctc aag

--------------------------------------------->   _____ CDR3 - IMGT _____

91  I   N   S   L   Q   P   E   D   F   G   T   Y   Y   C   Q   H   F   W   S   S   P   W   T   F   G   G   G   T   K   L
88_7K       atc aac agc ctg cag cct gaa gat ttt ggg act tat tac tgt caa cat ttt tgg agt agt ccg tgg acg ttc ggt gga ggc acc aag ctg 121 E   I   K   R   A   D   A   A   P   T   V   S   I   F   P   P   S   S   E   Q   L   T   S   G   G   A   S   V   V   C
88_7K       gaa atc aaa cgg gct gat gct gca cca act gta tcc atc ttc cca cca tcc agt gag cag tta aca tct gga ggt gcc tca gtc gtg tgc 151 F   L   N   N   F   Y   P   K   D   I   N   V   K   W   K   I   D   G   S   E   R   Q   N   G   V   L   N   S   W   T
88_7K       ttc ttg aac aac ttc tac ccc aaa gac atc aat gtc aag tgg aag att gat ggc agt gaa cga caa aat ggc gtc ctg aac agt tgg act 181 D   Q   D   S   K   D   S   T   Y   S   M   S   S   T   L   T   L   T   K   D   E   Y   E   R   H   N   S   Y   T   C
88_7K       gat cag gac agc aaa gac agc acc tac agc atg agc agc acc ctc acg ttg acc aag gac gag tat gaa cga cat aac agc tat acc tgt 211 E   A   T   H   K   T   S   T   S   P   I   V   K   S   F   N   R   N   E   C
88_7K       gag gcc act cac aag aca tca act tca ccc att gtc aag agc ttc aac agg aat gag tgt
```

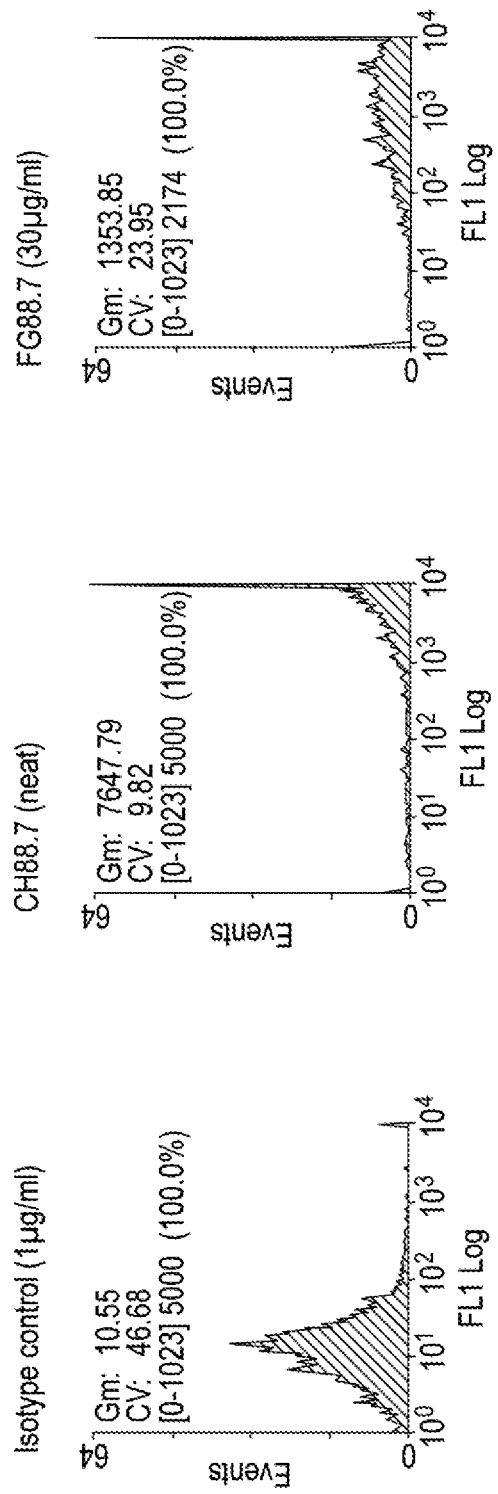
Fig 2c: Chimeric FG88.27 binds to the cell line C170 as assessed by flow cytometry Figure 2d: Amino acid and nucleotide sequence of FG88.7 human IgG1 heavy chain Figure 2e: Amino acid and nucleotide sequence of FG88.7 human kappa light chain

```
                                    ------------------------------ LEADER ------------------------------
                     -20  M   S   V   L   T   Q   V   L   A   L   L   L   W   L   T   G   A   R   C
                          atg agt gtg ctc act cag gtc ctg gcg ttg ctg ctg tgg ctt aca ggt gcc aga tgt <---------------------------------- FR1 - IMGT ---------------------------------->
             1    D   I   Q   M   T   Q   S   P   T   S   L   S   A   S   V   G   E   T   V   T   I   T   C   R   T   S   E   N   I
Ch88_2K         gac atc cag atg act cag tct cca acc tcc cta tct gca tct gtg gga gaa act gtc acc atc aca tgt cga aca agt gag aat att ...

.... CDR1 - IMGT ....       <---------------------------------- FR2 - IMGT ---------------------------------->                     CDR2
            31                            H   N   F   L   T   W   Y   Q   Q   K   G   K   S   P   Q   V   L   V   Y   N   A
Ch88_2K     ... ... ... ... ... ...       cac aat ttt tta aca tgg tat cag cag aaa cag gga aaa tct cct cag gtc ctg gtc tat aat gca ... ... ...

- IMGT                      <---------------------------------- FR3 - IMGT ----------------------------------
            61                            K   T   L   P   D   G   V   P       S   R   F   S   G   S   G       S   G   T   Q   Y   S   L   K
Ch88_2K     ... ... ... ... ... ...       aaa acc tta cca gat ggt gtg cca ... tca agg ttc agt ggc agt gga ... ... tca gga aca caa tat tct ctc aag ---------------------------------->   .................. CDR3 - IMGT .....................
            91    I   N   S   L   Q   P   E   D   F   G   T   Y   Y   C   Q   H   F   W   S   S   P   W   T   F   G   G   G   T   K   L
Ch88_2K         atc aac agc ctg cag cct gaa gat ttt ggg act tat tac tgt caa cat ttt tgg agt agt ccg tgg acg ttc ggt gga ggc acc aag ctg E   I   K   R   T   V   A   P   S   V   F   I   F   P   P   S   D   E   Q   L   K   S   G   T   A   S   V   V   C   L
Ch88_2K           gaa atc aaa cgt acg gta gcg cca tct gtc ttc atc ttc ccg cca tct gat gag cag ttg aaa tct gga act gcc tct gtt gtg tgc ctg L   N   N   F   Y   P   R   E   A   K   V   Q   W   K   V   D   N   A   L   Q   S   G   N   S   Q   E   S   V   T   E
Ch88_2K           ctg aat aac ttc tat ccc aga gag gcc aaa gta cag tgg aag gtg gat aac gcc ctc caa tcg ggt aac tcc cag gag agt gtc aca gag Q   D   S   K   D   S   T   Y   S   L   S   S   T   L   T   L   S   K   A   D   Y   E   K   H   K   V   Y   A   C   E
Ch88_2K           cag gac agc aag gac agc acc tac agc ctc agc agc acc ctg acg ctg agc aaa gca gac tac gag aaa cac aaa gtc tac gcc tgc gaa V   T   H   Q   G   L   S   S   P   V   T   K   S   F   N   R   G   E   C
Ch88_2K           gtc acc cat cag ggc ctg agc tcg ccc gtc aca aag agc ttc aac agg gga gag tgt
```

FG88.2 (supernatant 1/20 dilution)

Figure 4a (cont.)

| Glycan number | Glycan | Name | % of best binder | Structure |
|---|---|---|---|---|
| 126 | Galβ1-3(Fucα1-4)GlcNAcβ1-3Galβ1-4(Fucα1-3)GlcNAcβ-Sp0 | Le_aLe_x | 100 | 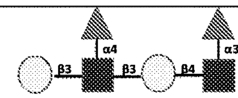 |
| 127 | Galβ1-3GlcNAcβ1-3Galβ1-4(Fucα1-3)GlcNAcβ-Sp0 | Lec-Le_x | 94 | 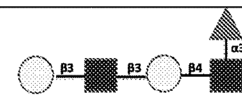 |
| 365 | Fucα1-4(Galβ1-3)GlcNAcβ1-2Manα1-6(Fucα1-4(Galβ1-3)GlcNAcβ1-2Manα1-3)Manβ1-4GlcNAcβ1-4(Fucα1-6)GlcNAcβ-Sp22 | Le_a containing glycan | 79 | 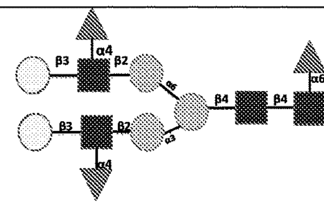 |
| 128 | Galβ1-3(Fucα1-4)GlcNAc-Sp0 | Le_a | 76 | 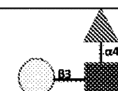 |
| 129 | Galβ1-3(Fucα1-4)GlcNAc-Sp8 | Le_a | 76 | 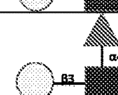 |
| 277 | Galβ1-3(Fucα1-4)GlcNAcβ1-3Galβ1-3(Fucα1-4)GlcNAcβ-Sp0 | Di-Le_a | 64 | 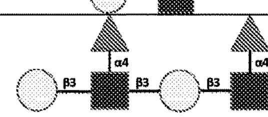 |
| 490 | Galβ1-3(Fucα1-4)GlcNAcβ1-6GalNAcα-Sp14 | Le_a containing glycan | 62 | 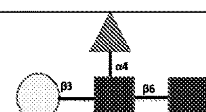 |
| 327 | Galb1-4(Fucα1-3)GlcNAcβ1-2Manα1-6(Galβ1-4(Fucα1-3)GlcNAcβ1-2Manα1-3)Manβ1-4GlcNAcβ1-4GlcNAcβ-Sp20 | Le_x containing glycan | 53 | 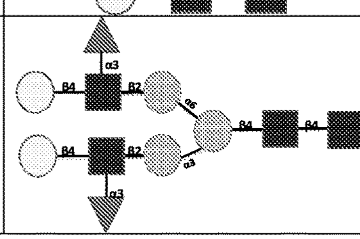 |

Figure 4b (cont.)

| Glycan number | Glycan | Name | Average RFU value | Structure |
|---|---|---|---|---|
| 277 | Galβ1-3(Fucα1-4)GlcNAcβ1-3Galβ1-3(Fucα1-4)GlcNAcβ-Sp0 | Di-Le<sub>a</sub> | 100 | 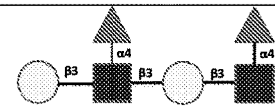 |
| 127 | Galβ1-3GlcNAcβ1-3Galβ1-4(Fucα1-3)GlcNAcβ-Sp0 | Lec-Le<sub>x</sub> | 84 | 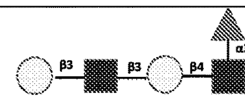 |
| 365 | Fucα1-4(Galβ1-3)GlcNAcβ1-2Manα1-6(Fucα1-4(Galβ1-3)GlcNAcβ1-2Manα1-3)Manβ1-4GlcNAcβ1-4(Fucα1-6)GlcNAcβ-Sp22 | Le<sub>a</sub> containing glycan | 66 | 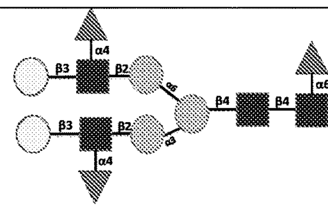 |
| 126 | Galβ1-3(Fucα1-4)GlcNAcβ1-3Galβ1-4(Fucα1-3)GlcNAcβ-Sp0 | Le<sub>a</sub>Le<sub>x</sub> | 52 | 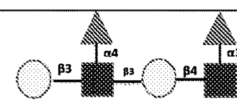 |
| 490 | Galβ1-3(Fucα1-4)GlcNAcβ1-6GalNAcα-Sp14 | Le<sub>a</sub> containing glycan | 49 | 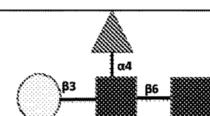 |
| 129 | Galβ1-3(Fucα1-4)GlcNAc-Sp8 | Le<sub>a</sub> | 49 | 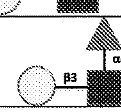 |
| 327 | Galβ1-4(Fucα1-3)GlcNAcβ1-2Manα1-6(Galβ1-4(Fucα1-3)GlcNAcβ1-2Manα1-3)Manβ1-4GlcNAcβ1-4GlcNAcβ-Sp20 | Le<sub>x</sub> containing glycan | 47 | 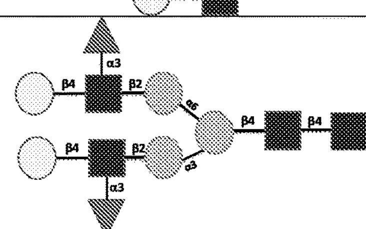 |
| 128 | Galβ1-3(Fucα1-4)GlcNAc-Sp0 | Le<sub>a</sub> | 36 | 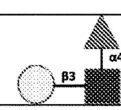 |

Figure 9c
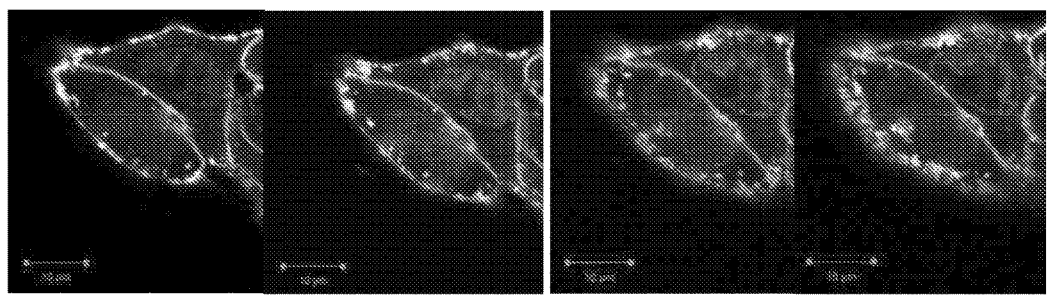
Figure 9d
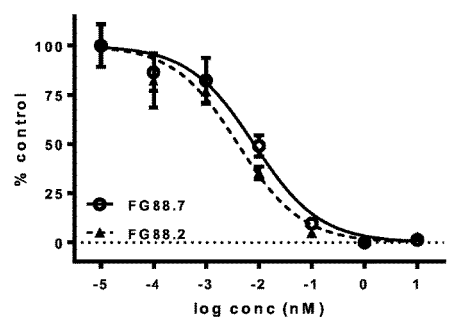
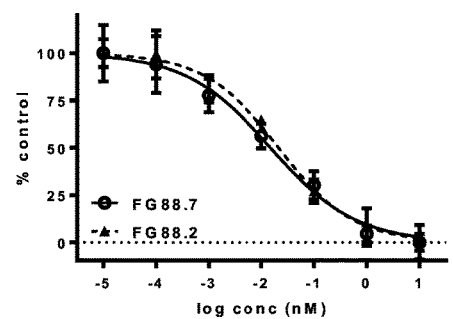
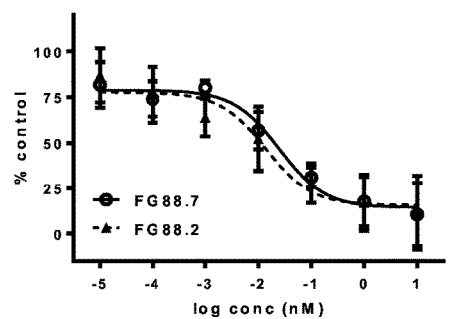
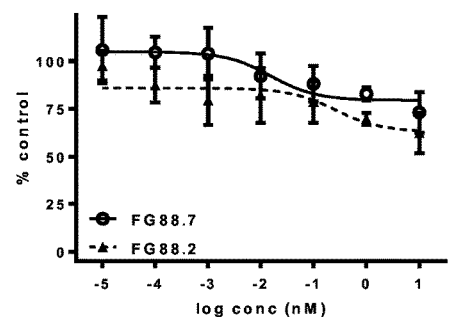

SEQUENCE LISTING

<160> NUMBER OF SEQ ID NOS: 18

<210> SEQ ID NO 1
<211> LENGTH: 475
<212> TYPE: PRT
<213> ORGANISM: Mus musculus

<400> SEQUENCE: 1

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asn Trp Val Arg Gln Ser Pro Glu Lys Gly Leu
    50                  55                  60

Glu Trp Val Ala Glu Ile Arg Ser Lys Val Ile Asn Pro Ala Ile Tyr
65                  70                  75                  80

Tyr Ala Glu Ser Val Lys Glu Arg Phe Thr Ile Leu Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Ser Arg Ser Thr Met Ile Thr Thr Arg Asp Pro
        115                 120                 125

Ser Arg Tyr Phe Asp Val Trp Gly Ala Gly Thr Thr Val Thr Val Ser
    130                 135                 140

Ser Ala Thr Thr Ala Pro Ser Val Tyr Pro Leu Val Pro Gly Cys
145                 150                 155                 160

Ser Asp Thr Ser Gly Ser Ser Val Thr Leu Gly Cys Leu Val Lys Gly
                165                 170                 175

Tyr Phe Pro Glu Pro Val Thr Val Lys Trp Asn Tyr Gly Ala Leu Ser
            180                 185                 190

Ser Gly Val Arg Thr Val Ser Ser Val Leu Gln Ser Gly Phe Tyr Ser
        195                 200                 205

Leu Ser Ser Leu Val Thr Val Pro Ser Ser Thr Trp Pro Ser Gln Thr
    210                 215                 220

Val Ile Cys Asn Val Ala His Pro Ala Ser Lys Thr Glu Leu Ile Lys
225                 230                 235                 240

Arg Ile Glu Pro Arg Ile Pro Lys Pro Ser Thr Pro Pro Gly Ser Ser
            245                 250                 255

Cys Pro Pro Gly Asn Ile Leu Gly Gly Pro Ser Val Phe Ile Phe Pro
        260                 265                 270

Pro Lys Pro Lys Asp Ala Leu Met Ile Ser Leu Thr Pro Lys Val Thr
    275                 280                 285

Cys Val Val Val Asp Val Ser Glu Asp Asp Pro Asp Val His Val Ser
290                 295                 300

Trp Phe Val Asp Asn Lys Glu Val His Thr Ala Trp Thr Gln Pro Arg
305                 310                 315                 320

Glu Ala Gln Tyr Asn Ser Thr Phe Arg Val Val Ser Ala Leu Pro Ile
                325                 330                 335

Gln His Gln Asp Trp Met Arg Gly Lys Glu Phe Lys Cys Lys Val Asn
            340                 345                 350

Asn Lys Ala Leu Pro Ala Pro Ile Glu Arg Thr Ile Ser Lys Pro Lys
        355                 360                 365

Gly Arg Ala Gln Thr Pro Gln Val Tyr Thr Ile Pro Pro Pro Arg Glu
    370                 375                 380

Gln Met Ser Lys Lys Lys Val Ser Leu Thr Cys Leu Val Thr Asn Phe
385                 390                 395                 400

Phe Ser Glu Ala Ile Ser Val Glu Trp Glu Arg Asn Gly Glu Leu Glu
                405                 410                 415

Gln Asp Tyr Lys Asn Thr Pro Pro Ile Leu Asp Ser Asp Gly Thr Tyr
            420                 425                 430

Phe Leu Tyr Ser Lys Leu Thr Val Asp Thr Asp Ser Trp Leu Gln Gly
        435                 440                 445

Glu Ile Phe Thr Cys Ser Val Val His Glu Ala Leu His Asn His His
    450                 455                 460

Thr Gln Lys Asn Leu Ser Arg Ser Pro Gly Lys
465                 470                 475

<210> SEQ ID NO 2
<211> LENGTH: 1425
<212> TYPE: DNA
<213> ORGANISM: Mus musculus

<400> SEQUENCE: 2
atgtacttgg gactgaacta tgtattcata gttttctctc taaatggtgt ccagagtgaa      60
gtgaagcttg aggagtctgg aggaggcttg gtgcaacctg aggatccatg aaactctct     120 tgtgctgcct ctggattcac ttttagtgac gcctggatga actgggtccg ccagtctcca     180
gagaaggggc ttgagtgggt tgctgaaatt agaagcaaag ttattaatcc tgcaatatac     240
tatgctgagt ctgtgaaaga gaggttcacc atattaagag atgattccaa agtagtgtc     300 tacctgcaaa tgaacagctt aagagctgaa gacactggaa tttattactg ttccaggtct     360
actatgatta cgacaaggga cccgtcccgg tacttcgatg tctggggcgc agggaccacg     420
gtcaccgtct cctcagctac aacaacagcc ccatctgtct atcccttggt ccctggctgc     480
agtgacacat ctggatcctc ggtgacactg gatgccttg tcaaaggcta cttccctgag     540
ccggtaactg taaaatggaa ctatggagcc ctgtccagcg gtgtgcgcac agtctcatct     600
gtcctgcagt ctgggttcta ttccctcagc agcttggtga ctgtaccctc agcacctgg     660 cccagccaga ctgtcatctg caacgtagcc acccagcca gcaagactga gttgatcaag     720
agaatcgagc ctagaatacc caagcccagt acccccccag gttcttcatg cccacctggt     780

| | |
|---|---|
| aacatcttgg gtggaccatc cgtcttcatc ttcccccccaa agcccaagga tgcactcatg | 840 |
| atctccctaa cccccaaggt tacgtgtgtg gtggtggatg tgagcgagga tgacccagat | 900 |
| gtccatgtca gctggtttgt ggacaacaaa gaagtacaca cagcctggac acagccccgt | 960 |
| gaagctcagt acaacagtac cttccgagtg gtcagtgccc tccccatcca gcaccaggac | 1020 |
| tggatgaggg gcaaggagtt caaatgcaag gtcaacaaca aagccctccc agcccccatc | 1080 |
| gagagaacca tctcaaaacc caaggaaga gcccagacac ctcaagtata caccataccc | 1140 |
| ccacctcgtg aacaaatgtc caagaagaag gttagtctga cctgcctggt caccaacttc | 1200 |
| ttctctgaag ccatcagtgt ggagtgggaa aggaacggag aactggagca ggattacaag | 1260 |
| aacactccac ccatcctgga ctcagatggg acctacttcc tctacagcaa gctcactgtg | 1320 |
| gatacagaca gttggttgca aggagaaatt tttacctgct ccgtggtgca tgaggctctc | 1380 |
| cataaccacc acacacagaa gaacctgtct cgctcccctg gtaaa | 1425 |

<210> SEQ ID NO 3
<211> LENGTH: 234
<212> TYPE: PRT
<213> ORGANISM: Mus musculus

<400> SEQUENCE: 3

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Thr Ser Leu Ser
            20                  25                  30

Ala Ser Val Gly Glu Thr Val Thr Ile Thr Cys Arg Thr Ser Glu Asn
        35                  40                  45

Ile His Asn Phe Leu Thr Trp Tyr Gln Gln Lys Gln Gly Lys Ser Pro
    50                  55                  60

Gln Val Leu Val Tyr Asn Ala Lys Thr Leu Pro Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Ser Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Thr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 4
<211> LENGTH: 702
<212> TYPE: DNA

<213> ORGANISM: Mus musculus

<400> SEQUENCE: 4

```
atgagtgtgc tcactcaggt cctggcgttg ctgctgctgt ggcttacagg tgccagatgt      60
gacatccaga tgactcagtc tccaacctcc ctatctgcat ctgtgggaga aactgtcacc     120
atcacatgtc gaacaagtga gaatattcac aattttttaa catggtatca gcagaaacag     180
ggaaaatctc ctcaggtcct ggtctataat gcaaaaacct accagatggt gtgccatca     240
aggttcagtg gcagtggatc aggaacacaa tattctctca gatcaacag cctgcagcct     300
gaagattttg ggacttatta ctgtcaacat tttggagta gtccgtggac gttcggtgga     360
ggcaccaagc tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag cacccctcacg    600
ttgaccaagg acgagtatga cgacataac agctatacct gtgaggccac tcacaagaca     660
tcaacttcac ccattgtcaa gagcttcaac aggaatgagt gt                        702
```

<210> SEQ ID NO 5
<211> LENGTH: 475
<212> TYPE: PRT
<213> ORGANISM: Homo sapiens

<400> SEQUENCE: 5

```
Met Tyr Leu Gly Leu Asn Cys Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asn Trp Val Arg Gln Ser Pro Glu Lys Gly Leu
    50                  55                  60

Glu Trp Val Ala Glu Ile Arg Ser Lys Val Ile Asn Pro Ala Ile Tyr
65                  70                  75                  80

Tyr Ala Glu Ser Val Lys Glu Arg Phe Thr Ile Leu Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Ser Arg Ser Thr Met Ile Thr Thr Arg Asp Pro
        115                 120                 125

Ser Arg Tyr Phe Asp Val Trp Gly Ala Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
```

```
                225                 230                 235                 240
Lys Lys Val Glu Pro Lys Ser Cys Asp Lys Thr His Thr Cys Pro Pro
                245                 250                 255
Cys Pro Ala Pro Glu Leu Leu Gly Gly Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Gly Lys
465                 470                 475

<210> SEQ ID NO 6
<211> LENGTH: 1425
<212> TYPE: DNA
<213> ORGANISM: Homo sapiens

<400> SEQUENCE: 6
atgtacttgg gactgaactg tgtattcata gttttctctc taaatggtgt ccagagtgaa      60
gtgaaactcg aggagtctgg aggaggcttg gtgcaacctg gaggatccat gaaactctct     120
tgtgctgcct ctggattcac ttttagtgac gcctggatga actgggtccg ccagtctcca     180
gagaagggc ttgagtgggt tgctgaaatt agaagcaaag ttattaatcc tgcaatatac     240
tatgctgagt ctgtgaaaga gaggttcacc atattaagag atgattccaa agtagtgtc      300
tacctgcaaa tgaacagctt aagagctgaa gacactggaa tttattactg ttccaggtct     360
actatgatta cgacaaggga cccgtccgg tacttcgatg tctggggcgc agggaccacg      420
gtcaccgtct ccagcgcttc caccaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
```

```
aagaaagttg agcccaaatc ttgtgacaaa actcacacat gcccaccgtg cccagcacct    780
gaactcctgg ggggaccgtc agtcttcctc ttccccccaa acccaagga cacccctcatg    840 atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag ccccgagaac acaggtgta caccctgccc   1140 ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaa               1425
```

<210> SEQ ID NO 7
<211> LENGTH: 233
<212> TYPE: PRT
<213> ORGANISM: Homo sapiens

<400> SEQUENCE: 7

```
Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Thr Ser Leu Ser
            20                  25                  30

Ala Ser Val Gly Glu Thr Val Thr Ile Thr Cys Arg Thr Ser Glu Asn
        35                  40                  45

Ile His Asn Phe Leu Thr Trp Tyr Gln Gln Lys Gln Gly Lys Ser Pro
    50                  55                  60

Gln Val Leu Val Tyr Asn Ala Lys Thr Leu Pro Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Ser Pro Trp Thr Phe Gly Gly Gly Thr Lys Leu Glu Ile Lys Arg
        115                 120                 125

Thr Val Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 8

```
<211> LENGTH: 699
<212> TYPE: DNA
<213> ORGANISM: Homo sapiens

<400> SEQUENCE: 8
atgagtgtgc tcactcaggt cctggcgttg ctgctgctgt ggcttacagg tgccagatgt      60
gacatccaga tgactcagtc tccaacctcc ctatctgcat ctgtgggaga aactgtcacc     120
atcacatgtc gaacaagtga gaatattcac aattttttaa catggtatca gcagaaacag     180
ggaaaatctc ctcaggtcct ggtctataat gcaaaaacct accagatggg tgtgccatca     240
aggttcagtg gcagtggatc aggaacacaa tattctctca gatcaacag cctgcagcct     300 gaagattttg ggacttatta ctgtcaacat ttttggagta gtccgtggac gttcggtgga     360
ggcaccaagc tggaaatcaa acgtacggta gcgccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgt                           699

<210> SEQ ID NO 9
<211> LENGTH: 475
<212> TYPE: PRT
<213> ORGANISM: Homo sapiens

<400> SEQUENCE: 9

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asp Ala Trp Met Asn Trp Val Arg Gln Ser Pro Glu Lys Gly Leu
    50                  55                  60

Glu Trp Val Ala Glu Ile Arg Ser Lys Ala Ile Asn Pro Ala Ile Tyr
65                  70                  75                  80

Tyr Ala Glu Ser Val Lys Gly Arg Phe Thr Ile Leu Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Ser Arg Ser Thr Met Ile Thr Thr Arg Asp Pro
        115                 120                 125

Ser Arg Tyr Phe Asp Val Trp Gly Ala Gly Thr Thr Val Thr Val Ser
    130                 135                 140

Ser Ala Thr Thr Ala Pro Ser Val Tyr Pro Leu Val Pro Gly Cys
145                 150                 155                 160

Ser Asp Thr Ser Gly Ser Ser Val Thr Leu Gly Cys Leu Val Lys Gly
                165                 170                 175

Tyr Phe Pro Glu Pro Val Thr Val Lys Trp Asn Tyr Gly Ala Leu Ser
            180                 185                 190

Ser Gly Val Arg Thr Val Ser Ser Val Leu Gln Ser Gly Phe Tyr Ser
        195                 200                 205

Leu Ser Ser Leu Val Thr Val Pro Ser Ser Thr Trp Pro Ser Gln Thr
    210                 215                 220
```

```
Val Ile Cys Asn Val Ala His Pro Ala Ser Lys Thr Glu Leu Ile Lys
225                 230                 235                 240

Arg Ile Glu Pro Arg Ile Pro Lys Pro Ser Thr Pro Gly Ser Ser
            245                 250                 255

Cys Pro Pro Gly Asn Ile Leu Gly Gly Pro Ser Val Phe Ile Phe Pro
            260                 265                 270

Pro Lys Pro Lys Asp Ala Leu Met Ile Ser Leu Thr Pro Lys Val Thr
        275                 280                 285

Cys Val Val Val Asp Val Ser Glu Asp Asp Pro Asp Val His Val Ser
    290                 295                 300

Trp Phe Val Asp Asn Lys Glu Val His Thr Ala Trp Thr Gln Pro Arg
305                 310                 315                 320

Glu Ala Gln Tyr Asn Ser Thr Phe Arg Val Val Ser Ala Leu Pro Ile
                325                 330                 335

Gln His Gln Asp Trp Met Arg Gly Lys Glu Phe Lys Cys Lys Val Asn
            340                 345                 350

Asn Lys Ala Leu Pro Ala Pro Ile Glu Arg Thr Ile Ser Lys Pro Lys
        355                 360                 365

Gly Arg Ala Gln Thr Pro Gln Val Tyr Thr Ile Pro Pro Pro Arg Glu
    370                 375                 380

Gln Met Ser Lys Lys Lys Val Ser Leu Thr Cys Leu Val Thr Asn Phe
385                 390                 395                 400

Phe Ser Glu Ala Ile Ser Val Glu Trp Glu Arg Asn Gly Glu Leu Glu
                405                 410                 415

Gln Asp Tyr Lys Asn Thr Pro Pro Ile Leu Asp Ser Asp Gly Thr Tyr
            420                 425                 430

Phe Leu Tyr Ser Lys Leu Thr Val Asp Thr Asp Ser Trp Leu Gln Gly
        435                 440                 445

Glu Ile Phe Thr Cys Ser Val Val His Glu Ala Leu His Asn His His
    450                 455                 460

Thr Gln Lys Asn Leu Ser Arg Ser Pro Gly Lys
465                 470                 475

<210> SEQ ID NO 10
<211> LENGTH: 1425
<212> TYPE: DNA
<213> ORGANISM: Homo sapiens

<400> SEQUENCE: 10
atgtacttgg gactgaacta tgtattcata gttttctct taaatggtgt ccagagtgaa      60
gtgaagcttg aggagtctgg aggaggcttg gtgcaacctg gaggatccat gaaactctct    120
tgtgttgcct ctggattcac ttttagtgac gcctggatga actgggtccg ccagtctcca    180
gagaaggggc ttgagtgggt tgctgaaatt agaagcaaag ctattaatcc tgcaatatac    240
tatgctgagt ctgtgaaagg gaggttcacc atattaagag atgattccaa agtagtgtc    300 tacctgcaaa tgaacagctt aagagctgaa gacactggaa tttattactg ttccaggtct    360
actatgatta cgacaaggga cccgtcccgg tacttcgatg tctggggcgc agggaccacg    420
gtcaccgtct cctcagctac aacaacagcc catctgtct atcccttggt ccctggctgc    480
agtgacacat ctggatcctc ggtgacactg gatgccttg tcaaaggcta cttccctgag    540
ccggtaactg taaatggaa ctatggagcc ctgtccagcg gtgtgcgcac agtctcatct    600
gtcctgcagt ctgggttcta ttccctcagc agcttggtga ctgtaccctc agcacctgg    660
```

-continued

```
cccagccaga ctgtcatctg caacgtagcc cacccagcca gcaagactga gttgatcaag    720
agaatcgagc ctagaatacc caagcccagt acccccccag gttcttcatg cccacctggt    780
aacatcttgg gtggaccatc cgtcttcatc ttccccccaa agcccaagga tgcactcatg    840
atctccctaa ccccccaaggt tacgtgtgtg gtggtggatg tgagcgagga tgacccagat    900
gtccatgtca gctggtttgt ggacaacaaa gaagtacaca cagcctggac acagccccgt    960
gaagctcagt acaacagtac cttccgagtg gtcagtgccc tccccatcca gcaccaggac    1020
tggatgaggg gcaaggagtt caaatgcaag gtcaacaaca aagccctccc agcccccatc    1080
gagagaacca tctcaaaacc caaggaaga gcccagacac tcaagtata caccataccc    1140 ccacctcgtg aacaaatgtc caagaagaag gttagtctga cctgcctggt caccaacttc    1200
ttctctgaag ccatcagtgt ggagtgggaa aggaacggag aactggagca ggattacaag    1260
aacactccac ccatcctgga ctcagatggg acctacttcc tctacagcaa gctcactgtg    1320
gatacagaca gttggttgca aggagaaatt tttacctgct ccgtggtgca tgaggctctc    1380
cataaccacc acacacagaa gaacctgtct cgctcccctg gtaaa               1425
```

<210> SEQ ID NO 11
<211> LENGTH: 234
<212> TYPE: PRT
<213> ORGANISM: Homo sapiens

<400> SEQUENCE: 11

```
Met Ser Val Leu Thr Gln Val Leu Ala Leu Leu Leu Trp Leu Thr
1               5                   10                  15

Gly Ala Arg Cys Asp Ile Gln Met Thr Gln Ser Pro Thr Ser Leu Ser
            20                  25                  30

Ala Ser Val Gly Glu Thr Val Thr Ile Thr Cys Arg Thr Ser Glu Asn
        35                  40                  45

Ile His Asn Phe Leu Thr Trp Tyr Gln Gln Lys Gln Gly Lys Ser Pro
    50                  55                  60

Gln Val Leu Val Tyr Asn Ala Lys Thr Leu Pro Asp Gly Val Pro Ser
65                  70                  75                  80

Arg Phe Ser Gly Ser Gly Ser Glu Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Ser Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 12
<211> LENGTH: 702
<212> TYPE: DNA
<213> ORGANISM: Homo sapiens

<400> SEQUENCE: 12

```
atgagtgtgc tcactcaggt cctggcgttg ctgctgctgt ggcttacagg tgccagatgt      60
gacatccaga tgactcagtc tccaacctcc ctatctgcat ctgtgggaga aactgtcacc     120
atcacatgtc gaacaagtga gattattcac aattttttaa catggtatca gcagaaacag     180
ggaaaatctc ctcaggtcct ggtctataat gcaaaaacct taccagatgg tgtgccatca     240
aggttcagtg gcagtggatc agaaacacaa tattctctca gatcaacag cctgcagcct      300
gaagattttg ggacttatta ctgtcaacat tttggagta gtccgtggac gttcggtgga      360
ggcaccaagc tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga cgacataac agctatacct gtgaggccac tcacaagaca      660
tcaacttcac ccattgtcaa gagcttcaac aggaatgagt gt                         702
```

<210> SEQ ID NO 13
<211> LENGTH: 486
<212> TYPE: PRT
<213> ORGANISM: Homo sapiens

<400> SEQUENCE: 13

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asn Trp Val Arg Gln Ser Pro Glu Lys Gly Leu Glu Trp Val
        35                  40                  45

Ala Glu Ile Arg Ser Lys Ala Ile Asn Pro Ala Ile Tyr Tyr Ala Glu
    50                  55                  60

Ser Val Lys Gly Arg Phe Thr Ile Leu Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Ser Arg Ser Thr Met Ile Thr Thr Arg Asp Pro Ser Arg Tyr
            100                 105                 110

Phe Asp Val Trp Gly Ala Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Val Trp Gly Ala Gly Thr Thr Val Thr Val Ser Ser Ala Ser Thr Lys
145                 150                 155                 160

Gly Pro Ser Val Phe Pro Leu Ala Pro Ser Ser Lys Ser Thr Ser Gly
                165                 170                 175

Gly Thr Ala Ala Leu Gly Cys Leu Val Lys Asp Tyr Phe Pro Glu Pro
            180                 185                 190

Val Thr Val Ser Trp Asn Ser Gly Ala Leu Thr Ser Gly Val His Thr
        195                 200                 205

```
Phe Pro Ala Val Leu Gln Ser Ser Gly Leu Tyr Ser Leu Ser Ser Val
            210                 215                 220
Val Thr Val Pro Ser Ser Ser Leu Gly Thr Gln Thr Tyr Ile Cys Asn
225                 230                 235                 240
Val Asn His Lys Pro Ser Asn Thr Lys Val Asp Lys Lys Val Glu Pro
                245                 250                 255
Lys Ser Cys Asp Lys Thr His Thr Cys Pro Pro Cys Pro Ala Pro Glu
            260                 265                 270
Leu Leu Gly Gly Pro Ser Val Phe Leu Phe Pro Pro Lys Pro Lys Asp
        275                 280                 285
Thr Leu Met Ile Ser Arg Thr Pro Glu Val Thr Cys Val Val Val Asp
290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
            340                 345                 350
Leu Asn Gly Lys Glu Tyr Lys Cys Lys Val Ser Asn Lys Ala Leu Pro
        355                 360                 365
Ala Pro Ile Glu Lys Thr Ile Ser Lys Ala Lys Gly Gln Pro Arg Glu
370                 375                 380
Pro Gln Val Tyr Thr Leu Pro Pro Ser Arg Asp Glu Leu Thr Lys Asn
385                 390                 395                 400
Gln Val Ser Leu Thr Cys Leu Val Lys Gly Phe Tyr Pro Ser Asp Ile
                405                 410                 415
Ala Val Glu Trp Glu Ser Asn Gly Gln Pro Glu Asn Asn Tyr Lys Thr
            420                 425                 430
Thr Pro Pro Val Leu Asp Ser Asp Gly Ser Phe Phe Leu Tyr Ser Lys
        435                 440                 445
Leu Thr Val Asp Lys Ser Arg Trp Gln Gln Gly Asn Val Phe Ser Cys
450                 455                 460
Ser Val Met His Glu Ala Leu His Asn His Tyr Thr Gln Lys Ser Leu
465                 470                 475                 480
Ser Leu Ser Pro Gly Lys
                485

<210> SEQ ID NO 14
<211> LENGTH: 1515
<212> TYPE: DNA
<213> ORGANISM: Homo sapiens

<400> SEQUENCE: 14
atgtacttgg gactgaactg tgtattcata gttttctct taaatggtgt ccagagtgaa    60
gtgaaactcg aggagtctgg aggaggcttg gtgcaacctg gaggatccat gaaactctct   120
tgtgttgcct ctggattcac ttttagtgac gcctggatga actgggtccg ccagtctcca   180
gagaaggggc ttgagtgggt tgctgaaatt agaagcaaag ctattaatcc tgcaatatac   240
tatgctgagt ctgtgaaagg gaggttcacc atattaagag atgattccaa agtagtgtc    300 tacctgcaaa tgaacagctt aagagctgaa gacactggaa tttattactg ttccaggtct   360
actatgatta cgacaaggga cccgtcccgg tacttcgatg tctggggcgc agggaccacg   420
gtcaccgtct ccagcgcttc caccaagggc ccatcggtct tccccctggc acctcctcc   480 aagagcaccg tctggggcgc agggaccacg gtcaccgtct ccagcgcttc caccaagggc   540
```

```
ccatcggtct tccccctggc accctcctcc aagagcacct ctgggggcac agcggccctg    600
ggctgcctgg tcaaggacta cttccccgaa ccggtgacgg tgtcgtggaa ctcaggcgcc    660
ctgaccagcg gcgtgcacac cttcccggct gtcctacagt cctcaggact ctactccctc    720
agcagcgtgg tgaccgtgcc ctccagcagc ttgggcaccc agacctacat ctgcaacgtg    780
aatcacaagc ccagcaacac caaggtggac aagaaagttg agcccaaatc ttgtgacaaa    840
actcacacat gcccaccgtg cccagcacct gaactcctgg ggggaccgtc agtcttcctc    900
ttccccccaa aacccaagga caccctcatg atctcccgga cccctgaggt cacatgcgtg    960
gtggtggacg tgagccacga agaccctgag gtcaagttca actggtacgt ggacggcgtg   1020
gaggtgcata atgccaagac aaagccgcgg gaggagcagt acaacagcac gtaccgtgtg   1080
gtcagcgtcc tcaccgtcct gcaccaggac tggctgaatg gcaaggagta caagtgcaag   1140
gtctccaaca aagccctccc agcccccatc gagaaaacca tctccaaagc caaagggcag   1200
ccccgagaac cacaggtgta caccctgccc ccatcccggg atgagctgac caagaaccag   1260
gtcagcctga cctgcctggt caaaggcttc tatcccagcg acatcgccgt ggagtgggag   1320
agcaatgggc agccggagaa caactacaag accacgcctc ccgtgctgga ctccgacggc   1380
tccttcttcc tctacagcaa gctcaccgtg gacaagagca ggtggcagca ggggaacgtc   1440
ttctcatgct ccgtgatgca tgaggctctg cacaaccact acacgcagaa gagcctctcc   1500
ctgtctccgg gtaaa                                                    1515

<210> SEQ ID NO 15
<211> LENGTH: 233
<212> TYPE: PRT
<213> ORGANISM: Homo sapiens

<400> SEQUENCE: 15

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Thr Ser Leu Ser
                20                  25                  30

Ala Ser Val Gly Glu Thr Val Thr Ile Thr Cys Arg Thr Ser Glu Asn
            35                  40                  45

Ile His Asn Phe Leu Thr Trp Tyr Gln Gln Lys Gln Gly Lys Ser Pro
        50                  55                  60

Gln Val Leu Val Tyr Asn Ala Lys Thr Leu Pro Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Ser Pro Trp Thr Phe Gly Gly Thr Lys Leu Glu Ile Lys Arg
        115                 120                 125

Thr Val Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190
```

```
Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 16
<211> LENGTH: 699
<212> TYPE: DNA
<213> ORGANISM: Homo sapiens

<400> SEQUENCE: 16
atgagtgtgc tcactcaggt cctggcgttg ctgctgctgt ggcttacagg tgccagatgt      60
gacatccaga tgactcagtc tccaacctcc ctatctgcat ctgtgggaga aactgtcacc     120
atcacatgtc gaacaagtga aatattcac aattttttaa catggtatca gcagaaacag      180
ggaaaatctc ctcaggtcct ggtctataat gcaaaaacct taccagatgg tgtgccatca     240
aggttcagtg gcagtggatc aggaacacaa tattctctca agatcaacag cctgcagcct     300
gaagattttg ggacttatta ctgtcaacat ttttggagta gtccgtggac gttcggtgga     360
ggcaccaagc tggaaatcaa acgtacggta gcgccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgt                           699

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 17
ttagcacccc tggccaagg                                                   19

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 18
cttactccct tggaggccat g                                                21
```

GLYCANS AS FUNCTIONAL CANCER TARGETS AND ANTIBODIES THERETO

CROSS-REFERENCE TO RELATED APPLICATIONS

This is the U.S. National Stage of International Application No. PCT/GB2014/053240, filed Oct. 31, 2014, which was published in English under PCT Article 21(2), which in turn claims the benefit of GB Patent Application No. 1319374.3, filed Nov. 1, 2013, which is incorporated herein by reference in its entirety.

The present invention relates to targeting of glycans in cancer and monoclonal antibodies (mAbs) that bind glycans.

Glycan structures are present on both protein and glycolipid backbones and can be massively over-expressed in cancer due to altered expression of glycosyltransferases. Glycolipids consist of a lipid tail with a carbohydrate head and constitute about 5% of lipid molecules in the outer monolayer. Examples of tumour associated glycolipids are gangliosides such as GM2, GD2, GD3 and fucosyl GM1. Glycolipids are postulated to be very good targets due to their high surface density, mobility, and association with membrane microdomains; all of which contribute to strong cellular interactions. However, generating anti-glycolipid antibodies is a challenging task as there is no T cell help and the mAbs are usually of low affinity and of the IgM subclass [1, 2]. Although generating mAbs to glycans expressed on proteins overcome this problem, they present new challenges as the mAbs rarely see just the small glycan but usually recognise the glycan on the specific protein giving a very restrictive expression.

Only a limited number of antibodies recognising glycans have been described. Several anti-Lewis (Le) carbohydrate antigen mAbs have been generated to date but they often have cross reactivity with a range of glycans expressed on normal tissues. Lewis carbohydrate antigens are formed by the sequential addition of fucose onto oligosaccharide precursor chains on glycoproteins or glycolipids through the action of a set of glycosyltransferases [3]. They can be divided into 2 groups, type I ($Le^a$ and $Le^b$) and type II ($Le^x$ and $Le^y$). $Le^a$ and $Le^b$ antigens are regarded as blood group antigens whereas $Le^x$ and $Le^y$ are viewed as tumour associated markers [4]. $Le^x$ is overexpressed in breast and gastrointestinal carcinomas. Normal expression of $Le^x$ is restricted to human polymorphonuclear neutrophils (PMNs). FC-215 (IgM) is a murine anti-$Le^x$ mAb which in a phase I clinical trial induced transient anti-tumour responses but profound neutropenia was observed and it has been suggested cross-linking of $Le^x$ epitopes on PMNs induced homotypic aggregation of PMNs [5]. A range of $Le^y$ antibodies have also been identified but a consistent problem with these has been the degree of cross reactivity with $Le^x$, and H type 2 structures causing red blood cell agglutination and gastrointestinal toxicity [6-8]. The mAb GNX-8 (human IgG1), which recognises $Le^b$-$Le^a$ has been generated. Based on the authors studies, it is predicted to be useful in the immunotherapy of human colorectal cancer [9]. Similarly the mAb 692/29 recognises $Le^{b/y}$ and shows anti-tumour responses against colonic tumours [10].

The sialylation of $Le^a$ is a key event in tumour progression, invasion and metastasis [11]. The antigen belongs to the neolactoseries and is a ligand of E-selectin expressed by endothelium. It is expressed on normal fibroblasts, on the luminal side of ductal epithelial cells and some parenchymatous cells, and is normally present on the inner surface of ductal epithelium, preventing accessibility to antibodies and immune effector cells. However, sialyl $Le^a$ ($SLe^a$) is found to be aberrantly expressed on the surface of a broad range of carcinomas such as breast [12], ovarian [13, 14], melanoma, colon [15], liver, lung and prostate. It is used as a serum marker in a range of cancers, including colorectal cancer to measure a patient's response to therapy [16]. Treatment with an anti-$SLe^a$ mAb against $SLe^a$ positive cancers has proven to be efficient in inhibiting pancreatic tumour metastasis in mouse models [17]. A human anti-$SLe^a$ mAb was produced using peripheral blood lymphocytes isolated from a breast cancer patient undergoing $SLe^a$-keyhole limpet hemocyanin (KLH) vaccination [11]. This mAb has shown specific binding to $SLe^a$ alone and promisingly induces ADCC and CDC of antigen positive cell lines as well as anti-tumour activity in a xenograft model. Recognition of $SLe^a$ can be achieved with commercial mAbs such as CA19-9 (also known as carbohydrate antigen 19-9; Abcam, Cambridge, UK, [13]) whilst the mAb 7-Le recognises $Le^a$ and the mAb 225-Le, $Le^b$ (Abcam). International patent application number WO 2005/108430 discloses an anti-cancer mouse mAb designated SC104. SC104 is a murine IgG1 mAb recognising sialyl-di-$Le^a$. The mAb has the ability to induce ADCC and CDC as well as direct tumour cell death without the need for immune effector cells through an apoptotic mechanism. In vivo studies demonstrated SC104 could inhibit tumour growth [18].

There is a need for further and improved cancer markers and therapies. The inventors have provided a new glycan, referred to herein as $LecLe^x$, described in more detail below. The inventors have also provided mAbs which demonstrate potent in vivo anti-tumour activity. The mAbs not only display potent immune-mediated cytotoxic activity against human colon cancer cells in vitro via antibody-dependent cell-mediated cytotoxicity (ADCC) and complement dependent cytotoxicity (CDC), but also have the ability to directly induce cell death without the need for immune effector cells. The inventors have unexpectedly found that a family of new mAbs, referred to herein as FG88 mAbs, recognise $Le^{a-x}$ related carbohydrates namely $LecLe^x$, $Le^aLe^x$, $Le^x$ containing glycans, Di-$Le^a$ and $Le^a$ containing glycans. Surprisingly, the inventors have found that these epitopes are highly expressed on tumours but have limited expression on normal tissues.

According to a first aspect of the invention, there is provided a glycan having the structure galβ1-3GLcNacβ1-3Galβ1-4(Fucα1-3)GlcNAc ($LecLe^x$) which is attached to a lipid or protein backbone.

According to a second aspect of the invention, there is provided isolated specific binding members capable of binding $LecLe^x$ glycan.

The invention also provides isolated specific binding member capable of binding $LecLe^x$, $Le^aLe^x$, Di-$Le^a$, $Le^x$ containing glycans and $Le^a$ containing glycans and directly inducing cell death without the need for immune effector cells. Such binding members may be for use in a method for treating cancer. The invention also provides for the use of such a binding partner in the manufacture of a medicament for the treatment of cancer. The invention also provides a method of treating cancer, comprising administering a binding partner of the invention to a subject in need of such treatment.

In one aspect, the present invention provides the mAb FG88.2 which binds to $LecLe^x$, $Le^aLe^x$, $Le^x$ containing glycan, $Le^a$ containing glycan, $Le^a$ and Di-$Le^a$.

In another aspect, the present invention provides for the mAb FG88.7 which binds to $LecLe^x$, Di-$Le^a$, $Le^a$, $Le^a$ containing glycans, $Le^x$ containing glycan and $Le^aLe^x$.

In this invention we show two murine IgG3k mAbs, FG88.2 and FG88.7, which bind to LecLe$^x$ and were generated by immunising Balb/c mice with tumour plasma membrane lipid extracts. Interestingly, they do not recognise PMNs. Although they can bind Le$^a$ they prefer more complex glycans and importantly, do not bind or lyse red blood cells. Evidence suggests that Le$^a$ and Le$^b$ antigens found in the secretions of various tissue types, have the capability of binding to the surface of erythrocytes [21]. The term ABH secretor refers to secretion of ABO blood group antigens; one of the differences in physiology between secretors and non-secretors being the secretion of these components in their body fluids [22]. If the antigen is derived from both the Le and Se alleles, Le$^a$ is converted to Le$^b$, which can be absorbed to the erythrocyte membrane, resulting in Le$^{a-b+}$ phenotype. If the antigen derives from only the Le allele, the antigenic form of Le$^a$ will be expressed, giving rise to the Le$^{a+b-}$ phenotype. If the Lewis antigen does not carry the Le allele, regardless of the presence or absence of Se allele, the erythrocyte phenotype will be Le$^{a-b-}$ [23]. Among Lewis antigen positive individuals, ABH secretors are always Le$^{a-b+}$ whereas ABH non-secretors are always Le$^{a+b-}$ [22]. In Caucasians, it was reported that approximately 80% are secretors and 20% are non-secretors. However, in another study in Negroes, 60% are secretors and 40% are non-secretors, suggesting the phenomenon may be due to racial variation [24].

Immunohistochemical binding of FG88 to colorectal (208 tumours), gastric (93 tumours), pancreatic (89 tumours), Lung (275 tumours), breast (902 tumour) and ovarian (186 tumours) tumour tissue microarrays (TMAs) revealed that FG88 mAbs stained 69% colorectal, 56% of gastric, 23% of lung, 27% of all breast types, 25% of ER negative breast cancer and 31% ovarian tumours. FG88.2 and FG88.7 showed weak staining on human jejunum, thymus and rectum; moderate staining on oesophagus, tonsil and pancreas; and strong staining on gall bladder, ileum and liver. In addition to the tissues stained by both mAbs, FG88.7 also stained rectum weakly. No staining was seen on placenta, skin, adipose, heart, skeletal, bladder, spleen, brain, stomach, breast, kidney, testis, cerebellum, cervix, lung, ovary, diaphragm, uterus, duodenum and thyroid.

A further aspect of the invention provides an isolated specific binding member comprising one or more binding domains selected from the amino acid sequence of residues 27 to 38 (CDRH1), 56-65 (CDRH2) and 105 to 121 (CDRH3) of FIG. 1a or 2a.

The binding domain may comprise an amino acid sequence substantially as set out as 1-133 (VH) of FIG. 1a or 2a.

In one embodiment, the member comprises a binding domain which comprises an amino acid sequence substantially as set out as residues 105 to 121 (CDRH3) of the amino acid sequence of FIG. 1a or 2a. In this embodiment, the isolated specific binding member may additionally comprise one or both, preferably both, of the binding domains substantially as set out as residues 27 to 38 (CDRH1) and residues 56 to 65 (CDRH2) of the amino acid sequence shown in FIGS. 1a and 2a.

In another aspect, the present invention provides an isolated specific binding member comprising one or more binding domains selected from the amino acid sequence of residues 27 to 38 (CDRL1), 56-65 (CDRL2) and 105 to 121 (CDRL3) of FIG. 1b or 2b.

The binding domain may comprise an amino acid sequence substantially as set out as residues 105 to 121 (CDRL3) of the amino acid sequence of FIGS. 1b and 2b. In this embodiment, the isolated specific binding member may additionally comprise one or both, preferably both, of the binding domains substantially as set out as residues 27 to 38 and (CDRL1) residues 56 to 65 of (CDRL2) the amino acid sequence shown in FIGS. 1b and 2b.

Specific binding members which comprise a plurality of binding domains of the same or different sequence, or combinations thereof, are included within the present invention. Each binding domain may be carried by a human antibody framework. For example, one or more binding regions may be substituted for the complementary determining regions (CDRs) of a whole human antibody or of the variable region thereof.

One isolated specific binding member of the invention comprises the sequence substantially as set out as residues 1 to 133 (VL) of the amino acid sequence shown in FIG. 1b or 2b.

In some embodiments binding members having sequences of the CDRs of FIG. 1a or FIG. 2a may be combined with binding members having sequences of the CDRs of FIG. 1b or 2b.

In a further aspect, the invention provides a binding member comprising residues 1 to 133 (VH) of the amino acid sequence of FIG. 1a or 2a, and residues 1 to 123 (VL) of the amino acid sequence of FIG. 1b or 2b.

The invention also encompasses binding partners as described above, but in which the sequences of the binding domains are substantially as set out in FIG. 1 or 2. Thus, binding partners as described above are provided, but in which in one or more binding domains differ from those depicted in FIG. 1 or 2 by from 1 to 5, from 1 to 4, from 1 to 3, 2 or 1 substitutions.

The invention also encompasses binding partners having the capability of binding to the same epitopes as the VH and VL sequences depicted in FIGS. 1 and 2. The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay compared to a control lacking the competing antibody (see, e.g., Junghans et al., Cancer Res. 50:1495, 1990, which is incorporated herein by reference).

The invention therefore further provides a binding member which competes for binding to LecLe$^x$, Le$^a$Le$^x$, Di-Le$^a$, Le$^x$ containing glycans or Le$^a$ containing glycans with an antibody comprising a VH chain having the amino acid sequence of residues 1 to 133 of FIG. 1a or 2a and a VL chain having the amino acid sequence of residues 1 to 123 of FIG. 1b or 2b.

In a preferred embodiment the competing binding partner competes for binding to LecLe$^x$ with an antibody comprising a VH chain having the amino acid sequence of residues 1 to 133 of FIG. 1a or 2a and a VL chain having the amino acid sequence of residues 1 to 123 of FIG. 1b or 2b.

In a further embodiment the competing binding partner competes for binding to LecLe$^x$, Le$^a$Le$^x$, Di-Le$^a$, Le$^x$ containing glycans or Le$^a$ containing glycans with an antibody comprising a VH chain having the amino acid sequence of residues 1 to 133 of FIG. 1a and a VL chain having the amino acid sequence of residues 1 to 123 of FIG. 1b, or with an antibody comprising a VH chain having the amino acid sequence of residues 1 to 133 of FIG. 2a and a VL chain having the amino acid sequence of residues 1 to 123 of FIG. 2b.

Preferably, competing binding partners are antibodies, for example monoclonal antibodies, or any of the antibody variants or fragments mentioned throughout this document.

Once a single, archtypal mAb, for example an FG88 mAB, has been isolated that has the desired properties described herein, it is straightforward to generate other mAbs with similar properties, by using art-known methods. For example, the method of Jespers et al., Biotechnology 12:899, 1994, which is incorporated herein by reference, may be used to guide the selection of mAbs having the same epitope and therefore similar properties to the archtypal mAb. Using phage display, first the heavy chain of the archtypal antibody is paired with a repertoire of (preferably human) light chains to select a glycan-binding mAb, and then the new light chain is paired with a repertoire of (preferably human) heavy chains to select a (preferably human) glycan-binding mAb having the same epitope as the archtypal mAb.

MAbs that are capable of binding $LecLe^x$, $Le^aLe^x$, $Di-Le^a$, $Le^x$ containing glycans and $Le^a$ containing glycans and directly inducing cell death without the need for immune effector cells, and are at least 90%, 95% or 99% identical in the VH and/or VL domain to the VH or VL domains of FIG. 1 or 2, are included in the invention. Preferably such antibodies differ from the sequences of FIG. 1 or 2 by a small number of functionally inconsequential amino acid substitutions (e.g., conservative substitutions), deletions, or insertions.

In any embodiment of the invention, the specific binding pair may be an antibody or an antibody fragment, Fab, $(Fab')_2$, scFv, Fv, dAb, Fd or a diabody. In some embodiments the antibody is a polyclonal antibody. In other embodiments the antibody is a monoclonal antibody. Antibodies of the invention may be humanised, chimeric or veneered antibodies, or may be non-human antibodies of any species.

In one embodiment the specific binding partner of the invention is mouse antibody FG88.2 which comprises a heavy chain as depicted in FIG. 1a and a light chain as depicted in FIG. 1b.

In another embodiment the specific binding partner of the invention is mouse antibody FG88.7 which comprises a heavy chain as depicted in FIG. 2a and a light chain as depicted in FIG. 2b.

In another embodiment the specific binding partner of the invention is chimeric FG88.2 which comprises a heavy chain as depicted in FIG. 1d and a light chain as depicted in FIG. 1e.

In another embodiment the specific binding partner of the invention is chimeric FG88.7 which comprises a heavy chain as depicted in FIG. 2d and a light chain as depicted in FIG. 2e.

Specific binding members of the invention may carry a detectable or functional label.

In further aspects, the invention provides an isolated nucleic acid which comprises a sequence encoding a specific binding member of the aspects of the invention, and methods of preparing specific binding members of the invention which comprise expressing said nucleic acids under conditions to bring about expression of said binding member, and recovering the binding member.

Specific binding members according to the invention may be used in a method of treatment or diagnosis of the human or animal body, such as a method of treatment of a tumour in a patient (preferably human) which comprises administering to said patient an effective amount of a specific binding member of the invention. The invention also provides a specific binding member of the present invention for use in medicine, as well as the use of a specific binding member of the present invention in the manufacture of a medicament for the diagnosis or treatment of a tumour.

The invention also provides the antigen to which the specific binding members of the present invention bind. In one embodiment, a $LecLe^x$ which is capable of being bound, preferably specifically, by a specific binding member of the present invention is provided. The $LecLe^x$ may be provided in isolated form, and may be used in a screen to develop further specific binding members therefor. For example, a library of compounds may be screened for members of the library which bind specifically to the $LecLe^x$. The $LecLe^x$ may on a lipid backbone (i.e. a $LecLe^x$ ceramide) or on a protein backbone. When on a protein backbone, it may have a molecular weight of about 50-150 kDa, as determined by SDS-PAGE.

In a further aspect the invention provides an isolated specific binding member capable of binding $LecLe^x$, $Le^aLe^x$, $Di-Le^a$, $Le^x$ containing glycans and $Le^a$ containing glycans for use in the diagnosis or prognosis of colorectal, gastric, pancreatic, lung, ovarian and breast tumours.

The invention further provides a method for diagnosis of cancer comprising using a specific binding partner of the invention to detect $LecLe^x$, $Le^aLe^x$, $Di-Le^a$, $Le^x$ containing glycans or $Le^a$ containing glycans in a sample from an individual. In some embodiments, in the diagnostic method the pattern of glycans detected by the binding partner is used to stratify therapy options for the individual.

These and other aspects of the invention are described in further detail below.

As used herein, a "specific binding member" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of specific binding pairs are antigen-antibody, biotin-avidin, hormone-hormone receptor, receptor-ligand, enzyme-substrate. The present invention is generally concerned with antigen-antibody type reactions, although it also concerns small molecules which bind to the antigen defined herein.

As used herein, "treatment" includes any regime that can benefit a human or non-human animal, preferably mammal. The treatment may be in respect of an existing condition or may be prophylactic (preventative treatment).

As used herein, a "tumour" is an abnormal growth of tissue. It may be localised (benign) or invade nearby tissues (malignant) or distant tissues (metastatic). Tumours include neoplastic growths which cause cancer and include oesophageal, colorectal, gastric, breast and endometrial tumours, as well as cancerous tissues or cell lines including, but not limited to, leukaemic cells. As used herein, "tumour" also includes within its scope endometriosis.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to as a "mAb".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g., murine, antibody and the constant region of a human antibody. Methods for making humanised antibodies are described in, for example, U.S. Pat. No. 5,225,539.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [25] which consists of a VH domain; (v) isolated CDR regions; (vi) F(ab') 2 fragments, a bivalent fragment comprising two linked Fab fragments; (vii) single chain Fv molecules (scFv), wherein a VH domain and a VL domain are linked by a peptide linker which allows the two domains to associate to form an antigen binding site [26, 27]; (viii) bispecific single chain Fv dimers (PCT/US92/09965) and; (ix) "diabodies", multivalent or multispecific fragments constructed by gene fusion (WO94/13804; [28]).

Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways [29], e.g., prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in [30].

Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

"Specific" is generally used to refer to the situation in which one member of a specific binding pair will not show any significant binding to molecules other than its specific binding partner(s), and, e.g., has less than about 30%, preferably 20%, 10%, or 1% cross reactivity with any other molecule. The term is also applicable where e.g., an antigen binding domain is specific for a particular epitope which is carried by a number of antigens, in which case, the specific binding member carrying the antigen binding domain will be able to bind to the various antigens carrying the epitope.

"Isolated" refers to the state in which specific binding members of the invention or nucleic acid encoding such binding members will preferably be, in accordance with the present invention. Members and nucleic acid will generally be free or substantially free of material with which they are naturally associated such as other polypeptides or nucleic acids with which they are found in their natural environment, or the environment in which they are prepared (e.g., cell culture) when such preparation is by recombinant DNA technology practised in vitro or in vivo. Specific binding members and nucleic acid may be formulated with diluents or adjuvants and still for practical purposes be isolated—for example, the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

By "substantially as set out" it is meant that the CDR regions of the invention will be either identical or highly homologous to the specified regions of FIG. 1 or 2. By "highly homologous" it is contemplated that from 1 to 5, from 1 to 4, from 1 to 3, 2 or 1 substitutions may be made in the CDRs.

The invention also includes within its scope polypeptides having the amino acid sequence as set out in FIG. 1 or 2, polynucleotides having the nucleic acid sequences as set out in Figure A or B and sequences having substantial identity thereto, for example, 70%, 80%, 85%, 90%, 95% or 99% identity thereto. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) [31], modified as in Karlin and Altschul (1993) [32]. The NBLAST and XBLAST programs of Altschul et al. (1990) [33] have incorporated such an algorithm. BLAST nucleotide searches can be performed with the NBLAST program, score=100, word length=12 to obtain nucleotide sequences homologous to a nucleic acid molecules of the invention. BLAST protein searches can be performed with the XBLAST program, score=50, word length=3 to obtain amino acid sequences homologous to a protein molecules of the invention. To obtain gapped alignments for comparison purposes, Gapped BLAST can be utilized as described in Altschul et al. (1997) [34]. Alternatively, PSI-Blast can be used to perform an iterated search that detects distant relationships between molecules (Id.). When utilizing BLAST, Gapped BLAST, and PSI-Blast programs, the default parameters of the respective programs (e.g., XBLAST and NBLAST) can be used. Available on the World Wide Web at ncbi.nlm.nih.gov. Another example of a mathematical algorithm utilized for the comparison of sequences is the algorithm of Myers and Miller, [35]. The ALIGN program (version 2.0) which is part of the GCG sequence alignment software package has incorporated such an algorithm. Other algorithms for sequence analysis known in the art include ADVANCE and ADAM as described in Torellis and Robotti (1994) [36]; and FASTA described in Pearson and Lipman (1988) [37]. Within FASTA, ktup is a control option that sets the sensitivity and speed of the search.

Isolated specific binding members of the present invention are capable of binding to a LecLe$^x$ carbohydrate, which may be a LecLe$^x$ ceramide or may be on a protein moiety. In one embodiment, the CDR3 regions, comprising the amino acid sequences substantially as set out as residues 105 to 121 (CDRH3) of FIGS. 1a and 2a and 105 to 121 of FIGS. 1b and 2b, are carried in a structure which allows the binding of these regions to a LecLe$^x$ carbohydrate.

The structure for carrying the CDR3s of the invention will generally be of an antibody heavy or light chain sequence or substantial portion thereof in which the CDR3 regions are located at locations corresponding to the CDR3 region of naturally-occurring VH and VL antibody variable domains encoded by rearranged immunoglobulin genes. The structures and locations of immunoglobulin variable domains may be determined by reference to the website imgt.org/. The amino acid sequence substantially as set out as residues 105 to 121 of FIGS. 1a and 2a may be carried as the CDR3 in a human heavy chain variable domain or a substantial portion thereof, and the amino acid sequence substantially as set out as residues and 105 to 121 of FIGS. 1b and 2b may be carried as the CDR3 in a human light chain variable domain or a substantial portion thereof.

The variable domains may be derived from any germline or rearranged human variable domain, or may be a synthetic variable domain based on consensus sequences of known human variable domains. The CDR3-derived sequences of the invention may be introduced into a repertoire of variable domains lacking CDR3 regions, using recombinant DNA technology.

For example, Marks et al., (1992) [38] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. (1992) [38] further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (1994) [39] who describes the technique in relation to a β-lactamase gene but observes that the approach may be used for the generation of antibodies.

A further alternative is to generate novel VH or VL regions carrying the CDR3-derived sequences of the invention using random mutagenesis of, for example, the SC104 VH or VL genes to generate mutations within the entire variable domain. Such a technique is described by Gram et al., (1992) [40], who used error-prone PCR.

Another method which may be used is to direct mutagenesis to CDR regions of VH or VL genes. Such techniques are disclosed by Barbas et al., (1994) [41] and Schier et al., (1996) [42].

A substantial portion of an immunoglobulin variable domain will generally comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps, including the introduction of linkers to join variable domains of the invention to further protein sequences including immunoglobulin heavy chains, other variable domains (for example in the production of diabodies) or protein labels as discussed in more detail below.

One embodiment of the invention provides specific binding members comprising a pair of binding domains based on the amino acid sequences for the VL and VH regions substantially as set out in FIG. 1, i.e. amino acids 1 to 133 (VH) of FIGS. 1a and 2a and amino acids 1 to 133 (VL) of FIGS. 1b and 2b. Single binding domains based on either of these sequences form further aspects of the invention. In the case of the binding domains based on the amino acid sequence for the VH region substantially set out in FIGS. 1a and 2a, such binding domains may be used as targeting agents since it is known that immunoglobulin VH domains are capable of binding target antigens in a specific manner.

In the case of either of the single chain specific binding domains, these domains may be used to screen for complementary domains capable of forming a two-domain specific binding member which has in vivo properties as good as or equal to the FG88 antibodies disclosed herein.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al., [38].

Specific binding members of the present invention may further comprise antibody constant regions or parts thereof. For example, specific binding members based on the VL region shown in FIGS. 1b and 2b may be attached at their C-terminal end to antibody light chain constant domains including human Cκ or Cλ, chains. Similarly, specific binding members based on VH region shown in Figure b and 2b may be attached at their C-terminal end to all or part of an immunoglobulin heavy chain derived from any antibody isotype, e.g., IgG, IgA, IgE and IgM and any of the isotype sub-classes, particularly IgG1, IgG2 and IgG4.

Specific binding members of the present invention can be used in methods of diagnosis and treatment of tumours in human or animal subjects.

When used in diagnosis, specific binding members of the invention may be labelled with a detectable label, for example a radiolabel such as $^{131}$I or $^{99}$Tc, which may be attached to specific binding members of the invention using conventional chemistry known in the art of antibody imaging. Labels also include enzyme labels such as horseradish peroxidase. Labels further include chemical moieties such as biotin which may be detected via binding to a specific cognate detectable moiety, e.g., labelled avidin.

Although specific binding members of the invention have in themselves been shown to be effective in killing cancer cells, they may additionally be labelled with a functional label. Functional labels include substances which are designed to be targeted to the site of cancer to cause destruction thereof. Such functional labels include toxins such as ricin and enzymes such as bacterial carboxypeptidase or nitroreductase, which are capable of converting prodrugs into active drugs. In addition, the specific binding members may be attached or otherwise associated with chemotherapeutic or cytotoxic agents, such as maytansines (DM1 and DM4), onides, auristatins, calicheamicin, duocamycin, doxorubicin or radiolabels, such as $^{90}$Y or $^{131}$I.

Furthermore, the specific binding members of the present invention may be administered alone or in combination with other treatments, either simultaneously or sequentially, dependent upon the condition to be treated. Thus, the present invention further provides products containing a specific binding member of the present invention and an active agent as a combined preparation for simultaneous, separate or sequential use in the treatment of a tumour. Active agents may include chemotherapeutic or cytotoxic agents including, 5-Fluorouracil, cisplatin, Mitomycin C, oxaliplatin and tamoxifen, which may operate synergistically with the binding members of the present invention. Other active agents may include suitable doses of pain relief drugs such as non-steroidal anti-inflammatory drugs (e.g., aspirin, paracetamol, ibuprofen or ketoprofen) or opitates such as morphine, or anti-emetics.

Whilst not wishing to be bound by theory, the ability of the binding members of the invention to synergise with an active agent to enhance tumour killing may not be due to immune effector mechanisms but rather may be a direct consequence of the binding member binding to cell surface bound LecLe$^x$, Le$^a$Le$^x$, Di-Le$^a$ and Le$^a$ glycans.

Specific binding members of the present invention will usually be administered in the form of a pharmaceutical composition, which may comprise at least one component in addition to the specific binding member. The pharmaceutical composition may comprise, in addition to active ingredient, a pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g., intravenous.

It is envisaged that injections will be the primary route for therapeutic administration of the compositions although delivery through a catheter or other surgical tubing is also used. Some suitable routes of administration include intravenous, subcutaneous, intraperitoneal and intramuscular administration. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Implantable or microcapsular sustained release matrices include polylactides (U.S. Pat. No. 3,773,919; EP-A-0058481) copolymers of L-glutamic acid and gamma ethyl-L-glutamate [43], poly (2-hydroxyethyl-methacrylate). Liposomes containing the polypeptides are prepared by well-known methods: DE 3,218, 121A; Epstein et al, PNAS USA, 82: 3688-3692, 1985; Hwang et al, PNAS USA, 77: 4030-4034, 1980; EP-A-0052522; EP-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g., decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, $16^{th}$ edition, Oslo, A. (ed), 1980 [45].

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m$^2$ of antibody provides a serum concentration of approximately 20 nM for approximately eight days.

As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of the LecLe$^x$ carbohydrate.

The dose of the composition will be dependent upon the properties of the binding member, e.g., its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 300 μg of antibody per patient per administration are preferred, although dosages may range from about 10 μg to 6 mg per dose. Different dosages are utilised during a series of sequential inoculations; the practitioner may administer an initial inoculation and then boost with relatively smaller doses of antibody.

This invention is also directed to optimise immunisation schedules for enhancing a protective immune response against cancer.

The binding members of the present invention may be generated wholly or partly by chemical synthesis. The binding members can be readily prepared according to well-established, standard liquid or, preferably, solid-phase peptide synthesis methods, general descriptions of which are broadly available (see, for example, in J. M. Stewart and J. D. Young, (1984) [46], in M. Bodanzsky and A. Bodanzsky, (1984) [47]; or they may be prepared in solution, by the liquid phase method or by any combination of solid-phase, liquid phase and solution chemistry, e.g., by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding member according to the present invention is to express the nucleic acid encoding it, by use of nucleic acid in an expression system.

The present invention further provides an isolated nucleic acid encoding a specific binding member of the present invention. Nucleic acid includes DNA and RNA. In a preferred aspect, the present invention provides a nucleic acid which codes for a specific binding member of the invention as defined above. Examples of such nucleic acid are shown in FIGS. 1 and 2. The skilled person will be able to determine substitutions, deletions and/or additions to such nucleic acids which will still provide a specific binding member of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a specific binding member of the invention forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*. The expression of antibodies and antibody fragments in prokaryotic cells such as *E. coli* is well established in the art. For a review, see for example Plückthun (1991) [48]. Expression in eukaryotic cells in culture is also available to those skilled in the art as an option for production of a specific binding member, see for recent review, for example Reff (1993) [49]; Trill et al., (1995) [50].

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., 'phage, or phagemid, as appropriate. For further details see, for example, Sambrook et al., (1989) [51]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al., (1992) [52].

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene.

In one embodiment, the nucleic acid of the invention is integrated into the genome (e.g., chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Preferred features of each aspect of the invention are as for each of the other aspects mutatis mutandis. The prior art documents mentioned herein are incorporated to the fullest extent permitted by law.

The inventors have unexpectedly found that a family of mAbs FG88 recognises $LecLe^x$, $Le^aLe^x$, $Di-Le^a$ and $Le^a$ containing glycans induced non apoptotic direct cell death without immune effector cells.

In one aspect, of the present invention it provides drugs which bind to $LecLe^x$, $Le^aLe^x$, $Le^a$ containing glycan, $Le^a$ and $Di-Le^a$ and induce non apoptotic cell death.

FG88 mAbs induced membrane damage to cells resulting in cell clumping, loss of microvilli, uptake of small molecular weight dyes and pore formation. The cell death was not inhibited by pan-caspase inhibitors and did not induce DNA fragmentation suggesting that the death was not mediated via apoptosis. Over time cells developed larger pores and lysed in a mechanism similar to oncosis. This is similar to a number of mAbs recognising other glycan but has not been described for mAbs recognising $LecLe^x$, $Le^aLe^x$, $Le^a$ containing glycan, $Le^a$ and $Di-Le^a$ [53-58]. The FG88 mAbs also exhibited potent in vitro cytotoxic activity through antibody dependent cellular cytotoxicity (ADCC) and complement cellular cytotoxicity (CDC). The administration of FG88.2 and FG88.7 mAbs (0.1 mg intravenous (i.v.) twice a week for 9 weeks) to mice with established metastases in the liver and peritoneal cavity results in complete tumour eradication and cure of 40% of the mice. The potential of FG88.2 and FG88.7 mAbs in eradicating well-established tumours without concomitant chemotherapy indicates their potential as monotherapeutic agents for the treatment of multiple $LecLe^x$, $Le^aLe^x$, $Di-Le^a$ and $Le^a$ expressing human solid tumours.

BRIEF DESCRIPTION OF THE DRAWINGS

Figure Legends

FIG. 1a: Amino acid and nucleotide sequence for the mouse IgG3 heavy chain of the FG88.2 mAb (SEQ ID NOs: 1 and 2, respectively). Numbers refer to the standardised IMGT system for the numbering of antibody sequences [59]. FIG. 1b: Amino acid and nucleotide sequence for the mouse kappa chain of the FG88.2 mAb (SEQ ID NOs: 3 and 4, respectively). Numbers refer to the standardised IMGT system for the numbering of antibody sequences [59]. FIG. 1c: The chimeric version of the FG88.2 mAb (original murine variable regions linked to human constant region sequence), produced by a transfected cell line, binds the target cell line (C170). FIG. 1d: Amino acid and nucleotide sequence for the human IgG1 heavy chain of the FG88.2 mAb (SEQ ID NOs: 5 and 6, respectively). Numbers refer to the standardised IMGT system for the numbering of antibody sequences [59]. FIG. 1e: Amino acid and nucleotide sequence for the human kappa chain of the FG88.2 mAb (SEQ ID NOs: 7 and 8, respectively). Numbers refer to the standardised IMGT system for the numbering of antibody sequences [59].

FIG. 2a: Amino acid and nucleotide sequence for the mouse IgG3 heavy chain of the FG88.7 mAb (SEQ ID NOs: 9 and 10, respectively). Numbers refer to the standardised IMGT system for the numbering of antibody sequences [59]. FIG. 2b: Amino acid and nucleotide sequence for the mouse kappa chain of the FG88.7 mAb (SEQ ID NOs: 11 and 12, respectively). Numbers refer to the standardised IMGT system for the numbering of antibody sequences [59]. FIG. 2c: The chimeric version of the FG88.7 mAb (original murine variable regions linked to human constant region sequence), produced by a transfected cell line, binds the target cell line (C170). FIG. 2d: Amino acid and nucleotide sequence for the human IgG1 heavy chain of the FG88.7 mAb (SEQ ID NOs: 13 and 14, respectively). Numbers refer to the standardised IMGT system for the numbering of antibody sequences [59]. FIG. 2e: Amino acid and nucleotide sequence for the human kappa chain of the FG88.7 mAb (SEQ ID NOs: 15 and 16, respectively). Numbers refer to the standardised IMGT system for the numbering of antibody sequences [59].

FIG. 9c: Time-lapse confocal microscopy of Alexa Fluor® 488 labelled FG88 mAbs internalizing into live C170 cells. Merged images taken every 20 minutes demonstrate FG88 internalization and co-localization with lysosomal compartments (arrows). The nucleus was labelled with Hoechst 33258, lysosomal compartments with LysoTracker® Deep Red and the plasma membrane with CellMask™ Orange. Magnification 60x.

FIG. 9d: Targeted toxin (saporin) delivery by internalized FG88 mAbs in a panel of cancer cell lines [C170 (i), Panc 1 (ii), ST16 (iii) and HT29 (iv)]. The anti-proliferative effect of internalized FG88 mAbs preincubated with a saporin-linked anti-mouse IgG Fab fragment was evaluated using $^3$H-thymidine incorporation. Results (mean±STD from three independent experiments) are presented as a percentage of proliferation of cells treated with primary mAbs only; normalized values are shown for C170 and Panel [FG88.7 (○); FG88.2 (▲)].

Figure 3A:
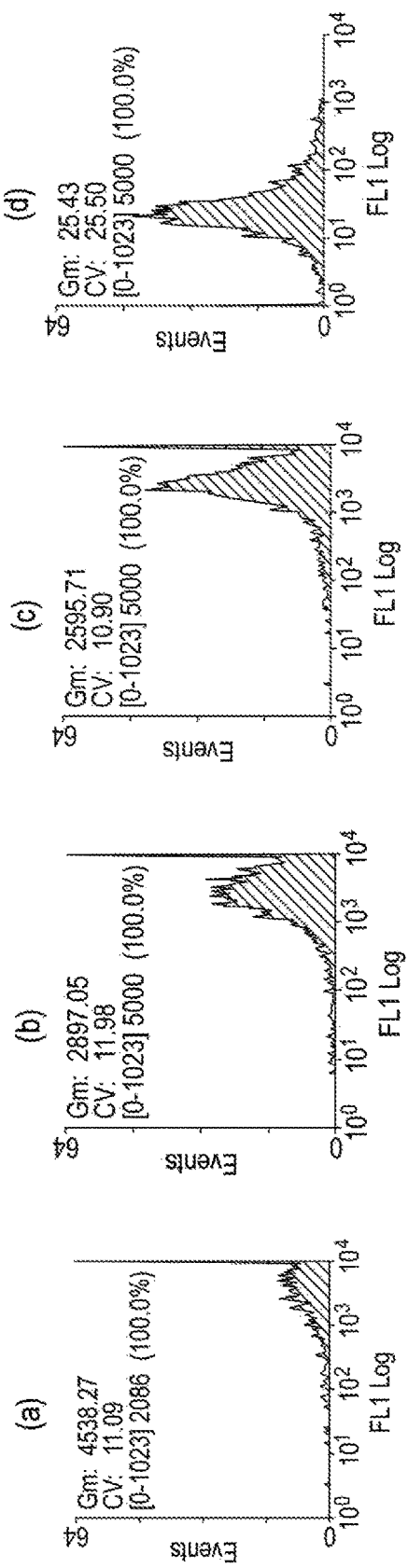
FIG. 3a: Binding of FG88 hybridoma supernatant to the colorectal cancer cell line Colo205 shown by indirect immunofluorescence staining and flow cytometric analysis. The panels represent (a) FG88.2 (neat supernatant); (b) FG88.7 (neat supernatant); (c) the positive control W6/32 (5 µg/ml), a mAb directed against human class I histocompatibility antigens (HLA-A,B,C); and (d) the negative control mouse immunoglobulin (IgG) (5 µg/ml). Results are expressed as geometric mean values (Gm).

The Sequence Listing is submitted as an ASCII text file in the form of the file named Sequence_Listing.txt, which was created on Aug. 8, 2016, and is 37,033 bytes, which is incorporated by reference herein.

DETAILED DESCRIPTION OF THE INVENTION

The invention will now be described further in the following non-limiting examples and accompanying drawings.

Methods

Binding to Tumour Cell Lines:

$1\times10^5$ cancer cells were incubated with 50 µl of primary antibodies at 4° C. for 1 hr. Cells were washed with 200 µl of RPMI 10% new born calf serum (NBCS: Sigma, Poole, UK) and spun at 1,000 rpm for 5 min. Supernatant was discarded and 50 µl of FITC conjugated anti-mouse IgG Fc specific mab (Sigma; 1/100 in RPMI 10% NBCS) was used as secondary antibody. Cells were incubated at 4° C. in dark for 1 hr then washed with 200 µl RPMI 10% NBCS and spun at 1,000 rpm for 5 min. After discarding supernatant, 0.4% formaldehyde was used to fix the cells. Samples were analysed on a Beckman coulter FC-500 flow cytometer (Beckman Coulter, High Wycombe, UK). To analyse and plot raw data, WinMDI 2.9 software was used.

Binding to Blood:

50 µl of healthy donor blood was incubated with 50 µl primary antibody at 4° C. for 1 hr. The blood was washed with 150 µl of RPMI 10% NBCS and spun at 1,000 rpm for 5 min. Supernatant was discarded and 50 µl FITC conjugated anti-mouse IgG Fc specific mAb (1/100 in RPMI 10% NBCS) was used as the secondary antibody. Cells were incubated at 4° C. in the dark for 1 hr then washed with 150 µl RPMI 10% NBCS and spun at 1,000 rpm for 5 min. After discarding the supernatant, 50 µl/well Cal-Lyse (Invitrogen, Paisley, UK) was used followed by 500 µl/well distilled water to lyse red blood cells. The blood was subsequently spun at 1,000 rpm for 5 min. Supernatant was discarded and 0.4% formaldehyde was used to fix the cells. Samples were analysed on a FC-500 flow cytometer (Beckman Coulter). To analyse and plot raw data, WinMDI 2.9 software was used.

Erythrocyte Assays:

Healthy donor erythrocytes were washed 3 times in PBS and then resuspended in 10 times the packed cell volume of PBS. 50 µl of washed erythrocytes were then incubated with 50 µl primary antibodies at 37° C. for 1 hr. Cells were washed with 150 µl of PBS and spun at 2,000 rpm for 5 min. Supernatant was discarded and cells resuspended in 50 µl FITC-conjugated anti-mouse IgG Fc-specific secondary antibody (Sigma, 1/100 dilution in PBS, 1% BSA). Cells were incubated at 37° C. in the dark for 1 hr then washed with 150 µl PBS and spun at 2,000 rpm for 5 min. Supernatant was discarded and cells were resuspended in 500 µl PBS. Samples were analysed on a MACSQ flow cytometer (Miltenyi Biotech, Bisley, UK) using MACSQ software.

Plasma Membrane Glycolipid Extraction:

Colo205 cell pellet ($5\times10^7$ cells) was resuspended in 500 µl of Mannitol/HEPES buffer (50 mM Mannitol, 5 mM HEPES, pH7.2, both Sigma) and passed through 3 needles (23G, 25G, 27G) each with 30 pulses. 5 µl of 1M CaCl$_2$ was added to the cells and passed through 3 needles each with 30 pulses as above. Sheared cells were incubated on ice for 20 min then spun at 3,000 g for 15 min at room temperature. Supernatant was collected and spun at 48,000 g for 30 min at 4° C. and the supernatant was discarded. The pellet was resuspended in 1 ml methanol followed by 1 ml chloroform and incubated with rolling for 30 min at room temperature. The sample was then spun at 1,200 g for 10 min to remove precipitated protein. The supernatant, containing plasma membrane glycolipids, was collected and stored at −20° C.

TLC Analysis of FG88 Glycolipid Binding:

Lipid samples were blotted onto silica plates and developed in chloroform/methanol/distilled water (60:30:5 by volume) twice followed by hexane:diethyl ether:acetic acid (80:20:1.5 by volume) twice. The dried plates were sprayed with 0.1% polyisobutylmethacrylate (Sigma) in acetone. After drying in air, the plates were blocked with PBS 2% BSA for 1 hr at room temperature. The plates were then incubated overnight at 4° C. with primary antibodies diluted in PBS 2% BSA. The plates were then washed 3 times with PBS and incubated with biotin-conjugated anti-mouse IgG Fc specific secondary antibody (Sigma) diluted 1/1000 in PBS 2% BSA for 1 hr at room temperature. The plates were subsequently washed again in PBS before incubating with IRDye 800CW streptavidin (LICOR Biosciences, Cambridge, UK) diluted 1/1000 in PBS 2% BSA for 1 hr at room temperature in the dark. The plates were washed a further 3 times with PBS and air dried in the dark. Lipid bands were visualized using a LICOR Odyssey scanner.

Glycome Analysis:

To clarify the fine specificities of the FG88 mAbs further, the antibodies were FITC labelled and sent to the Consortium for Functional Glycomics where they were screened against ≥600 natural and synthetic glycans. Briefly, synthetic and mammalian glycans with amino linkers were printed onto N-hydroxysuccinimide (NHS)-activated glass microscope slides, forming amide linkages. Printed slides were incubated with 1 µg/ml of antibody for 1 hr before the binding was detected with Alexa488-conjugated goat anti-mouse IgG. Slides were then dried, scanned and the screening data compared to the Consortium for Functional Glycomics database.

Affinity Analysis

Surface Plasmon Resonance (SPR, Biacore X, GE Healthcare) analysis was used to investigate real-time binding kinetics of the FG88 mAbs. Polyvalent Le$^a$-HSA was coupled onto a CM5 biosensor chip according to the manufacturer's instructions and a reference cell was treated in a similar manner, but omitting the Le$^a$ conjugate. FG88 mAbs diluted in HBS-P buffer (10 mmol/L HEPES, pH 7.4, 150 mmol/L NaCl, 0.005% (v/v) surfactant P20) were run across the chip at a flow rate of 30 µl/min and BIAevaluation software 4.1 was used to determine the kinetic binding parameters from which affinities are calculated.

SDS-PAGE and Western Blot Analysis:

Briefly, 1×10$^5$ or 10$^6$ cell equivalents of Colo205 cell lysate, plasma membrane, total lipid extract, plasma membrane lipid extract or C170 cell lysates were analysed for FG88 binding. Tumour cell total and plasma membrane lipid extracts and cell lysates were reduced with dithiothreitol (DTT; Pierce Biotechnology, ThermoFisher, Loughborough, UK) and subjected to SDS-PAGE using NOVEX 4% to 12% Bis-Tris gels (Invitrogen), and transferred to Hybond-P PVDF membranes (GE Healthcare, Amersham, UK) using 1× transfer buffer (20×, Invitrogen) and 20% (v/v) methanol at 30V for 1 hr. Membranes were blocked with 5% (w/v) non-fat dry milk in 0.05% (v/v) Tween-PBS for 1 hr then probed with primary antibodies diluted in Tween-PBS, 2% BSA for 1 hr. Primary antibody binding was detected using biotin-conjugated anti-mouse IgG Fc specific secondary antibody (Sigma; 1/2000 dilution in Tween-PBS, 2% BSA) for 1 hr, and visualized using IRDye 800CW streptavidin (LICOR Biosciences, UK; 1/1000 in Tween-PBS 2% BSA).

Identification of FG88.2 and FG88.7 Heavy and Light Chain Variable Regions.

Cell Source and Total RNA Preparation:

Approximately 5×10$^6$ cells from hybridomas FG88.2 and FG88.7 were taken from tissue culture, washed once in PBS, and the cell pellet treated with 5000 Trizol (Invitrogen). After the cells had been dispersed in the reagent, they were stored at −80° C. until RNA was prepared following manufacturer's protocol. RNA concentration and purity were determined by Nanodrop. Prior to cDNA synthesis, RNA was DNase I treated to remove genomic DNA contamination (DNase I recombinant, RNase-free, Roche Diagnostics, Burgess Hill, UK) following manufacturer's recommendations.

cDNA Synthesis:

First-strand cDNA was prepared from 3 µg of total RNA using a first-strand cDNA synthesis kit and AMV reverse transcriptase following manufacturer's protocol (Roche Diagnostics). After cDNA synthesis, reverse transcriptase activity was destroyed by incubation at 90° C. for 10 mins and cDNA stored at −20° C.

GAPDH PCR to Assess cDNA Quality:

A PCR was used to assess cDNA quality; primers specific for the mouse GAPDH house-keeping gene (5'-TTAGCAC-CCCTGGCCAAGG-3' (SEQ ID NO: 17) and 5'-CT-TACTCCCTTGGAGGCCATG-3' (SEQ ID NO: 18)) were used with a hot-start Taq polymerase (NEB, Hitchen, UK) for 35 cycles (95° C., 3 mins followed by 35 cycles of 94° C./30 secs, 55° C./30 secs, 72° C./1 min; final polishing step of 10 mins at 72° C.). Amplified products were assessed by agarose gel electrophoresis.

PCR Primer Design for Cloning FG88.7 Variable Regions:

Primers were designed to amplify the heavy and light chain variable regions based upon the PCR product sequence data. Primers were designed to allow cloning of the relevant chain into unique restriction enzyme sites in the hIgG1/kappa double expression vector pDCOrig-hIgG1. Each 5' primer was targeted to the starting codon and leader peptide of the defined variable region, with a Kozak consensus immediately 5' of the starting codon. Each 3' primer was designed to be complementary to the joining region of the antibody sequence, to maintain reading frame after cloning of the chain, and to preserve the amino acid sequence usually found at the joining region/constant region junction. All primers were purchased from Eurofins MWG.

Heavy Chain Variable Region PCR:

Immunoglobulin heavy chain variable region usage was determined using PCR with a previously published set of primers [60]. Previous results using a mouse mAb isotyping test kit (Serotec, Oxford, UK) had indicated that FG88.2 and FG88.7 were both mouse IgG3 antibodies. Appropriate constant region reverse primers were therefore used to amplify from the constant regions. PCR amplification was carried out with 12 mouse VH region-specific 5' primers and 3' primers specific for previously determined antibody subclass with a hot-start Taq polymerase for 35 cycles (94° C., 5 min followed by 35 cycles of 94° C./1 min, 60° C./1 min, 72° C./2 min; final polishing step of 20 min at 72° C.).

Amplified products were assessed by agarose gel electrophoresis. Positive amplifications resulted for the VH4 primer.

Light (κ) Chain Variable Region PCRs:

Immunoglobulin light chain variable region usage was determined using PCR with a previously published set of primers [60]. Previous results using a mouse mAb isotyping test kit had indicated that both FG88.2 and FG88.7 used κ light chains. PCR amplification was carried out with mouse Vκ region-specific 5' and 3' mouse Cκ specific primers with a hot-start Taq polymerase for 35 cycles (94° C., 5 mins followed by 35 cycles of 94° C./1 min, 60° C./1 min, 72° C./2 mins; final polishing step of 20 mins at 72° C.). Amplification products were assessed by agarose gel electrophoresis. Positive amplifications resulted with the Vκ1 and Vκ2 primers for both FG88.2 and FG88.7.

PCR Product Purification and Sequencing:

PCR products were purified using a Qiaquick PCR purification kit (Qiagen, Crawley, UK). The concentration of the resulting DNA was determined by Nanodrop and the purity assessed by agarose gel electrophoresis. PCR products were sequenced using the originating 5' and 3' PCR primers at the University of Nottingham DNA sequencing facility (see, nottingham.ac.uk/life-sciences/facilities/dna-sequencing/index.aspx). Sequences were analysed (V region identification, junction analysis) using the IMGT database search facility (see imgt.org/IMGT_vquest/vquest?livret=0&Option=mouseIg). Sequencing indicated that FG88.2 and FG88.7 shared near identical heavy and light chain variable regions (heavy chain; IGHV5-12*02, IGHJ3*01, light chain; IGKV1-117*01, IGKJ4*01). Sufficient residual constant region was present in the heavy chain sequences to confirm that FG88.2 and FG88.7 were of the mIgG3 subclass, indicating clearly that the two clones had come from two independent splenocyte-NSO fusion events.

Cloning Strategy:

Direct cloning of the PCR products into the pDCOrig-hIgG1 vector using the restriction sites incorporated into the PCR primers was known to be relatively inefficient from previous Scancell experience. A dual cloning strategy was therefore adopted; the PCR product generated using a proof-reading polymerase was cloned into both pDCOrig-hIgG1 and a TA vector (pCR2.1; Invitrogen) simultaneously, with the TA vector-cloned product acting as an easily expanded backup source of material for cloning should the initial pDCOrig-hIgG1 cloning fail.

FG88.7 Heavy/Light Chain PCR for Cloning:

PCR amplification was carried out using a proof-reading polymerase (Phusion; NEB) and the cloning primers described above using the FG88.7 cDNA template previously described for 35 cycles (98° C., 3 min followed by 35 cycles of 98° C./30 sec, 58° C./30 sec, 72° C./45 sec; final polishing step of 3 min at 72° C.). Successful amplification was confirmed by agarose gel electrophoresis.

Method 1—Direct Light Chain Cloning:

Amplified FG88.7 light chain was digested sequentially with the restriction enzymes BsiWI and BamHI according to manufacturer's instructions (NEB). Vector (pDCOrig-hIgG1, containing V regions from a previously cloned antibody) was simultaneously digested. Vector DNA was agarose gel purified using a QIAquick gel extraction kit (Qiagen) and insert DNA purified using a PCR purification kit. After DNA quantification by Nanodrop, vector DNA was phosphatase treated according to manufacturer's recommendations (Antarctic Phosphatase, NEB) and light chain insert ligated into the vector (T4 DNA ligase, NEB). Ligated DNA was transformed into chemically competent TOP10F' cells (Invitrogen) and spread on 35 μg/ml Zeocin (Invitrogen, Toulouse, France) supplemented LB agar plates which were then incubated overnight at 37° C.

Method 2—TOPO Light Chain Cloning:

Amplified FG88.7 light chain was treated with Taq polymerase (NEB) for 15 min at 72° C. to add 'A' overhangs compatible with TA cloning. Treated PCR product was incubated with the TOPO TA vector pCR2.1 (Invitrogen) and transformed into chemically competent TOP10F' cells according to manufacturer's instructions. Transformed bacteria were spread on ampicillin (80 μg/ml) supplemented LB agar plates which were then incubated overnight at 37° C. Colonies were grown in liquid culture (LB supplemented with 80 μg/ml ampicillin) and plasmid DNA prepared (spin miniprep kit, Qiagen). Presence of an insert was confirmed by sequential digestion with BsiWI and BamHI and agarose gel electrophoresis. Sequencing was carried out on miniprep DNA from colonies using T7 and M13rev primers. The DNA insert from one such colony had the predicted FG88.7 light chain sequence; a 300 ml bacterial LB/ampicillin culture was grown overnight and plasmid DNA prepared by maxiprep (plasmid maxi kit, Qiagen). Maxiprep DNA insert was confirmed by sequencing.

TOPO Heavy Chain Cloning:

Amplified FG88.7 heavy chain was treated with Taq polymerase (NEB) for 15 mi at 72° C. to add 'A' overhangs. Treated PCR product was incubated with the TOPO TA vector pCR2.1 and transformed into chemically competent TOP10F' cells as above. Transformed bacteria were spread on ampicillin supplemented LB agar plates which were then incubated overnight at 37° C. Colonies were grown in liquid culture (LB/ampicillin) and plasmid DNA prepared (spin miniprep kit). Presence of an insert was confirmed by digestion with HindIII and AfeI and agarose gel electrophoresis. Sequencing was carried out on miniprep DNA from a number of colonies using T7 and M13rev primers. The DNA insert from one such colony had the predicted FG88.7 heavy chain sequence; a 300 ml bacterial LB/ampicillin culture was grown overnight and plasmid DNA prepared by maxiprep (plasmid maxi kit, Qiagen). Maxiprep DNA insert was confirmed by sequencing.

pDCOrig-hIgG1 Double Expression Vector Light Chain Cloning:

The FG88.7 light chain was digested from the TOPO vector pCR2.1 by sequential digestion with BsiWI and BamHI and the 400 bp insert DNA agarose gel purified using a QIAquick gel extraction kit (Qiagen) following manufacturer's recommendations. This insert was ligated into previously prepared pDCOrig-hIgG1 vector (see above) and transformed into chemically competent TOP10F' cells. Transformations were spread on 35 μg/ml Zeocin supplemented LB agar plates which were then incubated overnight at 37° C. Colonies were grown in liquid culture (LB supplemented with 35 μg/ml Zeocin) and plasmid DNA prepared (spin miniprep kit, Qiagen). Sequencing was carried out on miniprep DNA from all colonies using the P6 sequencing primer sited in the human kappa constant region. The DNA insert from a colony had the predicted FG88.7 light chain sequence correctly inserted in pDCOrig-hIgG1; a 300 ml bacterial LB/zeocin culture was grown overnight and plasmid DNA prepared by maxiprep (plasmid maxi kit, Qiagen).

pDCOrig-hIgG1 Double Expression Vector Heavy Chain Cloning:

The FG88.7 heavy chain insert was digested from the TOPO vector pCR2.1 by digestion with HindIII and AfeI. Vector (pDCOrig-hIgG1-27.18 k) containing the FG88.7 kappa light chain (prepared above) was also digested with HindIII and AfeI. The vector DNA was then phosphatase treated according to manufacturer's recommendations (Antarctic Phosphatase, NEB). After agarose gel electrophoresis, the 6.5 kb pDCOrig-hIgG1 vector band and 400 bp FG88.7H insert band were isolated using a QIAquick gel extraction kit (Qiagen) following manufacturer's recommendations. The insert was ligated into the pDCOrig-hIgG1 vector and transformed into chemically competent TOP10F' cells. Transformations were spread on 35 µg/ml Zeocin supplemented LB agar plates which were then incubated overnight at 37° C. Colonies were grown in liquid culture (LB supplemented with 35 µg/ml Zeocin) and plasmid DNA prepared (spin miniprep kit, Qiagen). Presence of an insert was confirmed by digestion with HindIII and AfeI and agarose gel electrophoresis. Sequencing was carried out on miniprep DNA from a number of the colonies using the P3rev sequencing primer sited in the human IgG1 constant region. The DNA insert from one of the colonies had the predicted FG88.7 heavy chain sequence correctly inserted in pDCOrig-hIgG1; a 300 ml bacterial LB/zeocin culture was grown overnight and plasmid DNA prepared by maxiprep (plasmid maxi kit, Qiagen). Sequencing was used to confirm that both heavy and light chain loci.

Expression, Purification and Characterisation of the Chimeric Antibody Constructs;

The methodology for the expression and purification of chimeric antibody described in the present invention can be achieved using methods well known in the art. Briefly, antibodies can be purified from supernatant collected from transiently, or subsequently stable, transfected cells by protein A or protein G affinity chromatography based on standard protocols, for example Sambrook et al. [61].

Immunohistochemistry Assessment for FG88:

To determine the therapeutic value of FG88, it was screened on gastric, ovarian, colorectal cancer tissue microarrays by immunohistochemistry (IHC).

Methodology: Immunohistochemistry was performed using the standard avidin-biotin peroxidise method. Paraffin embedded tissue sections were placed on a 60° C. hot block to melt the paraffin. Tissue sections were deparaffinised with xylene and rehydrated through graded alcohol. The sections were then immersed in 500 ml of citrate buffer (pH6) and heated for 20 min in a microwave (Whirlpool) to retrieve antigens. Endogenous peroxidase activity was blocked by incubating the tissue sections with endogenous peroxidase solution (Dako Ltd, Ely, UK) for 5 min. Normal swine serum (NSS; Vector Labs, CA, USA; 1/50 PBS) was added to each section for 20 min to block non-specific primary antibody binding. All sections were incubated with Avidin D/Biotin blocking kit (Vector Lab) for 15 min each in order to block non-specific binding of avidin and biotin. The sections were re-blocked with NSS (1/50 PBS) for 5 mins. Then tissue sections were incubated with primary antibody at room temperature for an hour. Anti-β-2-microglobulin (Dako Ltd; 1/100 in PBS) mAb and PBS alone were used as positive and negative controls respectively. Tissue sections were washed with PBS and incubated with biotinylated goat anti-mouse/rabbit immunoglobulin (Vector Labs; 1/50 in NSS) for 30 min at room temperature. Tissue sections were washed with PBS and incubated with preformed 1/50 (PBS) streptavidin-biotin/horseradish peroxidase complex (Dako Ltd) for 30 min at room temperature. 3, 3'-Diaminobenzidine tetra hydrochloride (DAB) was used as a substrate. Each section was incubated twice with 100 µl of DAB solution for 5 min. Finally, sections were lightly counterstained with haematoxylin (Sigma-Aldrich, Poole Dorset, UK) before dehydrating in graded alcohols, cleaning by immersing in xylene and mounting the slides with Distyrene, plasticiser, xylene(DPX) mountant (Sigma).

Confocal Microscopy:

FG88.2 and FG88.7 mAbs were labelled with Alexa-488 fluorophore (A-FG88.2 and A-FG88.7) according to manufacturer's protocol (Invitrogen). $1.5 \times 10^5$ C170 cells were grown on sterile circular coverslips (22 mm diameter, 0.16-0.19 mm thick) in 6 well plate for 24 hr in 5% $CO_2$ at 37° C. 24 hours later, cells on coverslips were treated with 5 µg/ml of A-FG88.2 and A-FG88.7 mAbs for 2 hr at 37° C. in dark. 2 hours later, excess/unbound mAbs were washed away using PBS. The cells were then fixed using 0.4% paraformaldehyde for 20 min in dark. 0.4% paraformaldehyde was washed away using PBS. The coverslips were mounted to slides with PBS:glycerol (1:1). The coverslip edge was sealed with clear nail varnish. Localisation of the A-FG88.2 and A-FG88.7 mAbs was visualised under a confocal microscope (Carl Zeiss, Jena, Germany).

ADCC and CDC:

Cells ($5 \times 10^3$) were co-incubated with 100 µl of PBMCs, 10% autologous serum or media alone or with mAbs at a range of concentrations. Spontaneous and maximum releases were evaluated by incubating the labeled cells with medium alone or with 10% Triton X-100, respectively. After 4 hr of incubation, 50 µl of supernatant from each well was transferred to 96 well lumaplates. Plates were allow to dry overnight and counted on a Topcount NXT counter (Perkin Elmer, Cambridge, UK). The mean percentage lysis of target cells was calculated according to the following formula:

$$\text{Mean \% lysis} = 100 \times \frac{\text{mean experimental counts} - \text{mean spontaneous counts}}{\text{mean maximum counts} - \text{mean spontaneous counts}}$$

[3H] Thymidine Incorporation Assay:

Cancer cells ($1 \times 10^3$/well) were incubated on a 96-well flat bottom microtitre plate for 24 hours to establish an adherent monolayer. Next day, mAbs were added 100 µl/well in quadruplicate (0.003 µg/ml to 3 µg/ml) in the presence or absence of 20 µM of a pan-caspase inhibitor Z-FMK-VAD (carbobenzoxy-valyl-alanyl-aspartyl-[O-methyl]-fluoromethylketone; Promega, Eastleigh, UK) for 48 hours. Cells were then exposed to 0.5 µCi/well of $^3$H-thymidine during the final 24 hours of the 48-hour period. The incorporation of $^3$H-thymidine into cells of the culture was measured using a liquid scintillation counter (Microscint 0 liquid scintillant on a Topcount NXT, both Perkin Elmer).

PI Uptake Assay:

FG88.2 and FG88.7 were incubated with C170 cells and tested for uptake of the small molecular weight dye propidium iodide (PI, Sigma) at various temperatures. Tumour cells ($5 \times 10^4$) were incubated on a 96-well round bottom microtitre plate with 50 µl of primary antibodies at 37° C. or 4° C. for 2 hr. 1 µg of PI was added and cells were incubated at 37° C. or 4° C. for 30 min. 0.4% formaldehyde was used to fix the cells. Samples were analysed on a FC-500 flow cytometer (Beckman Coulter). To analyse and plot raw data WinMDI 2.9 software was used. For comparison, mAb 505/4 which is known to induce membrane damage was also included. Medium alone was included as a negative control.

Dextran Uptake Assay:

FG88.2 mAb was incubated with C170 cells and tested for uptake of fluorochrome-labelled 3 KDa and 40 KDa molecular weight dextran (Invitrogen) at 37° C. Tumour cells ($5 \times 10^4$) were incubated on a 96-well flat bottom microtitre plate with 50 μl of primary antibodies at 37° C. for 2 hr. 1 μg of dextran was added and cells were incubated at 37° C. for 30 min. For comparison, 0.5% $H_2O_2$ and 0.4% saponin, which are known to induce membrane damage, were also included. Medium alone (RPMI) was included as a negative control. Samples were analysed on a MACSQ flow cytometer (Miltenyi Biotech) using MACSQ software.

DNA Fragmentation:

C170 or Jurkat cells ($1.25 \times 10^6$) were incubated with 30 μg/ml of FG88.2 or FG88.7 or 0.5 μg/ml of anti-Fas (Promega) mAbs in the presence or absence of the pan-caspase inhibitor Z-FMK-VAD (20 μM final concentration) at 37° C. 20 hours later, cells were collected by centrifugation at 14,000 rpm for 5 min at room temperature. Cell pellets were resuspended gently in 500 μl of lysis buffer (10 mM Tris-HCL pH8.5, 5 mM EDTA, 200 mM NaCl, 0.5% SDS, all Sigma) and incubated at 60° C. for 5 min. RNAse was added to each sample (Sigma; final concentration of 4 μg/ml) and incubated at 37° C. for 15 min. Proteinase K was added to each sample (Active Motif, La Hulpe, Belgium; final concentration of 2 ng/ml) and incubated at 60° C. for 1 hr. 350 μl of 5M NaCl was added to each sample and incubated on ice for 5 min. Samples were spun at 14,000 rpm for 15 min at 4° C. Supernatants were collected and an equal volume of ice cold phenol:chloroform (1:1 v/v) was added to each sample. Samples were spun at 14,000 rpm for 5 min at 4° C. The aqueous phase of each sample was collected and 20 μl of sodium acetate, pH 5.2 (Sigma; final concentration of 120 mM) was added to each sample. 500 μl of 100% ethanol (pre-chilled to −20° C.) was added to each sample and incubated at −80° C. for 1 hr. Samples were spun at 14,000 rpm for 10 min at 4° C. Supernatants were discarded and pellets were washed with 500 μl of pre-chilled 70% ethanol. Samples were spun at 14,000 rpm for 10 min at 4° C. Supernatants were removed, DNA pellets were allowed to air dry, resuspended in 20 μl of 10 mM Tris/HCl, pH8.5 buffer and analysed on a 0.8% agarose gel.

Scanning Electron Microscopy:

C170 cells ($1 \times 10^5$) were grown on sterile circular coverslips (13 mm diameter, 0.2 mm thick; Thermanox, Nunc, Roskilde, Denmark) in a 6 well plate at 37° C., 5% $CO_2$. 24 hours later, cells on coverslips were treated with 30 μg/ml of FG88.2 and FG88.7 mAbs, medium alone, 0.5% $H_2O_2$ and 0.4% saponin (Sigma) for 20 hours at 37° C. 20 hours later, cells were washed with pre-warmed 0.1M sodium cacodylate buffer (pH7.4). Then washed cells were fixed with pre-warmed glutaraldehyde (final concentration of 12.5% w/v) for 24 hr. Fixed cells were washed twice with 0.1M sodium cacodylate buffer and post-fixed with 1% osmium tetroxide (pH 7.4) for 45 min. Subsequently, the cells were washed twice with deionised water. After the final wash, the cells were dehydrated in increasing concentration of ethanol from 40% to 100%. The prepared cells were exposed to critical point drying then sputtered with gold prior to SEM analysis (JSM-840 SEM, JEOL).

In Vivo Model:

The study was conducted under a UK Home Office Licence. NCRI guidelines for the welfare and use of animals in cancer research, LASA good practice guidelines and FELAS working group on pain and distress guidelines was also followed. Endotoxin free (<10 EU/ml) FG88 mAb was supplied in pre-formulated aliquots ready for dosing and stored at −20° C. until use. Age matched male MF-1 nude mice were obtained from Harlan Laboratories (Bichester, UK) with each group, FG88, control mAbs or the vehicle control, consisting of n≥8 animals.

Mice were implanted with C170HM2 DLuX cells and monitored by optical imaging to determine tumour establishment and suitability to be entered into the study. Mice were dosed with either FG88 or the positive control mAb, 505/4 (1 mg/ml) dosed at 0.1 mg 2× weekly 100 μl intravenously (i.v.) until termination, or PBS, the vehicle control for the mAb, 100 μl 2× weekly i.v. until termination. Weekly bioluminescent imaging was carried out on all mice to obtain pre and post dosing tumour measurements. In this way each mouse provided pre-dose control readings against which tumour growth could be compared.

All measurements and readouts were transferred from the original dictation/notation to excel (tab delineated) format for data processing in SPSS v16.0. Data integrity was checked using explore and descriptive functions. Erroneous points when identified were cross referenced against the original data and corrected accordingly. The data was screened for outliers and distribution profile; data-points falling outside the 95% confidence limit (outliers) were removed from analysis, but kept in the datasheet for reference purposes.

Mice were imaged weekly for bioluminescent tumour burden (BLI) over the duration of the study as follows; 60 mg/kg D-Luciferin substrate was administered subcutaneously (s.c.), the mice were anesthetised and BLI readings taken 15 mins post substrate administration on open filter block (2D) and sequential emission filters (for DLIT, 3D reconstruction). Ventral and dorsal imaging was undertaken; the optimum position for imaging was abdomen uppermost. BLI was measured over the entire abdominal area, one Region of Interest (ROI) for each mouse in order to include all lesions present. Each mouse had a pre-dosing or baseline image taken to allow calculation of percentage tumour growth over time; these data were averaged per group. BLI readings were also taken after termination to identify tumours in PM tissue.

Example 1

Generation and Initial Characterisation of FG88 mAbs

FG88 was raised by immunisation with glycolipid antigens from the colorectal cell line, Colo205.

Analysis of antibody response to immunisations: Antibody titres were initially monitored by lipid enzyme-linked immunosorbent assay (ELISA). Thin layer chromatography (TLC) analysis using Colo205 total and plasma membrane lipid extracts, flow cytometry analysis (FACS) using Colo205 tumour cells and Western blot using Colo205 whole cell extract, total and plasma membrane lipid extracts were subsequently performed. The mouse considered to have the best response, compared to the pre-bleed serum control was boosted intravenously (i.v.) with Colo205 plasma membrane lipid extract prior to fusion.

8 days after fusion, supernatants were collected and screened against fresh Colo205 tumour cells. Hybridomas which demonstrated cell surface binding, using an indirect immunofluorescence assay, were harvested, washed in complete media and spread across 96 well plates at 0.3 cells per well to acquire a clone. The plate was then screened for positive wells and these grown on until a sufficient number of cells was obtained to spread across a 96 well plate at 0.3 cells per well for a second time. If the resulting number of colonies equalled ~30 and all hybridomas were positive, the hybridoma was considered a clone. Methods for clonal expansion, bulk culture and antibody purification of antibodies or antibody fragments are available using conventional techniques known to those skilled in the art.

Figure 3B:
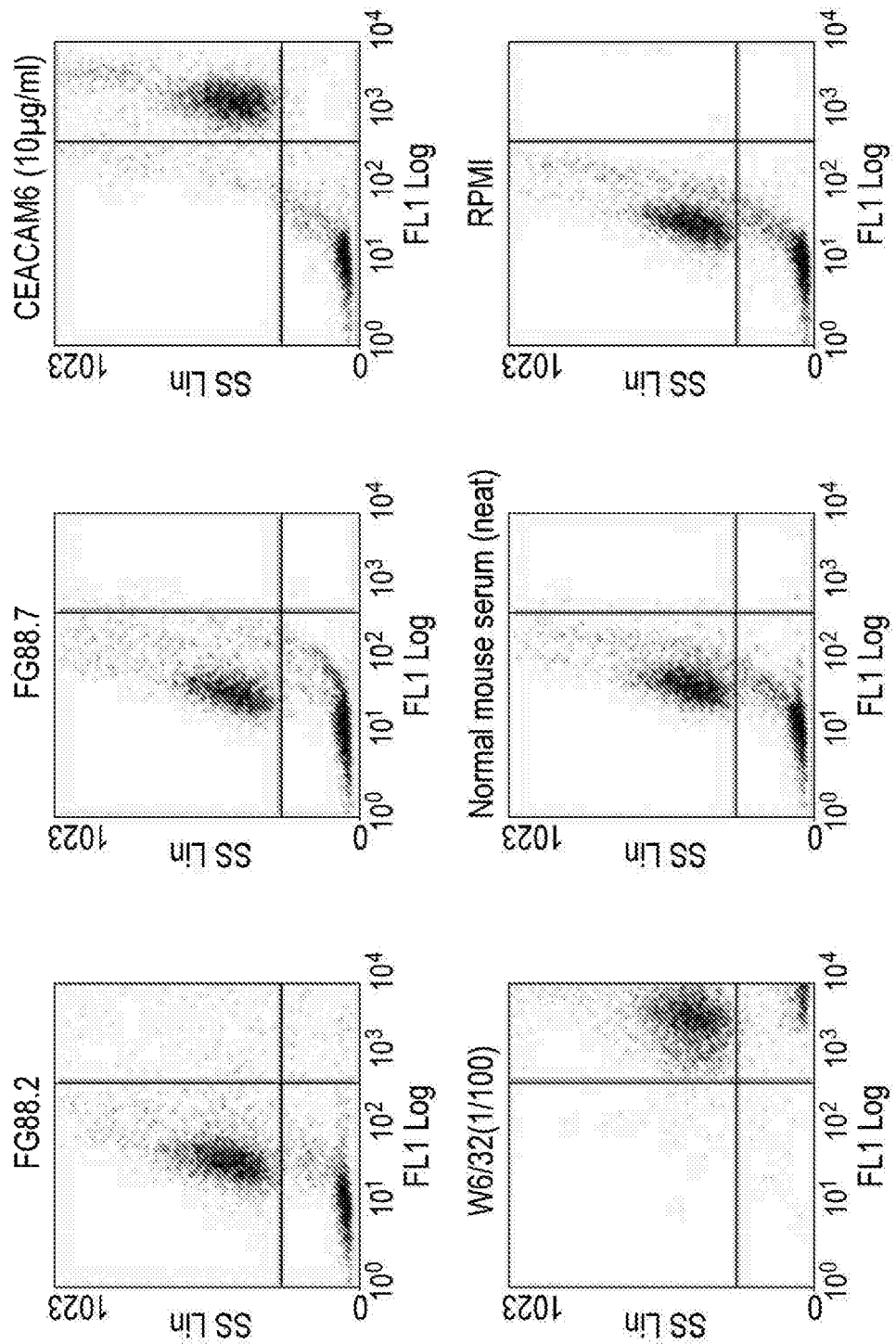
FIG. 3b: Assessment of FG88 hybridoma supernatant binding to healthy donor blood by indirect immunofluorescence staining and flow cytometric analysis. The CEACAM6 (anti-CEACAM6; binds granulocytes; 10 µg/ml) and W6/32 (anti-HLA-A,B,C; 5 µg/ml) mAbs are included as positive controls and normal mouse serum and medium alone (RPMI), as the negative.
Figure 3C:
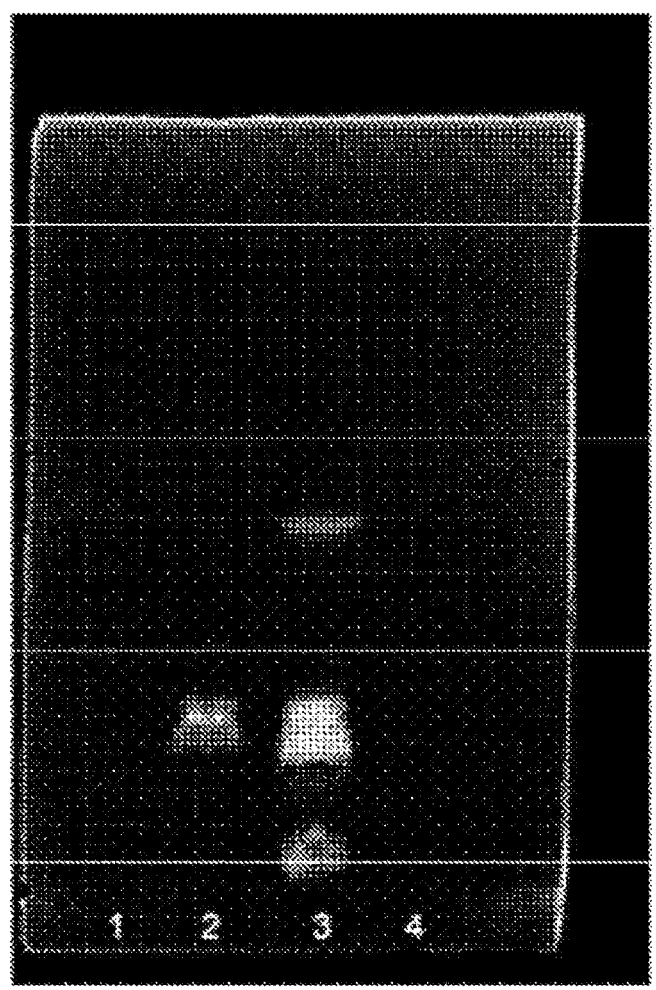
FIG. 3c: Binding of FG88.2 hybridoma supernatant to lipid antigens as assessed by thin layer chromatography (TLC). FG88.2 hybridoma supernatant (1/20 dilution) binding lipid antigens of 1) AGS (total lipid extract from $2\times10^6$ cells), 2) C170 (total lipid extract from $2\times10^6$ cells), 3) Colo205 (total lipid extract from $2\times10^6$ cells) or, 4) the chloroform methanol control.

Binding of FG88 hybridoma supernatant to Colo205 cells: FG88.2 and FG88.7 were analysed for their ability to bind to Colo205 cells by indirect immunofluorescence and FACS analysis (FIG. 3a). Both hybridomas bound with strong intensity to the cell surface of Colo205 cells (FG88.2 Gm 4539; FG88.7 Gm 2897) when compared to positive control mAb anti-HLA mAb W6/32 (eBioscience, CA, USA), and the negative controls of and isotype control In contrast, FG88.2 and FG88.7 hybridoma supernatants did not bind to any normal blood cells (FIG. 3b). FG88.2 bound lipid antigens from C170 and Colo205 but not those from AGS (ATCC accession # CRL-1739; FIG. 3c).

Example 2

Defining the Epitopes Recognised by FG88 mAbs

Figure 4A:
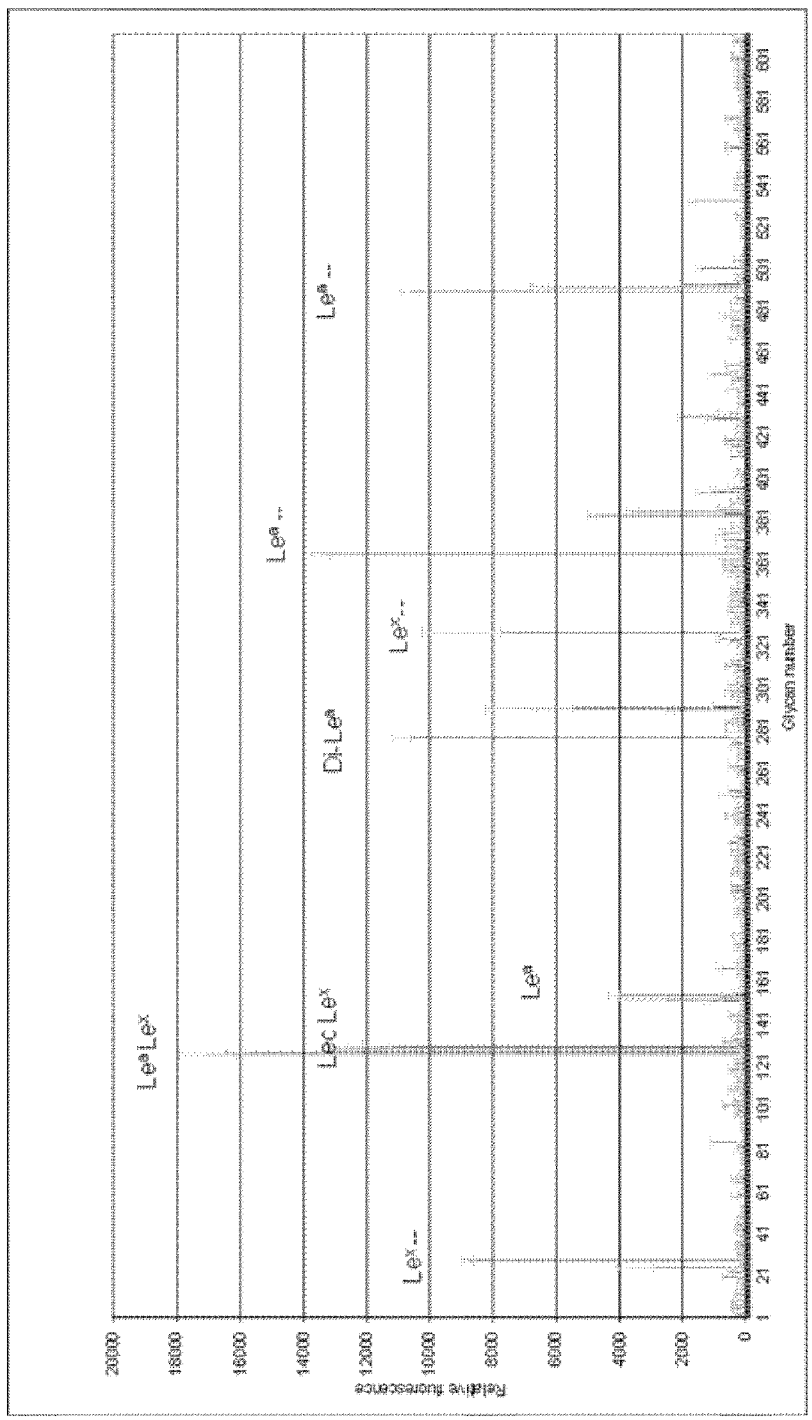
FIG. 4: Binding of FG88.2 and FG88.7 were screened against The Consortium for Functional Glycomics glycan array which is composed of 610 mammalian glycan targets. The fine specificity between (a) FG88.2 and (b) FG88.7 are compared; where $Le^a$=Lewis$^a$, $Le^x$=Lewis$^x$, $Le^a$--=Lewis$^a$ containing glycan and $Le^x$--=Lewis$^x$ containing glycan. The corresponding details of glycans bound are shown where ■ represents glucosylamine, represents galactose, ▲ represents fucose, and ● represents mannose. Sp denotes the length of spacer between glycan and slide.
Figure 4B:
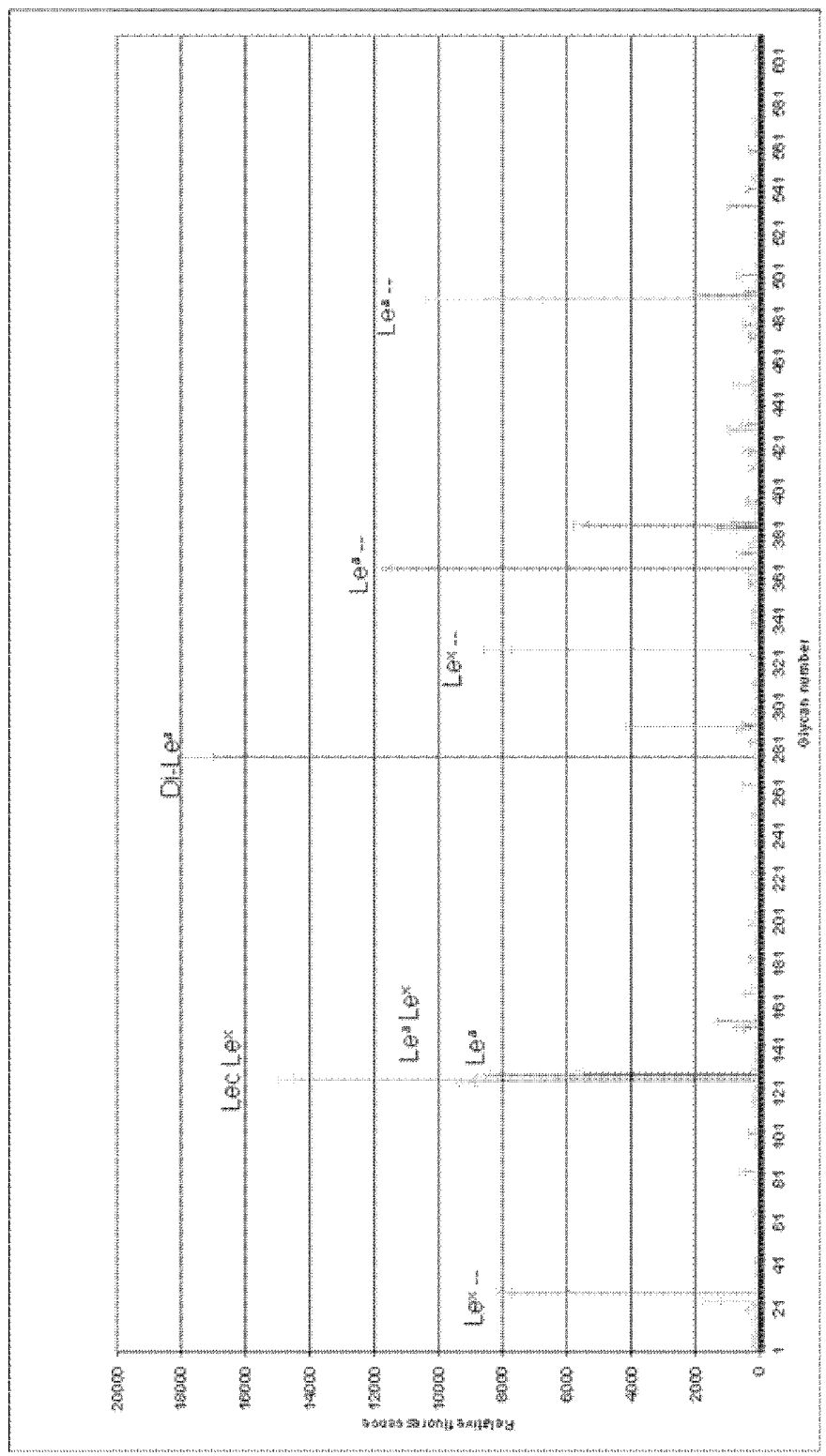

To clarify the fine specificities of the FG88 mAbs, they were screened against ≥600 natural and synthetic glycans. Binding of FG88.2 and FG88.7 mAbs to the glycan array showed that both mAbs bound to LecLe$^x$, Le$^a$Le$^x$, Le$^x$ containing glycan, Le$^a$ containing glycans, Le$^a$ and Di-Le$^a$ (FIG. 4a,b). Subtle differences were observed between the two antibodies with FG88.2 binding most strongly to LecLe$^x$ and Le$^a$Le$^x$, followed Le$^a$ containing glycan, Le$^a$, Di-Le$^a$ and Le$^x$ containing glycan. FG88.7 bound most strongly to LecLe$^x$ and Di-Le$^a$, followed by Le$^a$ containing glycans, Le$^a$Le$^x$ and Le$^x$ containing glycan.

Additionally, the mAbs bound simple Le$^a$ on the array but not Le$^c$ or Le$^x$. This was corroborated by competition experiments where preincubation of both mAbs with a Le$^a$-HSA conjugate, but not a Le$^x$-HSA conjugate, abolished Colo205 binding (data not shown). The Le$^a$-HSA binding kinetics of the mAbs was examined using SPR (Biacore X). Fitting of the binding curves revealed strong apparent functional affinity (Kd ~$10^{-10}$ M) with fast association (~$10^5$ l/Ms) and slow dissociation (~$10^{-5}$ l/s) rates for both mAbs.

TABLE 1

Determination of kinetic Le$^a$-binding parameters by SPR.

| mAb | Association rate $k_{on}$ (1/Ms) | Dissociation rate $k_{off}$ (1/s) | Equilibrium dissociation constant Kd (M) |
|---|---|---|---|
| FG88.2 | $1.9 \times 10^5$ | $11.8 \times 10^{-5}$ | $6.3 \times 10^{-10}$ |
| FG88.7 | $1.7 \times 10^5$ | $5.8 \times 10^{-5}$ | $3.4 \times 10^{-10}$ |

Figure 5:
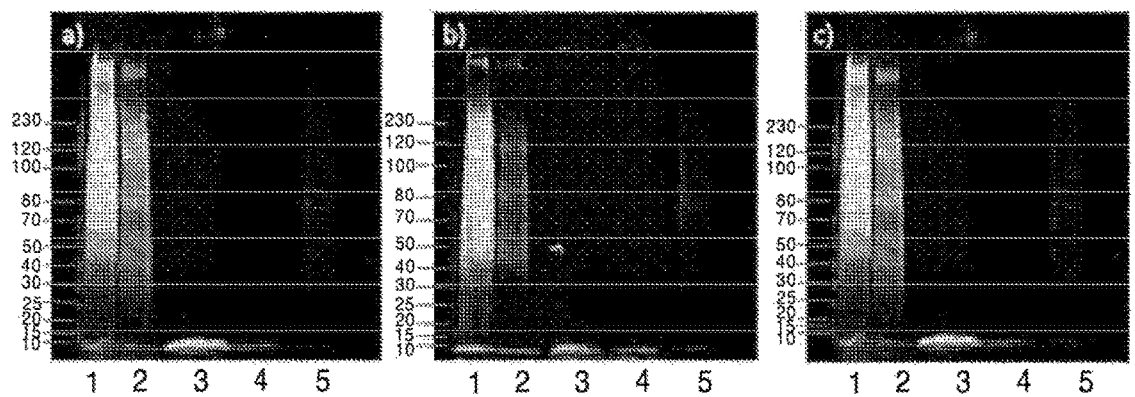
FIG. 5: Binding of FG88.2 and FG88.7 to protein and lipid antigens as assessed by Western blot analysis. Lanes 1) Colo205 cell lysates ($1\times10^5$ cells equivalent), 2) Colo205 plasma membrane ($1\times10^6$ cells equivalent), 3) Colo205 total lipid extract ($1\times10^6$ cells equivalent), 4) Colo205 plasma membrane lipid extract ($1\times10^6$ cells equivalent) and 5) C170 cell lysates ($1\times10^5$ cells equivalent) using a) FG88.2 (5 µg/ml) b) FG88.7 (5 µg/ml) and c) 505/4 (5 µg/ml).

To confirm that these sugars were expressed on proteins from tumour cells, FG88 mAbs were screened for binding to glycoproteins by SDS-PAGE/Western blotting (FIG. 5). FG88.2 and FG88.7 recognise low, intermediate (MW between 10-230 kDa) and high (molecules that do not enter the separation gel) molecular weight molecules by Western blot analysis of Colo205 whole cell extract, C170 whole cell extract, Colo205 plasma membrane, Colo205 plasma membrane lipid and total lipid extracts. FG88.2 and FG88.7 also recognised a band at the dye front in Colo205 total lipid extract and Colo205 plasma membrane lipid extract lanes which is presumed to be glycolipid. The mAb 505/4 recognising sialyl-di-Le$^a$ was included as positive control and demonstrated a similar blotting pattern to FG88.2 and FG88.7, recognising high, intermediate and low molecular weight proteins and the glycolipid band at the dye front.

Figure 6:
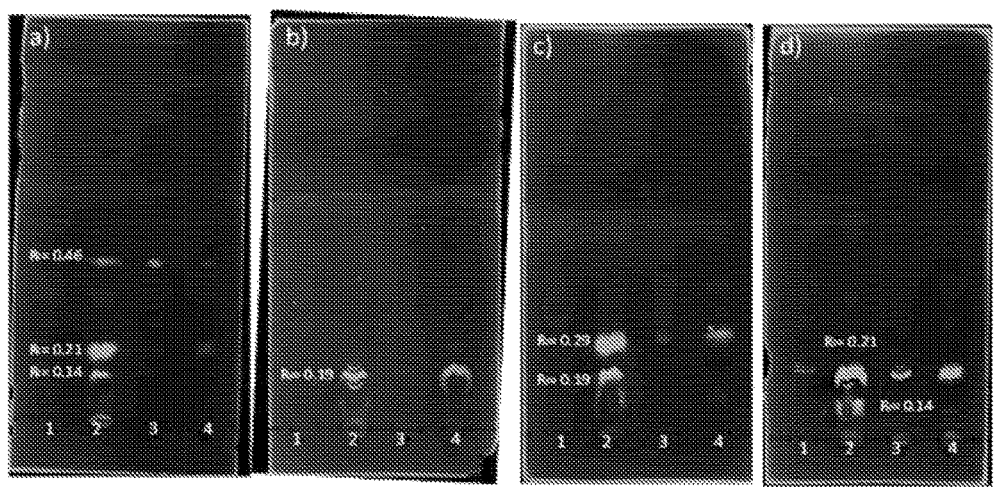
FIG. 6: Binding of FG88.2 and FG88.7 to lipid antigens as assessed by TLC. Total lipid extracts from 1) AGS, 2) Colo205, 3) MKN45 and 4) C170 tumour cells (each $2\times10^6$ cells equivalent) using a) FG88.2 (5 μg/ml), b) 505/4 (5 μg/ml), c) FG88.7 (5 μg/ml) and d) CA19-9 (5 μg/ml). The 505/4 and CA19-9 mAbs were included in the panel for comparison.

To confirm that LecLe$^x$, Le$^a$Le$^x$, Le$^a$ containing glycans, Le$^a$ and Di-Le$^a$ glycans are expressed on lipids, the mAbs were screened for binding to tumour associated lipids by thin layer chromatography (TLC). FG88.2 mAb bound lipid antigens from Colo205, MKN45 (ATCC accession # CCL-171) and C170 but not those from AGS (FIG. 6). Two glycolipids were stained by FG88.2 in Colo205 cells ($R_f$=0.21 and 0.14). In addition, FG88.2 stained another glycolipid with less polarity ($R_f$=0.46). In contrast, although FG88.7 also bound the same tumour cell lines as FG88.2, one of the glycolipids stained in the Colo205 sample demonstrated an intermediate mobility ($R_f$=0.19). FG88.7 also stained an extra glycolipid with less polarity ($R_f$=0.29).

Example 3

Immunohistochemistry Assessment for FG88.

To determine the therapeutic value of FG88, it was screened on colorectal, gastric, pancreatic, lung, ovarian and breast tumour tissue microarrays (TMAs) by immunohistochemistry (IHC).

To assess the binding of FG88 to human tissues, a number of tumour TMAs were stained; 69% of colorectal ($142/208$), 56% of gastric ($52/93$), 74% of pancreatic ($658/890$), 23% of lung ($62/275$), 31% of ovarian ($58/186$) and 27% of breast ($241/902$) tumour tissues were stained (Table 2). Whilst FG88 recognised only 27% of the 902 breast tumour tissues stained, 34% were triple negative breast cancer (TNBC) and 32% of tumours with a basal phenotype stained. Further, the staining of the ER negative breast TMA using FG88.2 at 0.3 ug/ml (staining for FG88.7 not determined) showed 25% positive staining ($84/338$). Stained ER negative breast tissues correlated to all basal type significantly. With TNBC being such a challenging disease with the poorest prognosis of all breast cancer subtypes, and currently cytotoxic chemotherapy is the only systemic treatment option available, FG88 could provide a valued immunotherapeutic agent for this group of patients

TABLE 2

Binding of FG88.2 (0.3 μg/ml) mAb to human colorectal, gastric, pancreatic, lung, ovarian and breast tumour tissues as assessed by immunohistochemistry. Staining of these tissue microarrays were analysed via new viewer software 2010 and given a semi-quantitative score according to intensity of staining of tumour tissue. Strong staining was given a score of 3, moderate staining a score of 2, weak staining a score of 1 and a negative score of 0.

| Tumour TMA | Tissue number | Number of positive | Percent positive (%) |
|---|---|---|---|
| Colorectal | 208 | 142 | 69 |
| Gastric | 93 | 52 | 56 |
| Pancreatic | 890 | 658 | 74 |
| Lung | 275 | 62 | 23 |
| Ovarian | 186 | 58 | 31 |
| Breast (whole array) | 902 | 241 | 27 |
| Breast ER negative | 338 | 84 | 25 |

To assess the possible toxicity of mAbs FG88.2 and FG88.7, human and Cynologous monkey normal tissue TMAs were stained. For human normal tissue TMA, FG88.2 did not stain placenta, rectum, skin, adipose, heart, skeletal, bladder, spleen, brain, stomach, breast, kidney, testis, cerebellum, cervix, lung, ovary, diaphragm, uterus, duodenum and thyroid. Staining was seen against oesophagus (moderate squamous epithelium staining), gall bladder (strong columnar epithelium staining), Ileum (strong columnar mucosa staining), jejunum (weak columnar mucosa staining), liver (strong bile duct staining), thymus (weak staining), colon (strong glandular epithelium staining), tonsil (moderate squamous epithelium staining) and pancreas (moderate staining) (Table 3). FG88.7 showed the same staining pattern as FG88.2 except that it also stained normal rectum (weak glandular epithelium stainin. For the monkey normal tissue TMA, staining was seen against small intestine, skin, colon, stomach, ovary, liver and thymus for both FG88.2 and FG88.7 (data not shown).

TABLE 3

Binding of FG88 to normal human tissues as assessed by immunohistochemistry. Staining of these tissue microarrays were analysed via new viewer software 2010 and given a semi-quantitative score according to intensity of staining of tumour tissue. Strong staining was given a score of 3, moderate staining a score of 2, weak staining a score of 1 and a negative score of 0. The results for FG88 also demonstrate differential staining of specific cell types within these tissues.

| Tissue type | FG88.2 | FG88.7 |
| --- | --- | --- |
| Placenta | 0.0 | 0.0 |
| Oesophagus | 1.1 (squamous epithelium) | 0.1 |
| Rectum | 0.0 | 2.1 |
| Gall bladder | 1.3 (columnar epithelium) | 1.2 |
| Skin | 0.0 | 0.0 |
| Adipose | 0.0 | 0.0 |
| Heart | 0.0 | 0.0 |
| Skeletal | 0.0 | 0.0 |
| Bladder | 0.0 | 0.0 |
| Ileum | 3.3 (columnar mucosa) | 2.3 |
| Spleen | 0.0 | 0.0 |
| Brain | 0.0 | 0.0 |
| Jejunum | 2.1 (columnar mucosa) | 1.1 |
| Stomach | 0.0 | 0.0 |
| Breast | 0.0 | 0.0 |
| Kidney | 0.0 | 0.0 |
| Testis | 0.0 | 0.0 |
| Cerebellum | 0.0 | 0.0 |
| Liver | 1.1 (bile duct) | 1.1 |
| Thymus | 1.1 (keratin) | 1.1 |
| Cervix | 0.0 | 0.0 |
| Lung | 0.0 | 0.0 |
| Small intestine | 3.0 (intestinal epithelium) | 0.2 |
| Colon | 2.0 (glandular epithelium) | 2.0 |
| Ovary | 0.0 | 0.0 |
| Tonsils | 2.1 (squamous epithelium) | 2.1 |
| Diaphragm | 0.0 | 0.0 |
| Pancreas | 2.2 (?) | 0.1 |
| Uterus | 0.0 | 0.0 |
| Duodenum | 0.0 | 0.0 |
| Thyroid | 0.0 | 0.0 |

Example 4

Chimeric mAb

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. Chimeric (or humanised) antibodies of the present invention can be prepared based on the sequence of a murine mAb prepared as described above. The amino acid and nucleotide sequence for the variable region of the heavy (FIG. 1a) and light chains (FIG. 1b) of the FG88.2 mAb and the amino acid and nucleotide sequence for the variable region of the heavy (FIG. 2a) and light chains (FIG. 2b) of the FG88.7 mAb are shown in FIGS. 1 and 2. Numbers refer to the standardised IMGT system for the numbering of antibody sequences [59]. The CDR1, CDR 2 and CDR 3 regions are indicated. FG88.2 and FG88.7 both belong to the IGHV6-6*01 heavy chain and IGKV12-41*01 gene families. FG88.2 has 10 mutations from IGHV6-6*01 and FG88.7 eight. FG88.2 has 11 mutations from IGKV12-41*01 and FG88.7 twelve.

Figure 7:
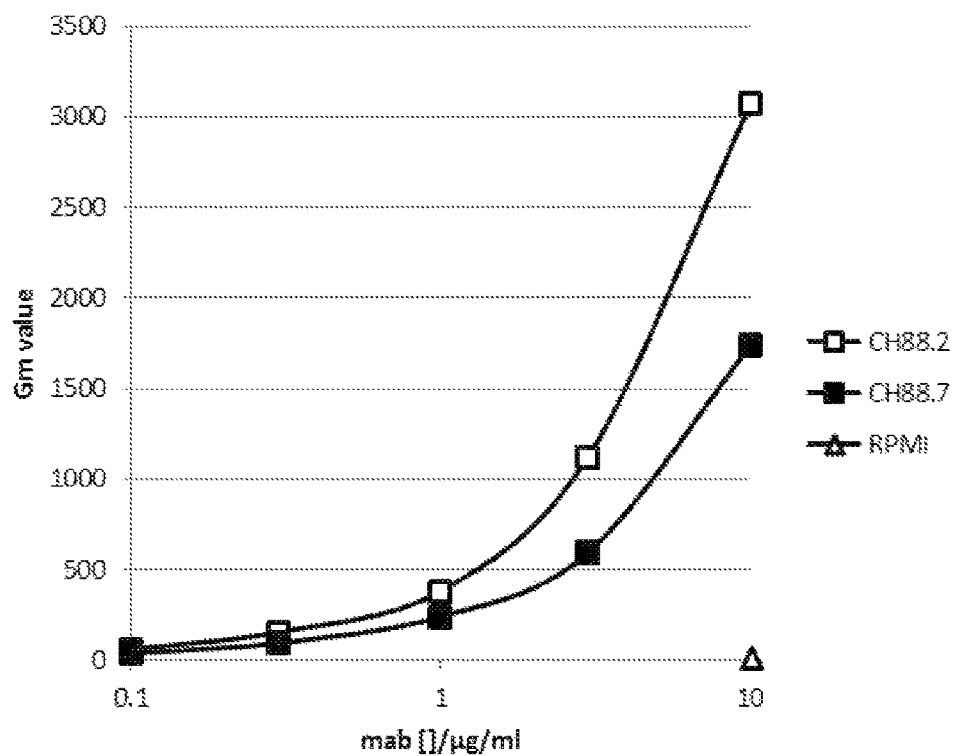
FIG. 7: Assessment of CH88.2 and CH88.7 binding to Colo205 cells by indirect immunofluorescence staining and flow cytometric analysis at a range of concentrations. $1\times10^5$ Colo205 cells were incubated with CH88.2 and CH88.7 mAbs at a range of concentrations from 0.1-10 μg/ml. Medium alone (RPMI) was used as the negative control.

FG88.2 and FG88.7 heavy and light chain variable regions were cloned into human IgG1 expression vector. This was transfected into CHO—S cells and human antibody purified on protein G. The chimeric mAbs CH88.2 and CH88.7 bound to the colorectal cell line, Colo205 (FIGS. 1c and 2c and FIG. 7). The amino acid and nucleotide sequence for the heavy (FIG. 1d) and light chains (FIG. 1e) of the human FG88.2 mAb and the amino acid and nucleotide sequence for the human heavy (FIG. 2d) and light chains (FIG. 2e) of the FG88.7 mAb are shown in FIGS. 1 and 2.

Example 5

FG88 Binding Studies

FG88.2 and FG88.7 were screened by indirect immunofluorescence staining and flow cytometric analysis for binding to the cell surface of a panel of tumour cell lines Table 4. FG88.2 bound strongly (Gm>500) to C170, Colo205, Colo201, ST16, DU4475 and Panc-1, moderately (Gm 100-500) to HT29, H69 and OVCAR-3, weakly (Gm<100) to AGS, OVCAR-4 and OAW42 and failed to bind MKN45, ASPC-1, OVCA433, MCF-7 and MDA-MB-231 cell lines. FG88.7 showed a similar binding pattern as FG88.2, except that it bound moderately to MKN45.

Figure 8A:
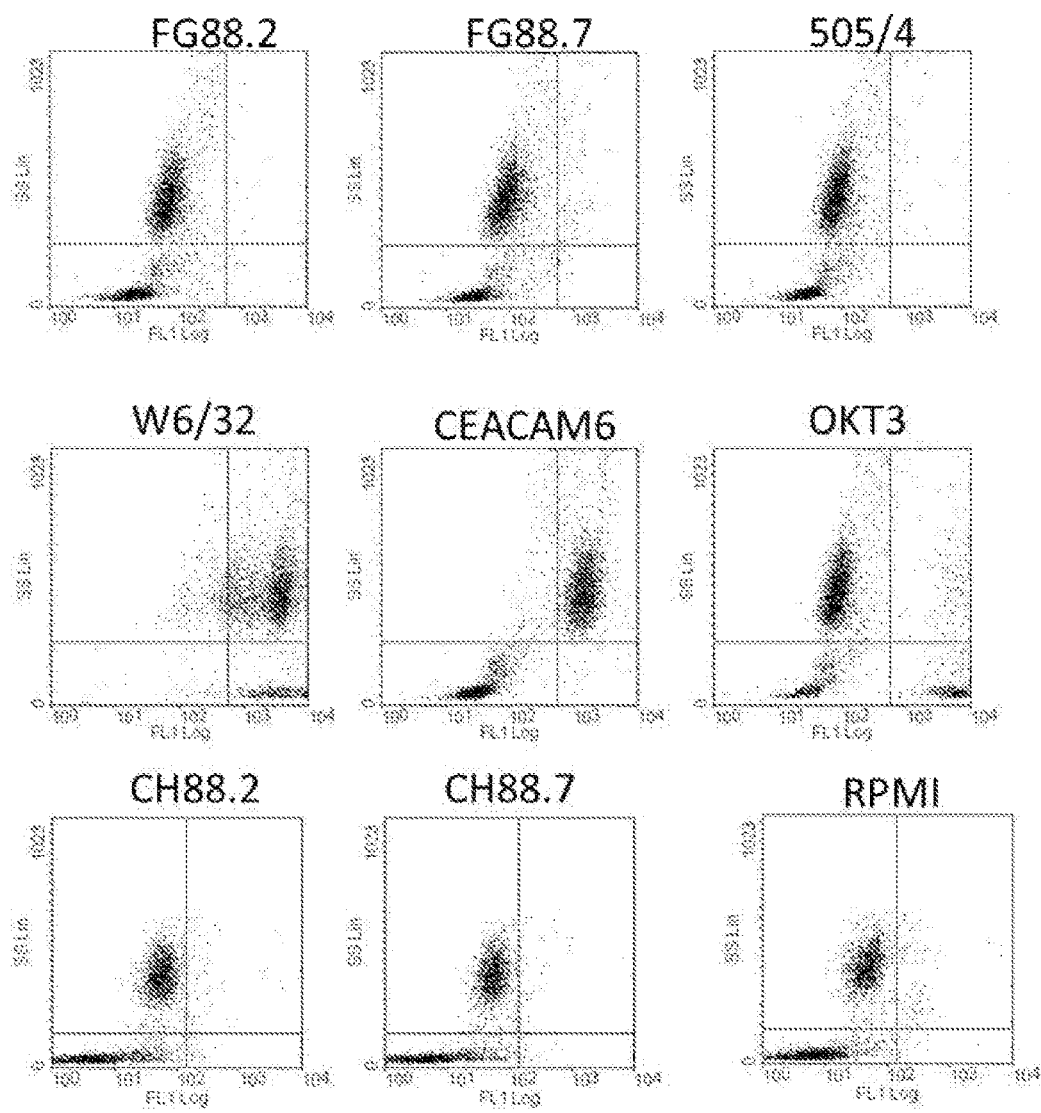
FIG. 8a: Binding of FG88.2, FG88.7, CH88.2 and CH88.7 mAbs to normal human whole blood, and the panel of comparative mAbs; 505/4, CA19-9 and 7-Le, as assessed by indirect immunofluorescence staining and flow cytometric analysis. Binding of these mAbs to normal human blood was compared to the positive controls: W6/32, anti-HLA-A,B,C mAb; CEACAM6, an anti-CEACAM6 mAb and OKT3, an anti-CD3 mAb. Mouse immunoglobulin (IgG) and medium alone (RPMI) were the negative controls
Figure 8A:
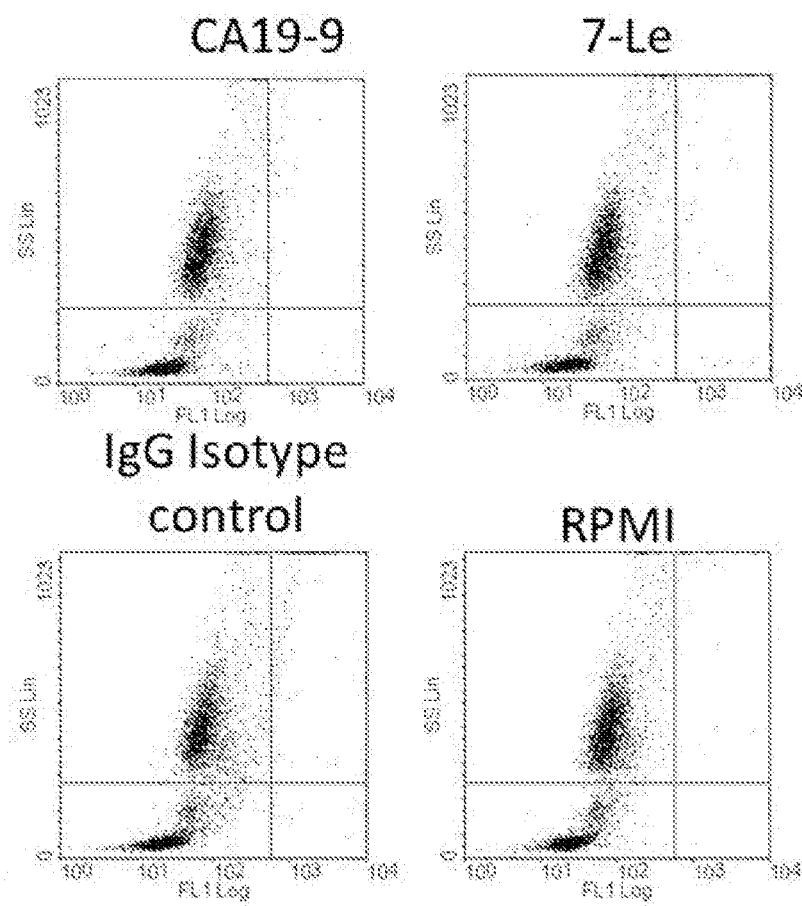

In order to establish whether binding was tumour cell specific and not cross reactive with normal blood cells, the FG88.2, FG88.7, CH88.2 and CH88.7 mAbs were incubated with healthy normal donor whole blood. Neither the murine (FG88.2 and FG88.7) nor the chimeric mAbs (CH88.2 and CH88.7) bound to peripheral blood mononuclear cells (PBMCs, lower left quadrant) or granulocytes (upper left quadrant) (FIG. 8a).

Figure 8B:
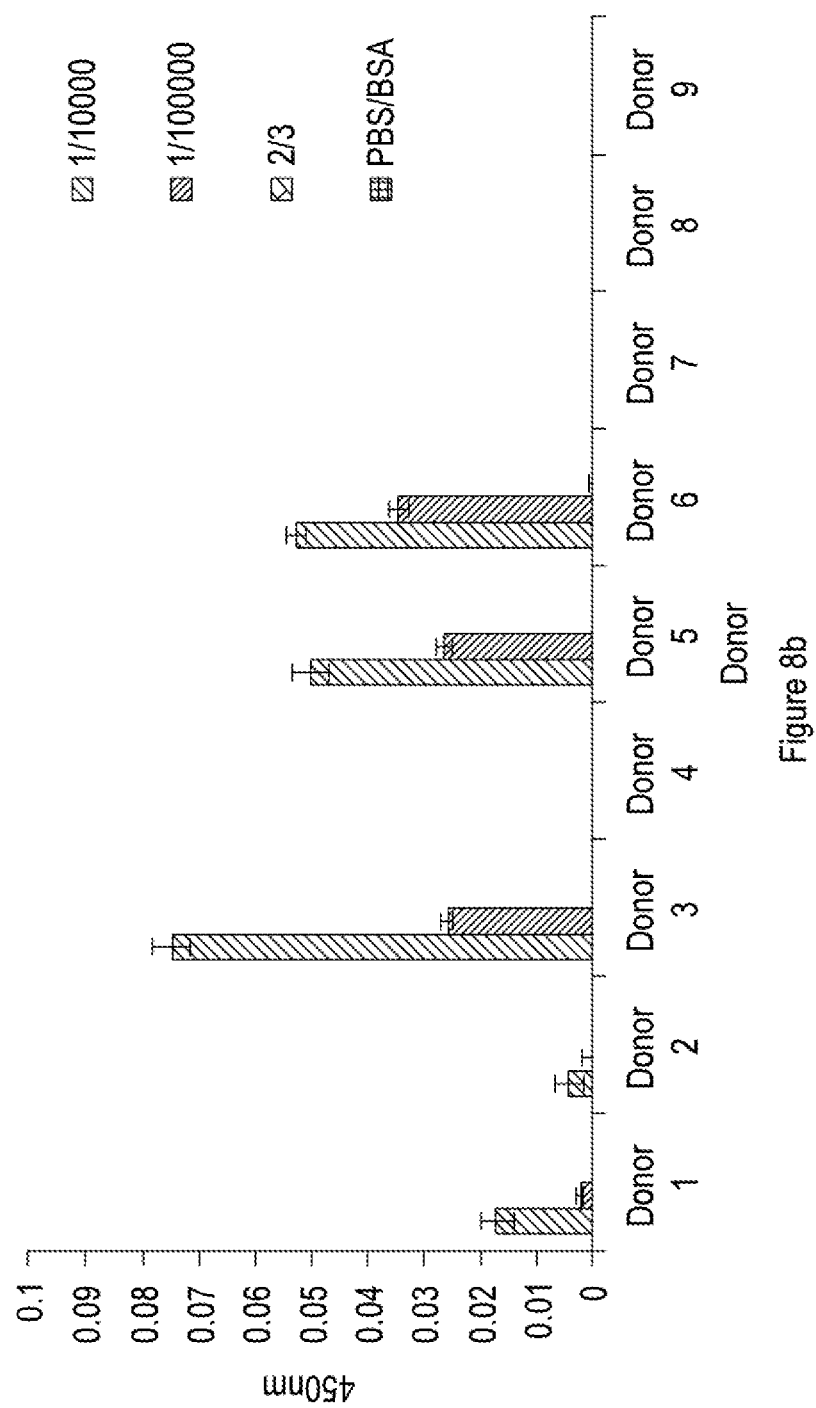
FIG. 8b: Sandwich ELISA using FG88.2 for the detection of secreted Lea in saliva. Saliva from nine healthy donors was collected, heat inactivated and analyzed for the presence of Lea. Three out of nine donors tested strongly positive.
Figure 8C:
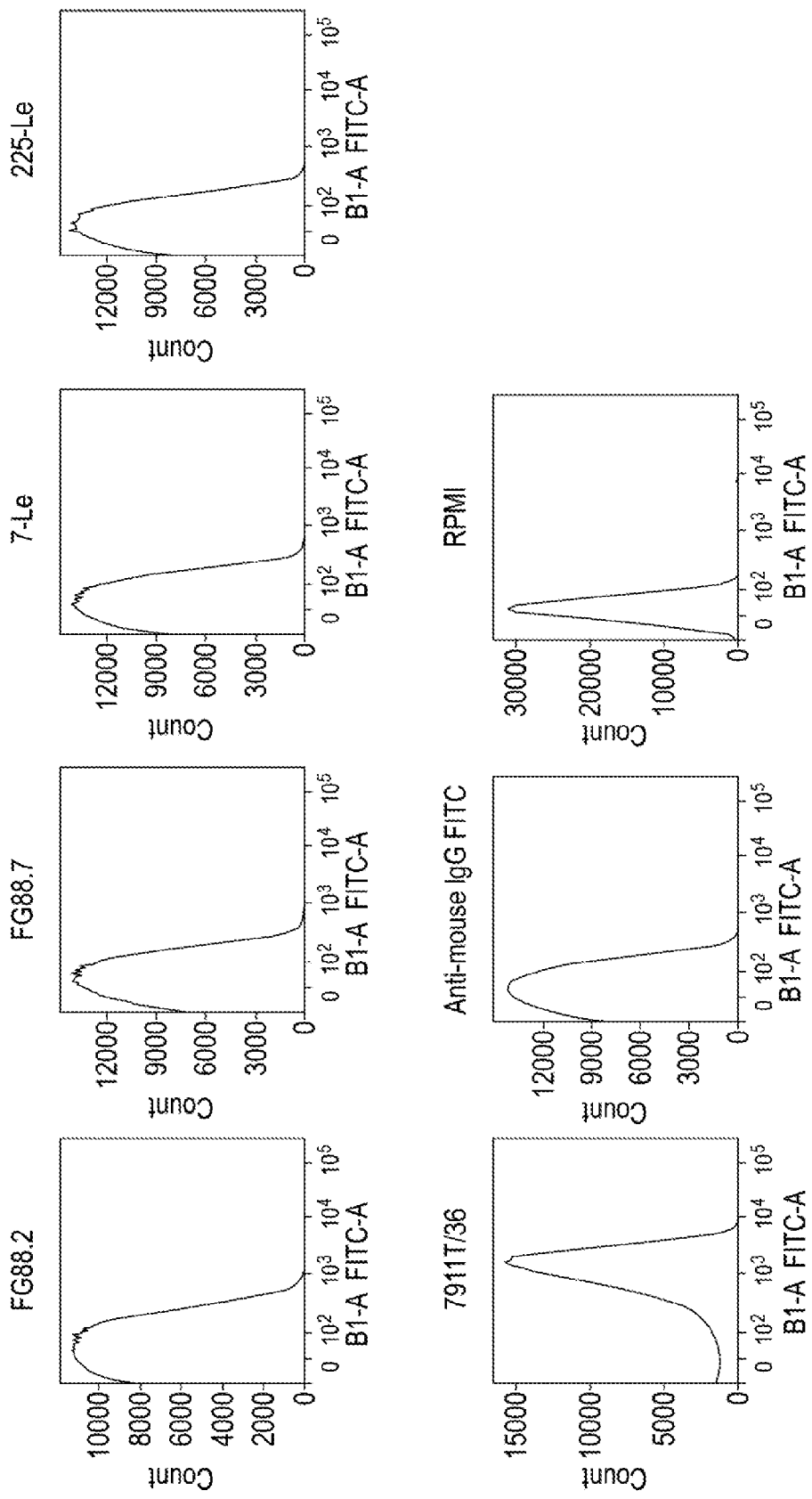
FIG. 8c: Evaluation of FG88 binding to erythrocytes from $Le^a$-positive donor by flow cytometry. Absence of erythrocyte binding by FG88.2 (i) and FG88.7 (ii) was compared to control mAbs: 7-Le, anti-$Le^a$ (iii) and 225-Le, anti-$Le^e$ (iv). MAb 791T/36, anti-CD55 (v) and (vi) IgG isotype control were used as positive and negative controls, respectively. Representative result from three $Le^a$-positive donors.

The need to determine normal red blood cell binding was further necessitated as within the literature, there is an indication that $Le^a$ antigens found in the secretions of various tissue types have the capability of adsorbing to the surface of erythrocytes. The term ABH secretor refers to the secretion of ABO blood group antigens into the individual's body fluids. Among Lewis antigen positive individuals, ABH secretors are always $Le^{a-b+}$ whereas ABH non-secretors are always $Le^{a+b-}$. In Caucasians, it was reported that approximately 80% are of secretor status and 20% are non-secretors. The secretor status of nine healthy human donors was determined by saliva sandwich ELISA (FIG. 8b), followed by binding analysis of the FG88 mAbs to erythrocytes from a $Le^a$-positive donor. Neither FG88 mAb bound to the erythrocytes (FIG. 8c).

TABLE 4

Binding of FG88.2 and FG88.7 (5 μg/ml) to a panel of tumour cell lines as assessed by FACS. 505/4, CA19-9, 7-Le (5 μg/ml). 791T/36 (5 μg/ml) and W6/32 (1 μg/ml) were used as positive controls and media alone as the negative.

| Cell line | Gm value | | | | | | | |
|---|---|---|---|---|---|---|---|---|
| | FG88.2 (anti-Le$^{a/x}$) | FG88.7 (anti-Le$^{a/x}$) | 505/4 (anti-sDLe$^a$) | CA19-9 (anti-sLe$^a$) | 7-Le (anti-Le$^a$) | 791T/36 (anti-CD55) | W6/32 (anti-HLA-A, B, C) | RPMI |
| Colorectal | | | | | | | | |
| C170 | 2553.83 | 3096.03 | 8220.66 | 7667.27 | 8692.18 | 858.47 | 16.52 | 17.62 |
| Colo205 | 831.25 | 723.61 | 3260.9 | 3212.15 | 5058.59 | 44.44 | 1300.62 | 9.07 |
| Colo201 | 720.72 | 503.92 | 2471.68 | 1647.5 | 3350.2 | 22.26 | 603.08 | 21.74 |
| HT29 | 204.91 | 190.8 | 585.12 | ND | ND | 916.22 | 1162.5 | 18.84 |
| Pancreatic | | | | | | | | |
| ASPC1 | 19.2 | 19.05 | 19.96 | 21.01 | 47.41 | 7008.83 | 1775.04 | 18.73 |
| Panc1 | 750.5 | 597.2 | 5339.55 | 4114.72 | 4328.87 | 471.84 | 20.09 | 18.24 |
| Lung | | | | | | | | |
| H69 | 129.71 | 97.74 | 1116.4 | 358.26 | 142.96 | 28.09 | 109.02 | 17.69 |
| Gastric | | | | | | | | |
| AGS | 67.26 | 33.85 | 28.19 | 20.82 | 29.72 | 1877.02 | 1563.61 | 19.39 |
| ST16 | 806.94 | 698.76 | 4226.31 | 2045.5 | 3615.76 | 902.58 | 33.55 | 27.53 |
| MKN45 | 1.37 | 134.24 | 79.2 | 14.47 | 154.61 | 230.97 | 15.42 | 17.25 |
| Ovarian | | | | | | | | |
| OVCAR3 | 120.96 | 68.19 | 154.48 | 26.67 | 48.5 | 411.72 | 633.41 | 21.19 |
| OVCAR4 | 47.41 | 25.69 | 14.34 | 14.16 | 15.08 | 327.91 | 16.38 | 13.42 |
| OVCA433 | 20.56 | 19.93 | 18.94 | 19.23 | 24.74 | 686.37 | 6785.04 | 17.88 |
| OAW42 | 32.78 | 31.74 | 33.77 | 28.79 | 42.09 | 400.73 | 317.67 | 28.33 |
| Breast | | | | | | | | |
| MCF7 | 34.75 | 31.86 | 17.97 | ND | ND | 460.6 | 514.99 | 30.99 |
| MB-MDA-231 | 22.04 | 23.58 | 14.87 | ND | ND | 1161.68 | 757.94 | 16.96 |
| DU4475 | 1462.03 | 720.20 | 1325.76 | ND | ND | ND | 1358.12 | 8.62 |

ND = not determined.
Results are expressed as Gm.

Example 6

FG88 Internalisation Studies

Figure 9A:
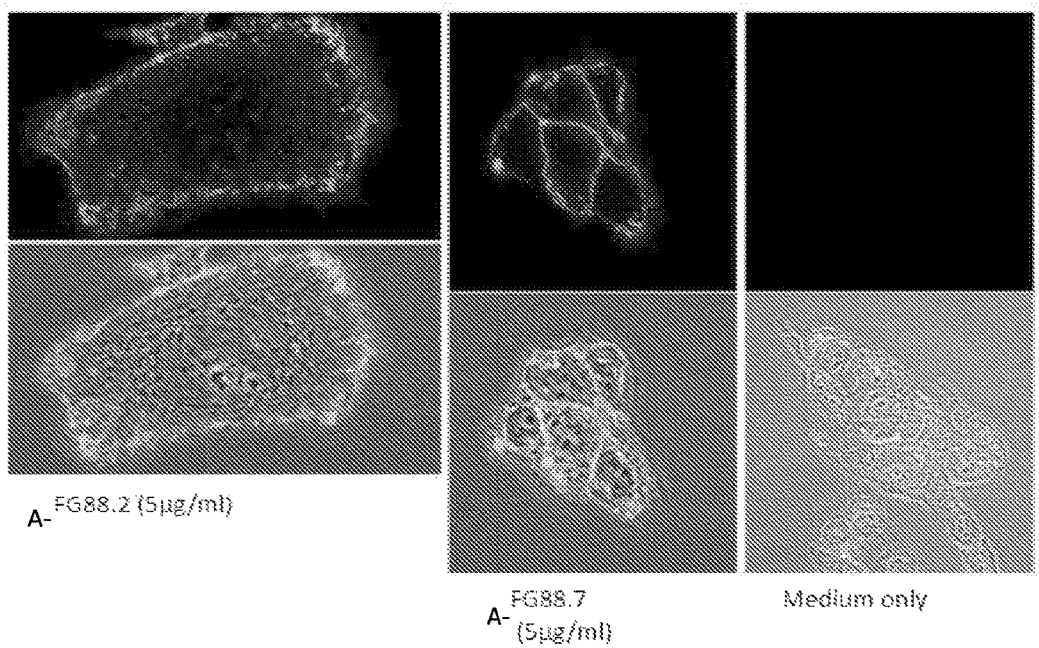
FIG. 9a: Confocal microscope analysis of the internalisation of FG88.2 and FG88.7 mAbs on C170 cells. C170 cells were grown on coverslips and incubated with a) Alexa-488 labelled FG88.2 (A-FG88.2; 5 μg/ml) mAb, b) Alexa-488 labelled FG88.7 (A-FG88.7; 5 μg/ml) mAb and c) medium alone (negative control) for 2 hrs and processed as described in the 'methods'.

FG88 mAbs were analysed for cellular internalisation via confocal microscopy. They were labelled with Alexa-488 fluorophore following the manufacturer's protocol and the labelling efficiency checked via direct flow cytometric analysis of the mAb binding to the C170 cell surface. Confocal microscopy was then used to follow the cellular internalisation of FG88 mAbs by C170 cells over a two-hour incubation period. Cross-sectional images were obtained at 0.8 μm intervals and showed efficient internalisation after a two-hour incubation period. In addition, clustering of FG88 mAbs on C170 cell surface was observed, suggesting the heterogeneous distribution of the antigen in the C170 plasma membrane (FIG. 9a).

Figure 9B:
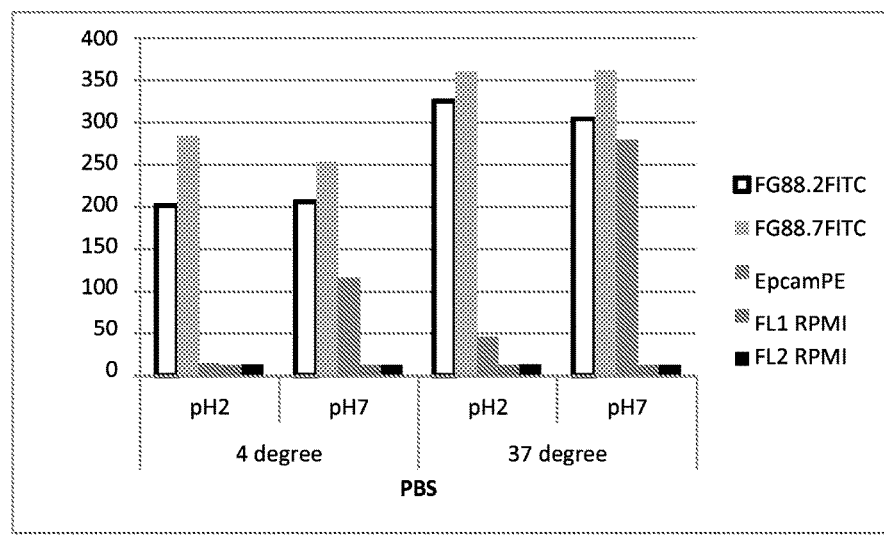
FIG. 9b: Assessment of the internalisation of FITC-labelled FG88.2 (FG88.2FITC) and FG88.7 (FG88.7FITC) mAbs into Colo205 cells at 4° C. and 37° C. by acid wash flow cytometric analysis. Internalisation of FG88.2FITC and FG88.7FITC mAbs to Colo205 cells were compared to PE-labelled Epcam mAb (EpcamPE) which was used as positive control. PBS at pH2, and pH7 were used as wash buffers to wash away mAbs bound to cell surface antigens. Medium alone (RPMI) was used as negative control. FITC-labelled samples were analysed via the FL1 channel and PE-labelled samples, the FL2 channel.

A more quantitative analysis was performed using direct flow cytometry on Colo205 cells after acid wash and FITC-labelled murine FG88 mAbs. The results showed that wash buffer at pH2.0 strips any surface-remaining antibody (as seen by the near complete removal of Epcam PE fluorescence), but FG88-FITC labelled cells remain fluorescent after acid wash at pH 2.0, indicating the internalisation of the FITC-labelled FG88 mAbs (and thus protection from the acid wash). Colo205 cells internalised FG88.7 and FG88.2 to a similar degree at 37° C. and 4° C. (FIG. 9b).

Over time, internalised FG88 mAbs co-localised with lysosomal compartments (FIG. 9c). Similar results were obtained with FG88.7 (data not shown). Importantly, internalization was validated through toxicity of Fab-ZAP-FG88 immune complexes containing saporin. Internalization of the Fab-ZAP-FG88.2 and Fab-ZAP-FG88.7 complexes, but not the Fab-ZAP alone or the Fab-ZAP preincubated with a control mAb (data not shown), led to a dose-dependent decrease in cell viability of the high glyco-epitope expressing C170, Panc1 and ST16 cells (FIG. 9d). The moderately binding HT29 cells were more refractory.

In summary, Colo205, C170 Panc 1 and ST16 cells efficiently internalise the murine FG88 antibodies and this may be linked to their direct cell killing ability.

Example 7

Figure 10A:
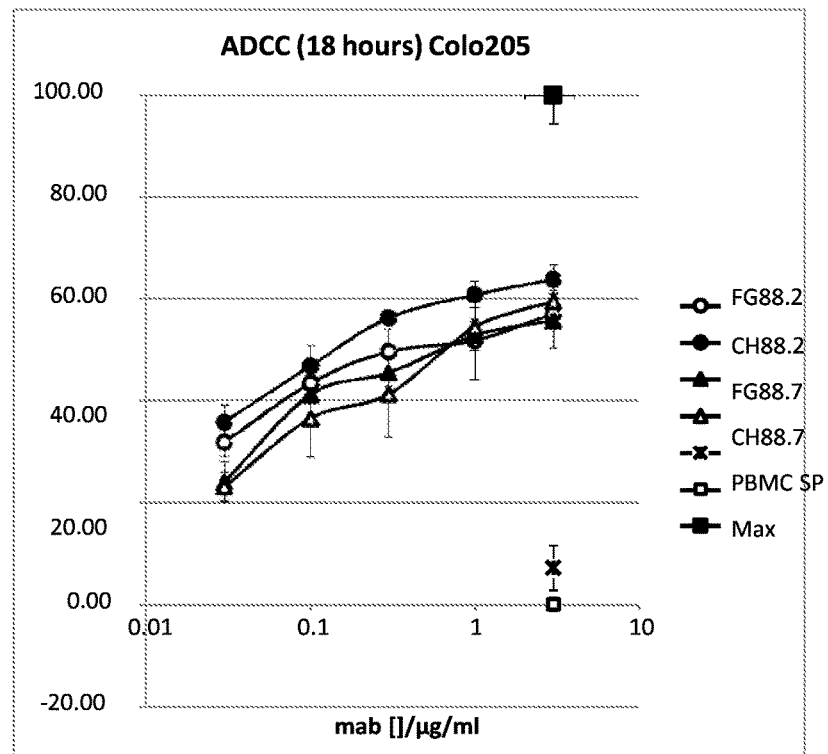
FIG. 10a: ADCC killing of Colo205 cell line by FG88.2 and FG88.7. $^{51}$Cr-labeled cells were cultured at $5\times10^3$ cells/50 μl with increasing concentrations of antibodies in the presence of PBMCs. The cells were incubated for 18 hrs at 37° C. $^{51}$Cr released in the supernatant was measured as percentage of total $^{51}$Cr released with 10% Triton-X. PBMCs plus Colo205 cells were included as a negative control.
Figure 10B:
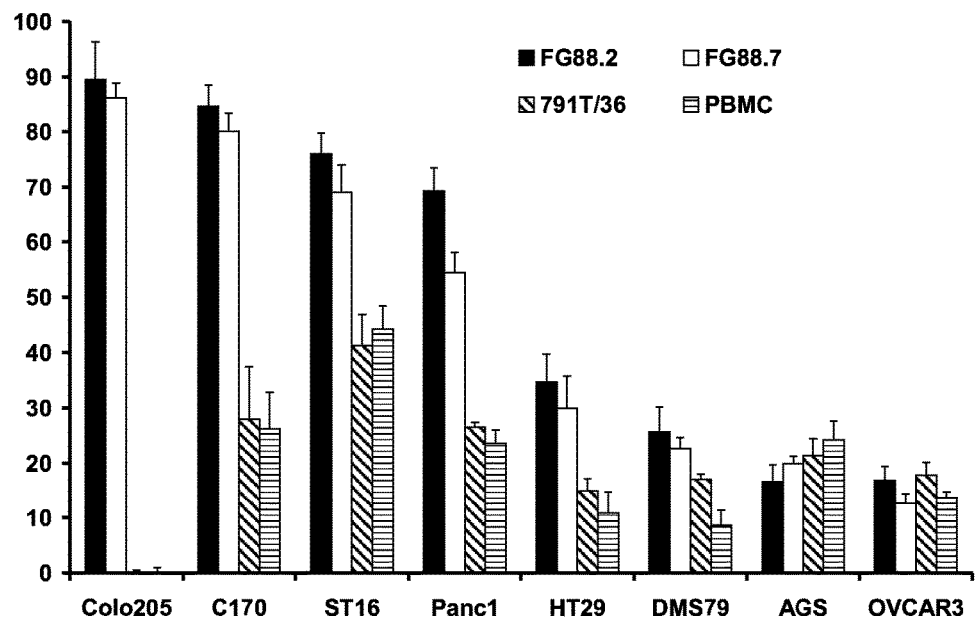
FIG. 10b: ADCC activity of FG88 mAbs on a panel of tumor cell lines. FG88 mAbs and control (791T/36) were used at 10 μg/ml.

In Vitro Anti-Tumour Activity of FG88
ADCC and CDC:

The ability of murine and chimeric FG88 mAbs to induce tumour cell death through ADCC was screened. Human PBMCs were used as the source of effector cells while Colo205 cells served as target cells. The number of cells killed by mAbs FG88.2, FG88.7, CH88.2 and CH88.7 was measured after 18 hr incubation at 37° C. As shown in FIG. 10a, Colo205 cells were susceptible to FG88.2, FG88.7, CH88.2 and CH88.7 mAbs killing showing a maximum of 57%, 56%, 64% and 59% lysis respectively. A range of tumor cell lines were analyzed for their susceptibility to FG88-mediated ADCC. The FG88 mAbs significantly lysed the high glyco-epitope expressing Colo205, C170, ST16 and Panc1 cells above the killing observed with PBMCs alone (FIG. 10B). The mAb 791T/36, a murine IgG2b that cannot bind human CD16 (32), showed no significant killing over the background observed with PBMCs alone. PBMC killing in the absence of FG88 mAbs was highest for cell lines lacking MHCI such as C170, ST16, Panc1 and AGS and probably reflects NK killing. Noticeably less immune-mediated killing was seen with the FG88 mAbs on the moderate-binding HT29 and DMS79 cells even at high mAb concentration of 10 μg/ml; the weak-binding OVCAR3 and AGS were refractory.

Figure 10C:
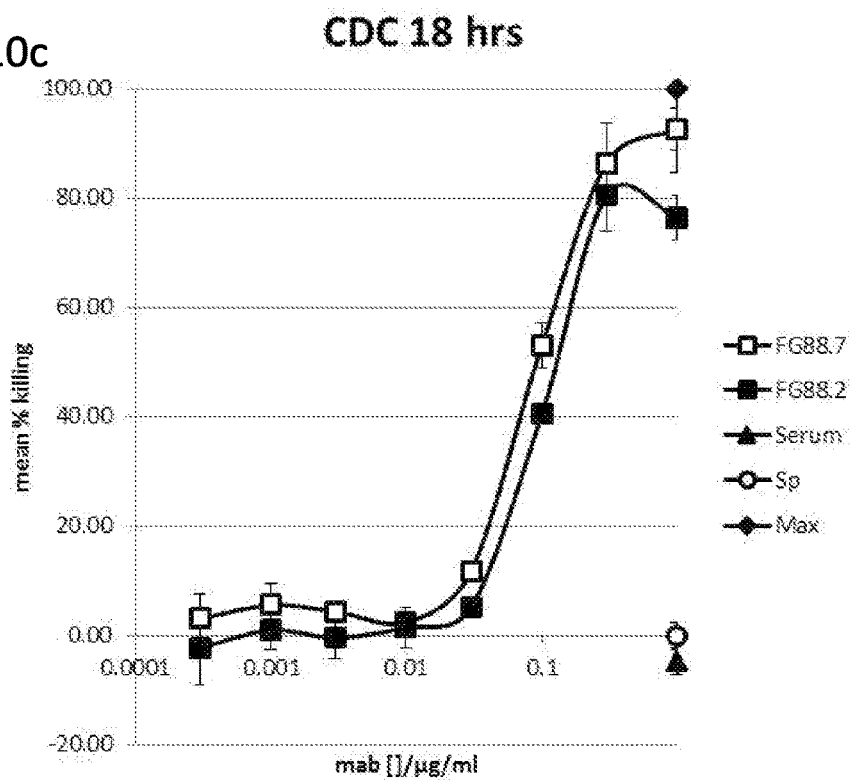
FIG. 10c: CDC killing of C170 cell line by FG88.2 and FG88.7 mAbs. C170 cells were incubated at $5\times10^3$ cells/50 μl in the presence of increasing concentrations of FG88.2 and FG88.7 in the presence of human serum. The percentage cell lysis was measured after 18 hrs at 37° C. $^{51}$Cr released in supernatant was measured as percentage of total $^{51}$Cr released with 10% Triton-X. Serum plus Colo205 cells were included as a negative control.
Figure 10D:
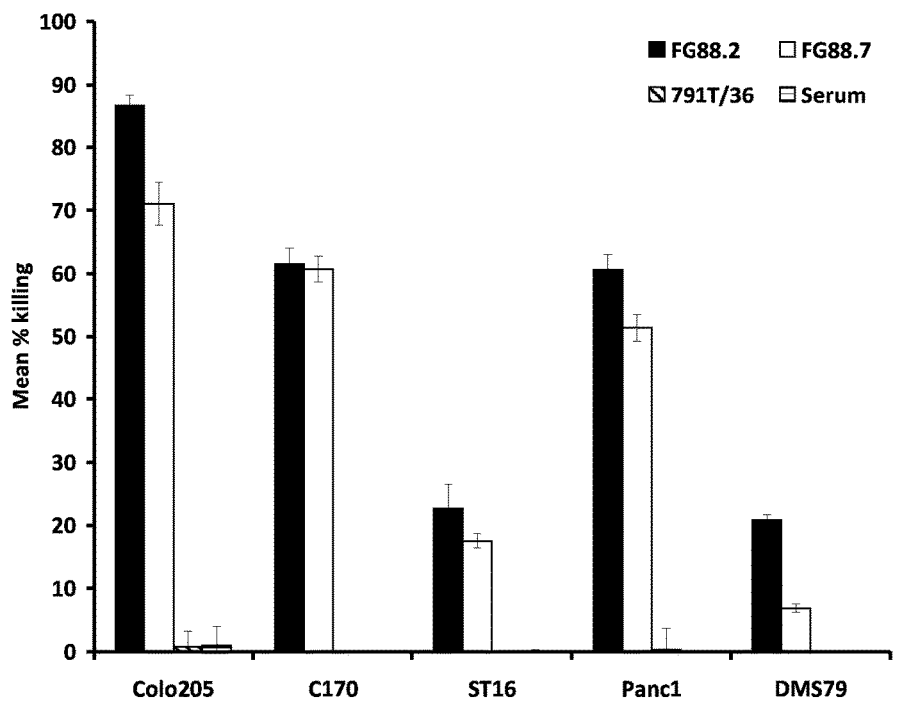
FIG. 10d: CDC activity of FG88 mAbs on a panel of tumor cell lines. FG88 mAbs and control (791T/36) were used at 10 μg/ml. Significance (Panels B and D) was established by multiple t-tests versus PBMC or serum control receptively, with Holm-Sidak correction for multiple comparisons and α=0.05 (GraphPad Prism 6).

CDC is known to be an important mechanism involved in eliminating tumour cells in vivo. The capacity of the C170 cells to be killed by CDC induced by mAbs FG88.2 and FG88.7 in the presence or absence of human serum as source of complement at 37° C. for 18 hr was assayed. FG88.2 and FG88.7 showed a maximum of 80% and 91% lysis respectively (FIG. 10c). The FG88 mAbs displayed significant CDC activity against Colo205 and Panc1 cells and to a lesser degree ST16 and DMS79 cells (FIG. 10D). No or little CDC was seen on the low- to moderate-binding cell lines HT29, OVCAR3 and AGS (data not shown). The low level of CDC killing of the high-binding ST16 cells could be due to higher levels of membrane complement regulatory proteins (MCRPs) (33). Additionally, the efficient FG88-mediated ADCC of ST16 cells under the same conditions, rules out the possibility that the reduced complement activation was due to suboptimal mAb binding.

In summary, FG88 strongly induced ADCC using human PBMCs as effector cells as well as significant CDC with human serum as a complement source.

Figure 11A:
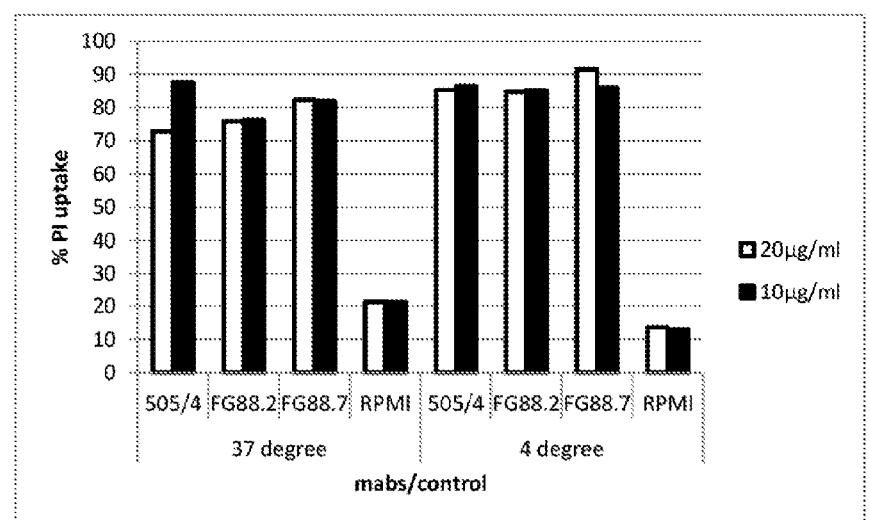
FIG. 11a: FG88.2 and FG88.7 induced PI uptake (suggestive of direct cell death) into C170 cells at both 37° C. and 4° C. C170 cells were incubated with 10 and 20 μg/ml of FG88.2 and FG88.7 at 37° C. and 4° C. 505/4 and medium alone were included as positive and negative controls respectively.
Figure 11B:
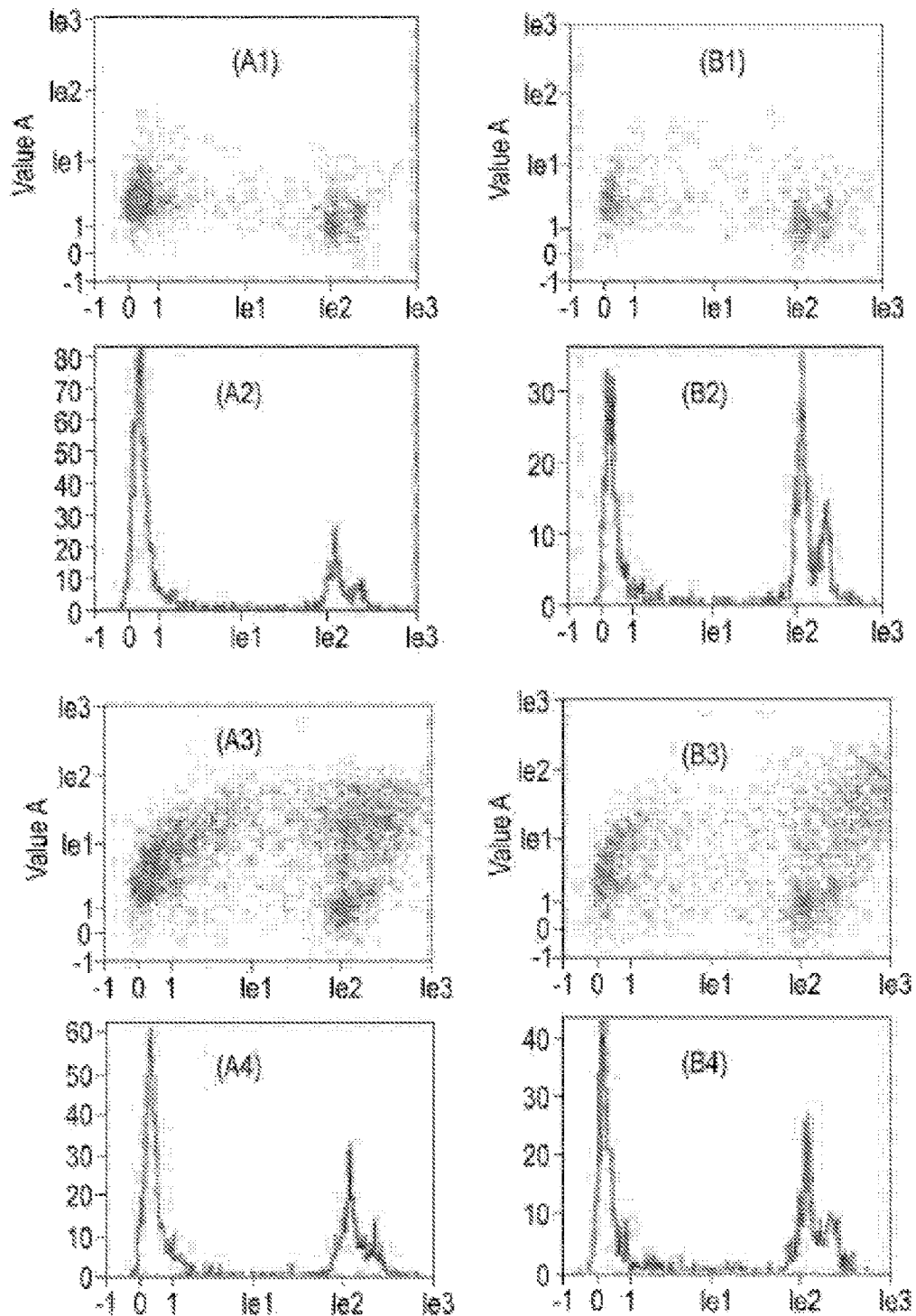
FIG. 11b: FG88.2 and FG88.7 induced PI uptake (suggestive of direct cell death) into C170 cells occurs even in the presence of the caspase inhibitor Z-FMK-VAD. The panels A1-D1 and A3-D3 show the FACS dot plots corresponding to histograms of C170 cells incubated with FG88.2 at 10 μg/ml+/−Z-FMK-VAD (A2 and A4), FG88.2 at 30 μg/ml+/−Z-FMK-VAD (B2 and B4), FG88.7 at 10 μg/ml+/−Z-FMK-VAD (C2 and C4) and FG88.7 at 30 μg/ml+/−Z-FMK-VAD (D2 and D4).
Figure 11B:
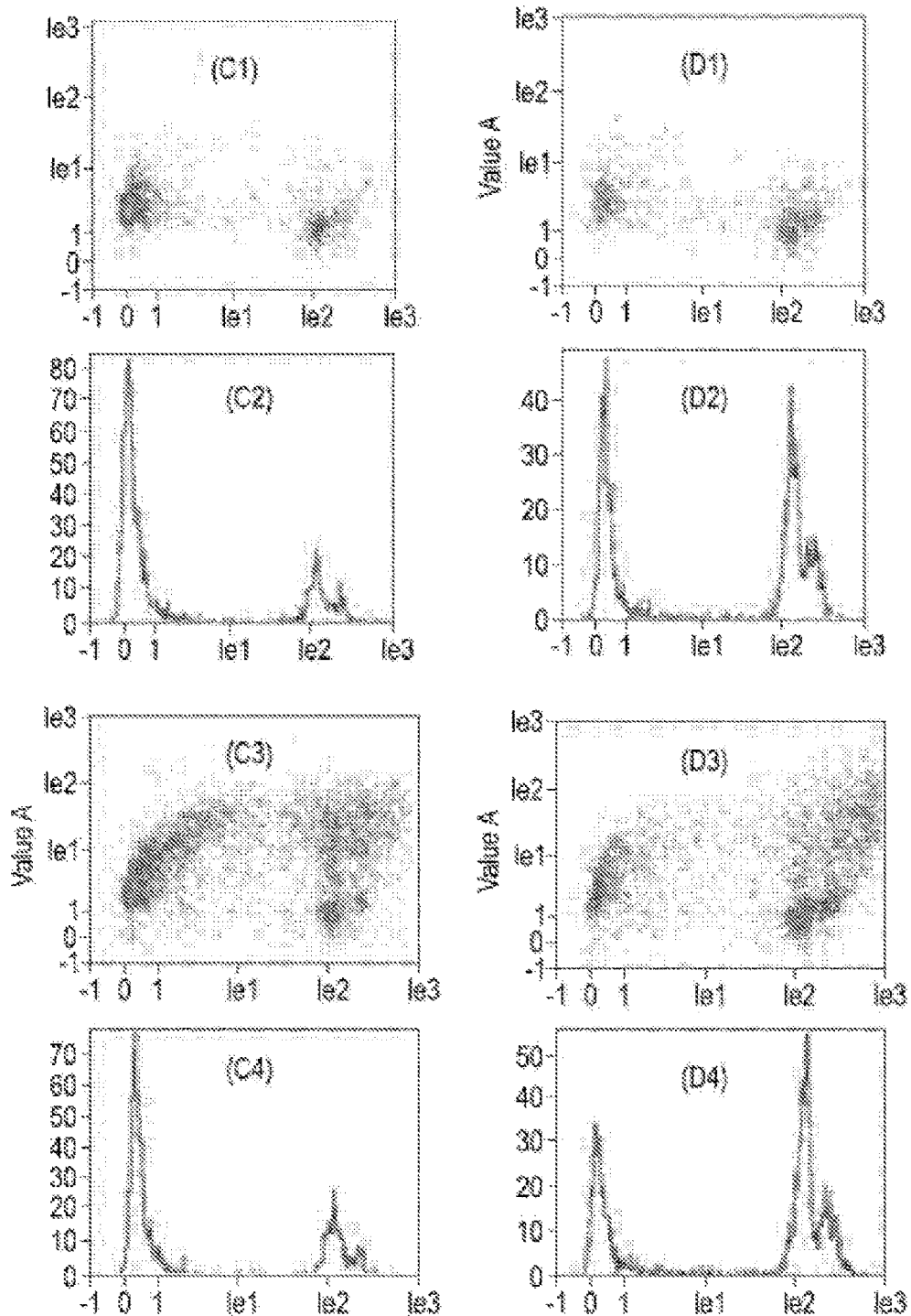

Direct Cell Killing:

FG88.2 and FG88.7 induced membrane damage resulting in the uptake of the small molecular weight dye propidium iodide (PI; FIG. 11a). At 37° C., FG88.2 induced 76% (20 μg/ml) and 76% (10 μg/ml) and FG88.7 induced 82% (20 μg/ml) and 82% (10 μg/ml). Cells incubated with medium alone showed 21% PI uptake. Interestingly even at 4° C., FG88.2 induced 85% (20 μg/ml) and 85% (10 μg/ml) and FG88.7 induced 92% (20 μg/ml) and 86% (10 μg/ml) of the cells to take up PI. Cells incubated with medium alone showed 13% PI uptake. Cells incubated with chimeric FG88.7 induced 54% (30 μg/ml) PI uptake (FIG. 11b).

Figure 12:
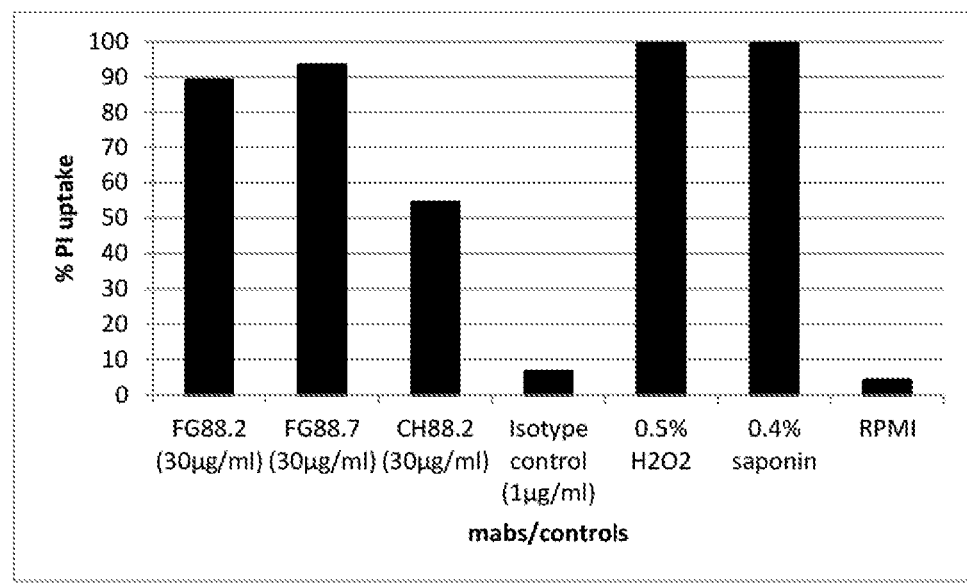
FIG. 12: Chimeric FG88.2 (CH88.2) induced PI uptake of C170 cells at 37° C. C170 cells were incubated with 30 μg/ml of CH88.2 at 37° C. FG88.2 (30 μg/ml) and FG88.7 (30 μg/ml) were included for comparison. Isotype control and medium alone (RPMI) were included as negative controls. 0.5% $H_2O_2$ and 0.4% saponin were used as positive controls.
Figure 13:
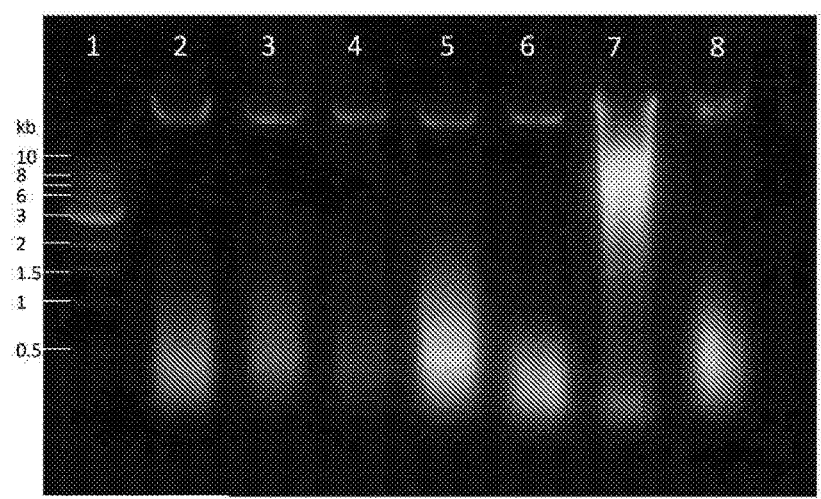
FIG. 13: Measurement of apoptosis associated DNA fragmentation. DNA was extracted from FG88.2-treated C170 cells (lane 2), FG88.2+Z-FMK-VAD-treated C170 cells (lane 3), FG88.7-treated C170 cells (lane 4), FG88.7+Z-FMK-VAD-treated C170 cells (lane 5), untreated C170 cells (lane 6), anti-Fas mAb treated Jurkat cells (lane 7) and anti-Fas+Z-FMK-VAD-treated Jurkat cells (lane 8) and analysed on a 0.8% agarose gel, with DNA equivalent to $1.25\times10^6$ cells per lane. FG88.2 and FG88.7 were used at 30 μg/ml and the anti-Fas mAb at 0.5 μg/ml. Pan-caspase inhibitor Z-FMK-VAD was used at a final concentration of 20 μM. The DNA samples were prepared from untreated or mAb pre-treated cells after treatment for 20 hrs at 37° C. The relative mobility of a 1 kb DNA ladder is shown as molecular weight standards (lane 1).

It has been shown that at temperature lower than 15° C., apoptosis cannot occur. This would suggest that both FG88.2 and FG88.7 induced cell death independent of apoptotic mechanisms. Further evidence for an alternative mechanism of apoptotic induced cell death comes from experiments with the caspase inhibitor Z-FMK-VAD which failed to prevent the direct cell killing of the colorectal cell line, C170, at 4° C. (data not shown although almost identical to those at 37° C.) or 37° C., by the mAb (FIG. 12). Classical apoptotic cell death can be defined by certain morphological and biochemical characteristics which distinguish it from other forms of cell death. One of the hallmarks of apoptosis is DNA fragmentation. In apoptotic cells, DNA is fragmented by endonuclease activity. DNA of C170 cells treated with FG88 mAbs (30 μg/ml) in the presence or absence of pan-caspase inhibitor (Z-FMK-VAD) were analysed using conventional agarose gel electrophoresis. Jurkat cells treated with anti-Fas mAb (0.5 μg/ml) in the presence or absence of Z-FMK-VAD were used as controls for apoptosis. Anti-Fas mAb-treated Jurkat cells showed strong DNA fragmentation and Z-FMK-VAD was shown to inhibit apoptosis induced by anti-Fas mAb (no DNA fragmentation). In contrast, neither FG88.2 or FG88.7 induced DNA fragmentation with or without Z-FMK-VAD again suggesting that these mAbs were not inducing apoptosis (FIG. 13).

Figure 14A:
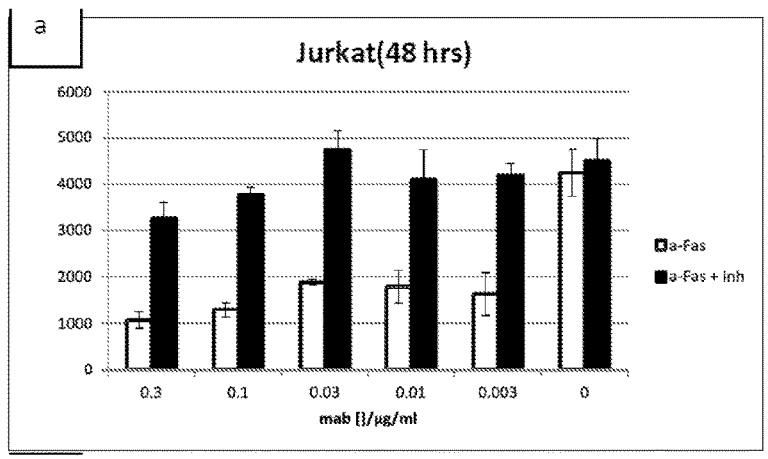
FIGS. 14a-14c: Inhibition of $^3$H-thymidine incorporation into DNA by FG88.2 and FG88.7 in the presence or absence of the pan-caspase inhibitor Z-FMK-VAD in exponential growing C170 human colorectal tumour cells. C170 cells were incubated with FG88.2 (FIG. 14a) and FG88.7 (FIG. 14b) at a range of concentrations from 0.03-3 µg/ml for 48 hrs. Medium alone was used as a negative control. Jurkat cells (FIG. 14c) treated with anti-Fas mAb at a concentration range from 0.003 to 0.3 µg/ml in the presence or absence of pan caspase inhibitor Z-FMK-VAD was used as a positive control.
Figure 14B:
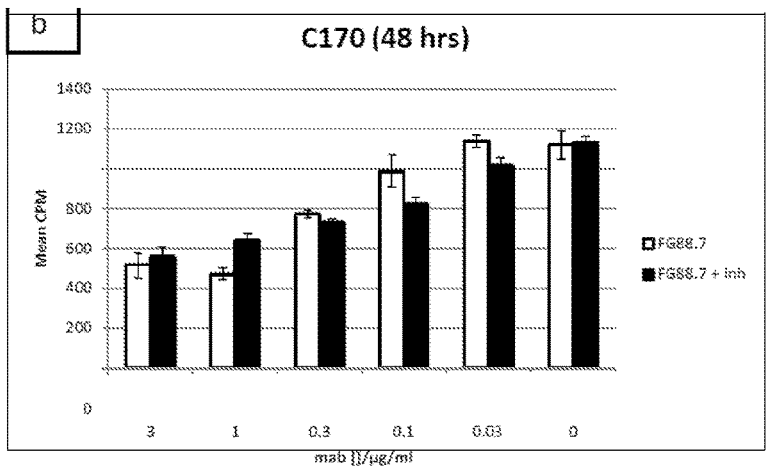
Figure 14C:
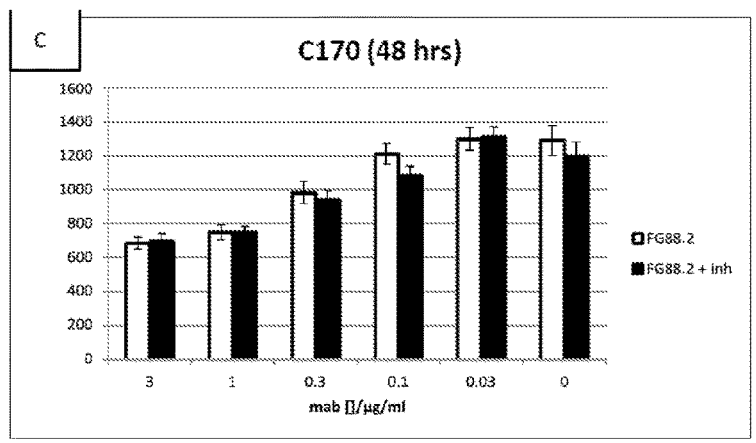

Inhibition of C170 cell growth by FG88.2 and FG88.7: PI uptake assays were performed on cells in suspension. To ensure that the mAbs also inhibited growth of adherent cells, they were exposed to FG88.2 and FG88.7 mAbs and cell growth was assessed by $^3$H-thymidine incorporation (FIG. 14). Both mAbs significantly inhibited adherent cell growth with $IC_{50}$'s of 3 μg/ml. Similarly an anti-Fas mAb inhibited the growth of Jurkat tumour cells (FIG. 14a). However, in contrast to anti-Fas whose growth inhibition was abrogated by a pan-caspase inhibitor, the pan-caspase inhibitor Z-FMK-VAD (carbobenzoxy-valyl-alanyl-aspartyl-[O-methyl]-fluoromethylketone; Promega) failed to inhibit growth induced by the FG88 mAbs suggesting they inhibited cell growth via a non-apoptotic mechanism (FIG. 14b,c).

Figure 15:
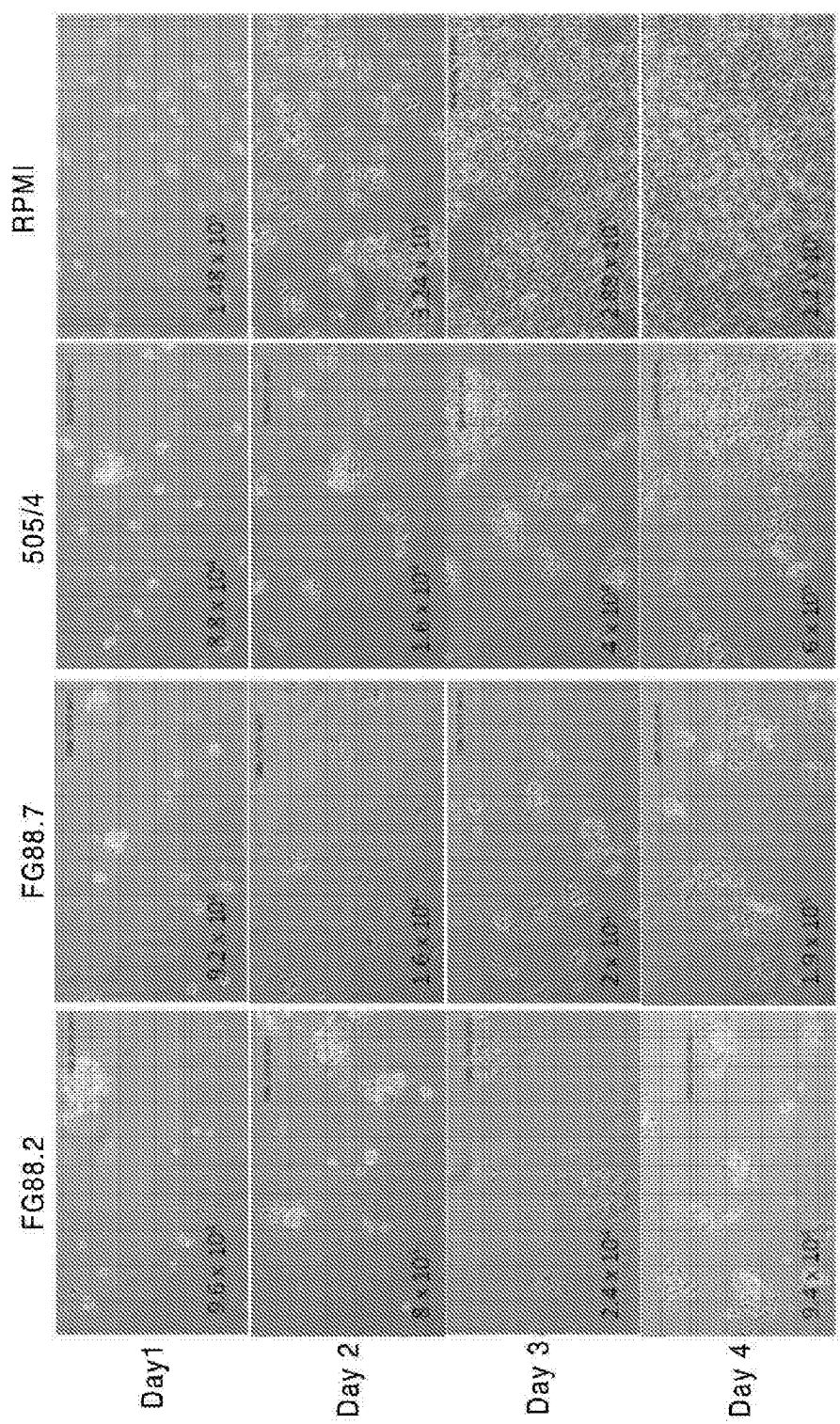
FIG. 15: Inhibition of C170 cell growth by FG88.2 and FG88.7. At day 0, $1\times10^5$ C170 cells were incubated with 10 µg/ml of FG88.7 and FG88.2 at 37° C. for 4 days. 505/4 mAb and medium alone (RPMI) was included as positive and negative controls respectively.
Figure 16:
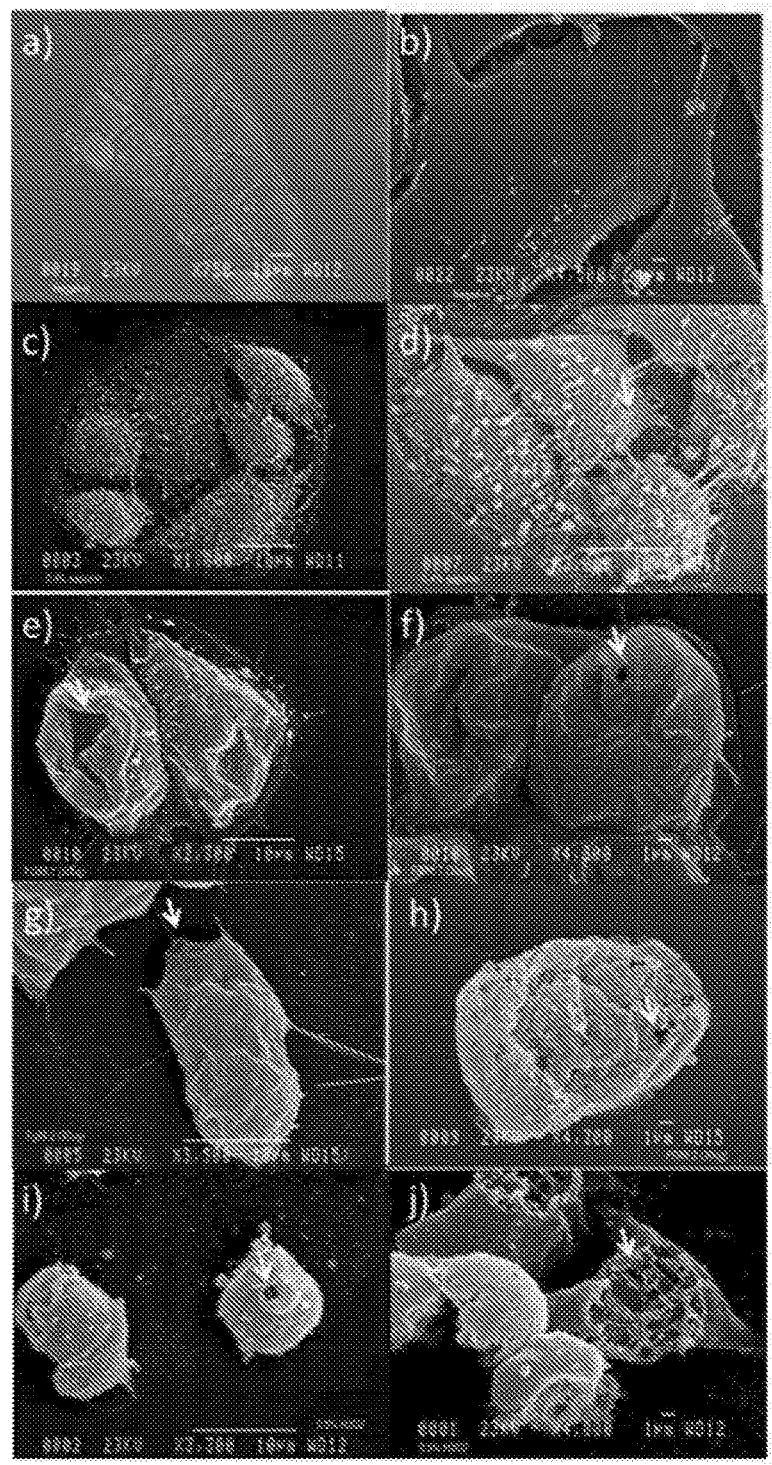
FIG. 16: Scanning electron microscope (SEM) analysis of the C170 cell surface after mAb treatment. C170 cells were grown on coverslips for 24 hr to establish adherent cells and then incubated with a-b) medium alone, c-d) 0.4% saponin, e-f) FG88.7 (30 µg/ml), g-h) FG88.2 (30 µg/ml) and i-j) 0.5% $H_2O_2$ for 20 hrs at 37° C. and processed as described in the 'methods'. Magnifications are at ×2000 (bar=10 µm) and ×10,000 (bar=1 µm). White arrows indicate pores formed on C170 cell surface.
Figure 17:
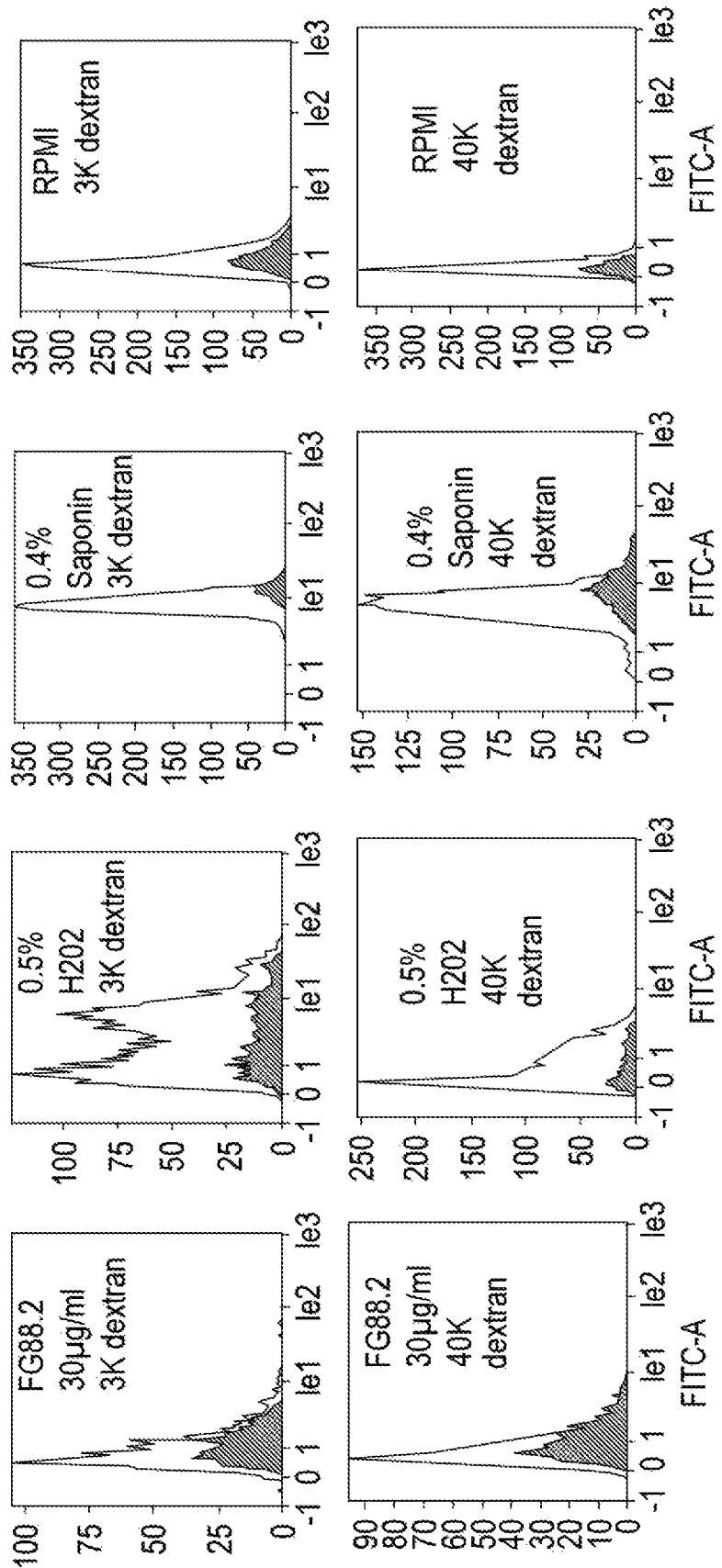
FIG. 17: FG88.2 mAb induced 3 KDa and 40 Kda dextran uptake (suggestive of induced direct cell death) in C170 cells. C170 cells were incubated with 3 KDa and 40 KDa fluorochrome-labelled dextran and treated with 30 µg/ml of FG88.2 mAb at 37° C. for 2 hr. 0.5% $H_2O_2$ and 0.4% (w/v) saponin was used as positive controls. Medium alone (RPMI) was included as negative control. (Green histogram represents single cell population and red histogram represents the aggregated cell population).

To confirm that the PI assay truly reflect cell death in growing cells, C170 cells (Day 0: 1×10$^5$ cells/well) were treated with FG88.2 and FG88.7 and were observed microscopically. C170 cells exhibited monolayer disruption, cell rounding and cell detachment within 30 min after the addition of FG88.2, FG88.7 or 505/4 mAbs. However, these phenomena did not develop when C170 cells were incubated with medium alone. As shown in FIG. 15; FG88.2, FG88.7 and 505/4 mAbs inhibited C170 cell growth at day 1, 2 and 3. At day 4, C170 cells treated with FG88.7 (1.9×10$^5$ cells) and FG88.2 (9.4×10$^4$ cells) mAbs started to regrow. Cells incubated with media alone did not show growth inhibition and achieved 80% confluency at day 3. To confirm the morphological changes observed under the light microscope, C170 cells were exposed to FG88.2 and FG88.7 mAbs for 20 hr prior to analysis under a scanning electron microscope (SEM). Pronounced cell aggregation of C170 adherent cells after incubation with FG88 mAbs was observed. These cell aggregates displayed a loss of surface microvilli, the formation of membrane blebs and surface wrinkles. Most importantly, these clumped cells showed evidence of membrane pores which is reminiscent of oncosis. The sizes of these pores were heterogeneous with diameters ranged from 0.2 μm to 1 μm (white arrows) (FIG. 16). To further confirm that FG88 mAbs induced oncosis, C170 cells were treated with FG88.2 mAb and then the uptake of dextran of different molecular weights (3 kDa and 40 kDa) was assessed. FG88.2 mAb induced uptake of both 3 and 40 KDa molecular weight dextran in 2 hr (FIG. 17).

Figure 18:
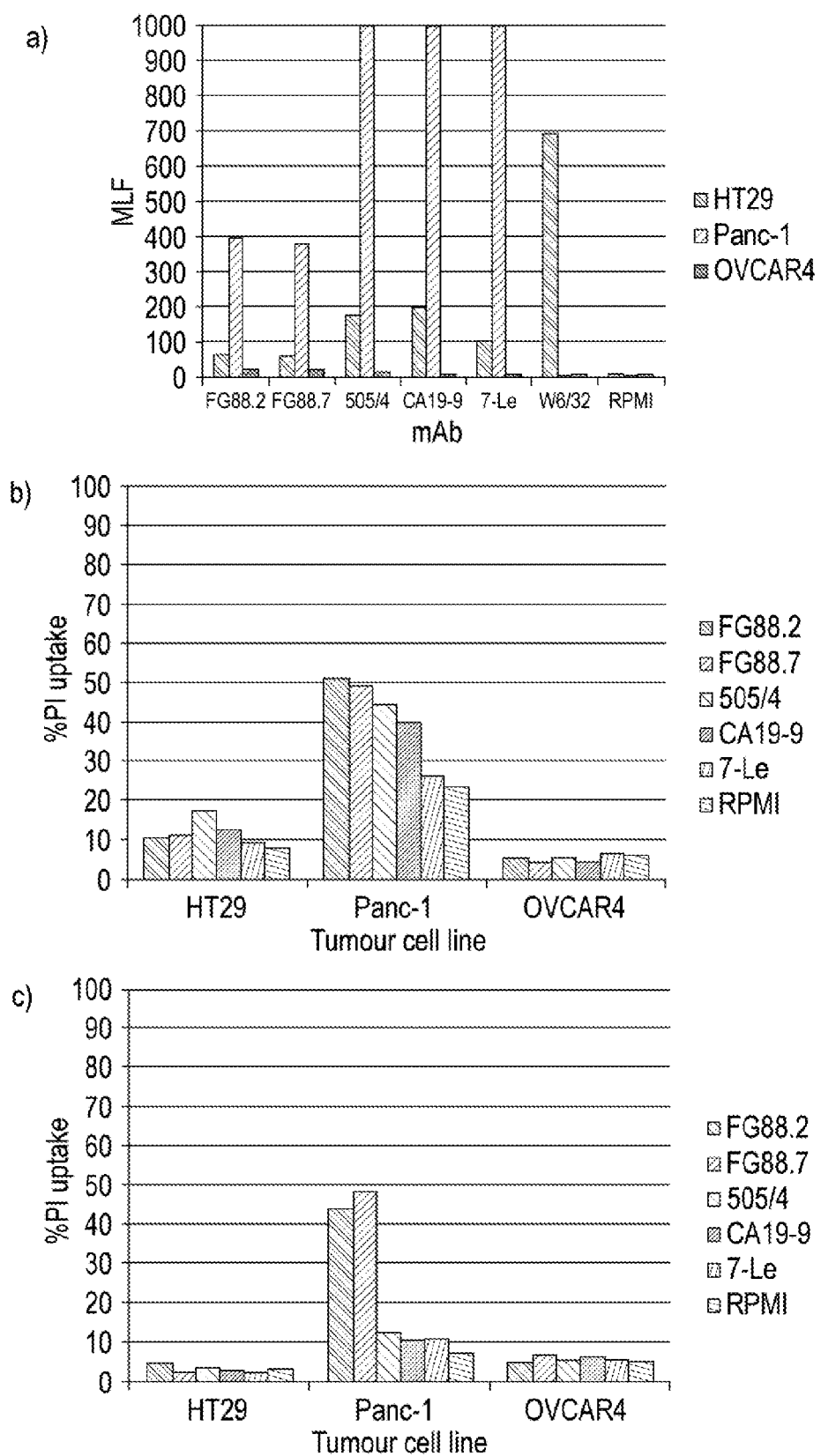
FIG. 18a: Binding of FG88.2 and FG88.7 mAbs to cells with different antigen expression level. Exponentially growing tumour cells were harvested and stained by indirect immunofluorescence and analysed by flow cytometry analysis. W6/32 (anti-HLA-A,B,C) and medium alone (RPMI) were used as positive and negative controls, respectively. 505/4, CA19-9 and 7-Le were included in the same panel for comparison. Results are expressed as geometric means (y-axis; labelled MLF).
FIG. 18b,c: Uptake of PI by HT29, Panc-1 and OVCAR4 tumour cells at b) 37° C. and c) 4° C. with FG88.2, FG88.7, 505/4, CA19-9 and 7-Le mAbs at 10 µg/ml. Medium alone (RPMI) was included as a negative control.
Figure 19A:
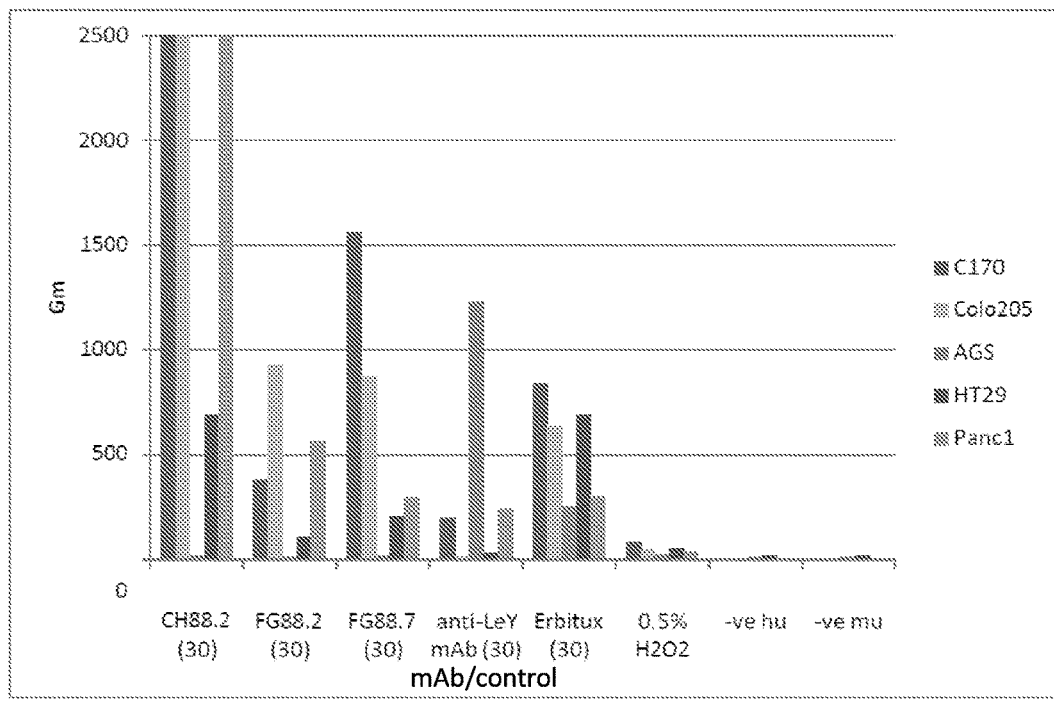
FIG. 19a: Binding of FG88.2, FG88.7 and CH88.2 to a panel of tumour cell lines. Binding of FG88.2, FG88.7 and CH88.2 at 30 µg/ml to C170, Colo205, AGS, HT29 and Panc1 was assessed by immunofluorescence staining and flow cytometric analysis. In all cell lines, binding was compared to the positive control, Erbitux (anti-EGFR). An anti-Le$^y$ mAb (30 µg/ml) was included for comparison. Medium alone (RPMI) was used as negative control. Results are expressed as geometric means (Gm).
Figure 19B:
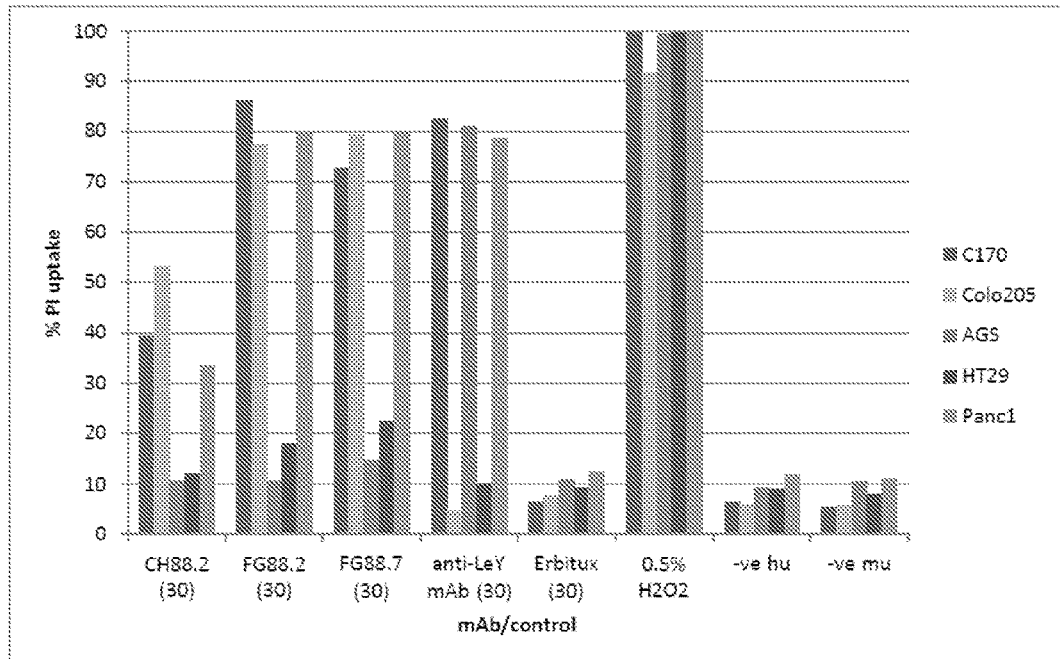
FIG. 19b: Uptake of PI by C170, Colo205, AGS, HT29 and Panc1 tumour cells at 37° C. with CH88.2. Cells were incubated with 30 µg/ml of CH88.2 for 2 hr at 37° C. FG88.2, FG88.7, anti-Le$^y$ mAb and Erbitux were included in same panel at 30 µg/ml for comparison. 0.5% $H_2O_2$ and medium alone (RPMI) were included as positive and negative controls respectively. Results are expressed as geometric means (Gm).

To assess direct killing on cells with varying expression of glycans at 37° C. and 4° C., PI uptake assay was carried out using FG88.2 and FG88.7 mAbs with Panc-1, HT29 and OVCAR-4 cells (FIG. 18). 505/4 and medium alone were included as positive and negative controls respectively. 7-Le and CA19-9 mAbs were included for comparison. FG88.2 and FG88.7 mAbs induced direct cell death on Panc-1 at both 37° C. and 4° C. whereas 505/4 induced Panc-1 cell death only at 37° C. suggesting FG88.2 and FG88.7 induced direct cell death independent of an apoptotic mechanism. Interestingly, FG88.2, FG88.7 and 505/4 mAbs did not induce HT29 cell death despite binding moderately to HT29 cells. The LecLe$^x$ related glycan negative cell line, OVCAR-4, was not killed. These results revealed a correlation between killing efficiency and the level of LecLe$^x$ related glycan expression with cells expressing moderate/low levels not being killed. Chimeric FG88.2 also induced PI uptake in cells expressing high (C170, Colo205 and Panc1) but not low or negative density (HT29 and AGS) antigen (FIG. 19).

Experiments with different antigen negative human colorectal tumour cells, whole blood (PBMCs and granulocytes) or erythrocytes from normal human donors displayed no binding and no direct killing activities for mouse and/or chimeric FG88 mAbs. Taken together the chimeric FG88 mAb had similar potency and specificity when compared with parental mouse FG88 mAb. Examination of FG88 treated tumour cell surface by scanning electron microscopy (SEM) revealed pore formation. This mechanism of cell death resembles that described for oncosis.

Example 8

In Vivo Anti-Tumour Activity of FG88

Comparison of the therapeutic effect of the mAb FG88 in the C170HM2 DLuX human hepatic metastasis model: The mouse C170HM2 DLuX human hepatic metastasis tumour model was used to investigate the anti-tumour activity of the murine FG88 mAb. The C170HM2 DLuX cell line is a bioluminescent variant of a liver metastasising colon tumour cell line passaged to invade the liver parenchyma when implanted into the peritoneal cavity. Growth and distribution/location of such labelled cells and tissue can be assessed non-invasively in real time and in excised tissue at post mortem (PM) in a suitable optical imaging system. These cells were implanted for use as an experimental peritoneal metastasis model.

Figure 20A:
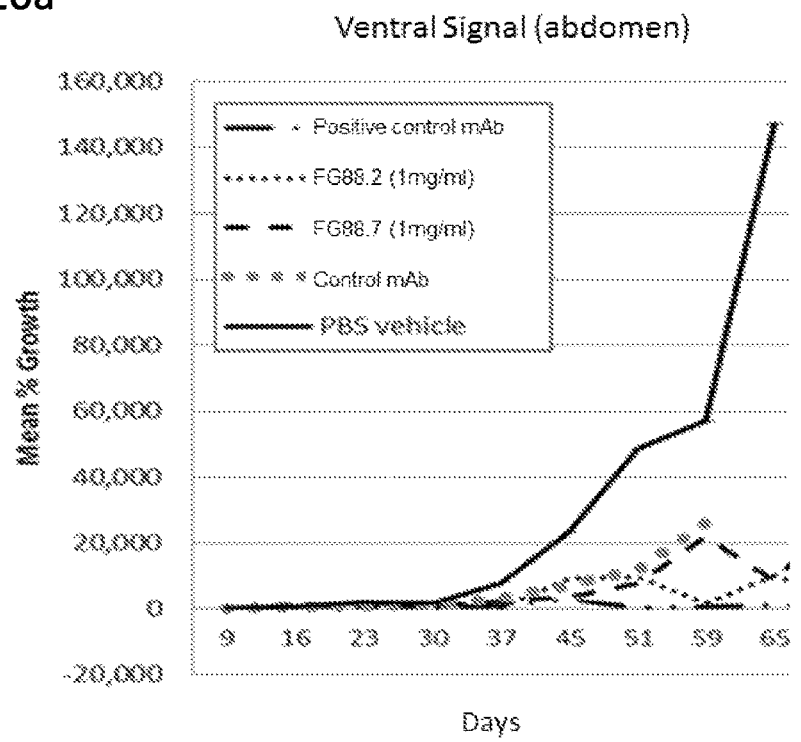
FIG. 20: In vivo anti-tumour activity of FG88 mAbs. a) Percentage tumour growth is shown with the C170HM2 bioluminescence mouse tumour model used to assess the anti-tumour activity of FG88.2 and FG88.7 compared to the positive control mAbs and vehicle only control (PBS). In this model bioluminescence represents tumour cell viability. Group n≥8; the treatment with FG88.2 produced a significant reduction in percentage tumour growth by day 59 (p=0.016). Treatment was halted on day 120. b) Analysis by Log Rank Mantel-Cox test demonstrates significant survival in the FG88.7 (p=0.0037) treatment group compared to the vehicle only control.
Figure 20B:
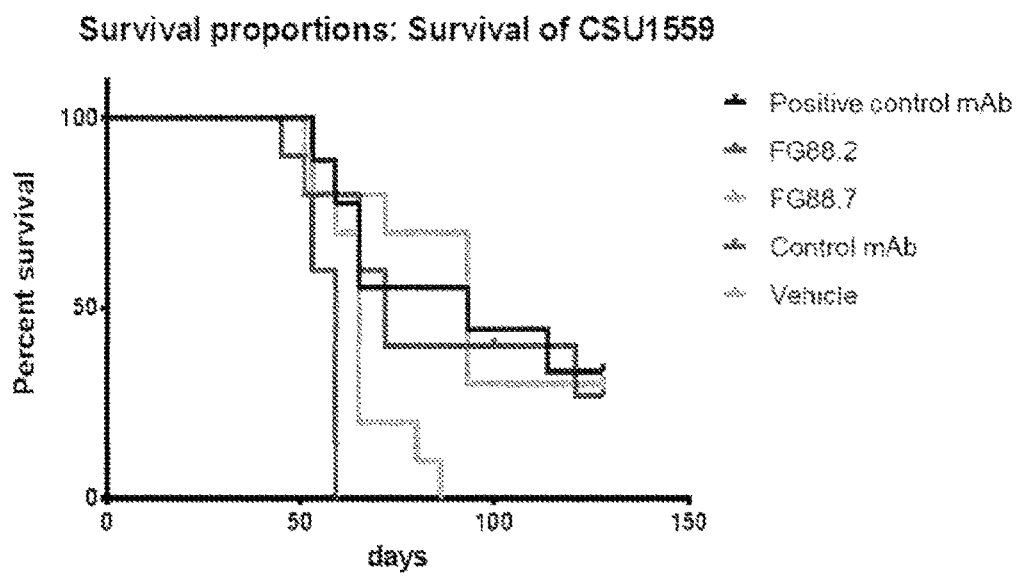

Anti-tumour data: FG88.2, FG88.7 and 505/4, administered twice a weekly (100 μg i.v). reduced peritoneal cavity and associated tumour growth compared to the vehicle control as assessed by bioluminescent intensity (FIG. 20). At day 96 there is a significant difference between vehicle and F88.7 (p=0.037 by log rank (mantel-cox) test). In addition, these mAbs managed to completely eradicate established metastatic tumours in 30% of animals leading to significantly long term survival. F88.2 v vehicle p=0.06; F88.7 v vehicle p=0.0037.

REFERENCES CITED IN THE DESCRIPTION

1 Rabu C, McIntosh R, Jurasova Z, Durrant L: Glycans as targets for therapeutic antitumor antibodies. Future Oncol 2012; 8:943-960.
2 Durrant L G, Noble P, Spendlove I: Immunology in the clinic review series; focus on cancer: Glycolipids as targets for tumour immunotherapy. Clin Exp Immunol 2012; 167:206-215.
3 Yuriev E, Farrugia W, Scott A M, Ramsland P A: Three-dimensional structures of carbohydrate determinants of lewis system antigens: Implications for effective antibody targeting of cancer. Immunol Cell Biol 2005; 83:709-717.
4 Soejima M, Koda Y: Molecular mechanisms of lewis antigen expression. Leg Med (Tokyo) 2005; 7:266-269.
5 Capurro M, Ballaré C, Bover L, Portela P, Mordoh J: Differential lytic and agglutinating activity of the anti-lewis(x) monoclonal antibody fc-2.15 on human polymorphonuclear neutrophils and mcf-7 breast tumor cells. In vitro and ex vivo studies. Cancer Immunol Immunother 1999; 48:100-108.
6 Kitamura K, Stockert E, Garin-Chesa P, Welt S, Lloyd K O, Armour K L, Wallace T P, Harris W J, Can F J, Old L J: Specificity analysis of blood group lewis-y (le(y)) antibodies generated against synthetic and natural le(y) determinants. Proc Natl Acad Sci USA 1994; 91:12957-12961.
7 Tolcher A, Sugarman S, Gelmon K, Cohen R, Saleh M, Isaacs C, Young L, Healey D, Onetto N, Slichenmyer W: Randomized phase ii study of br96-doxorubicin conjugate in patients with metastatic breast cancer. J Clin Oncol 1999; 17:478-484.
8 Pai L H, Wittes R, Setser A, Willingham M C, Pastan I: Treatment of advanced solid tumors with immunotoxin lmb-1: An antibody linked to *pseudomonas* exotoxin. Nat Med 1996; 2:350-353.
9 Yang M C, Hsu F L, Handa K, Hakomori S, Lee M H, Liu L Y, Chang S Y, Ting J, Wen J Y, Ishida I, Chang T H: Human monoclonal antibody gnx-8 directed to extended type 1 chain: Specific binding to human colorectal cancer. Int J Cancer 2009
10 Noble P, Spendlove I, Harding S, Parsons T, Durrant L G: Therapeutic targeting of lewis(y) and lewis(b) with a novel monoclonal antibody 692/29. PLoS One 2013; 8:e54892.
11 Sawada R, Sun S M, Wu X, Hong F, Ragupathi G, Livingston P O, Scholz W W: Human monoclonal antibodies to sialyl-lewis (ca19.9) with potent cdc, adcc, and antitumor activity. Clin Cancer Res 2011; 17:1024-1032.
12 Jeschke U, Mylonas I, Shabani N, Kunert-Keil C, Schindlbeck C, Gerber B, Friese K: Expression of sialyl lewis x, sialyl lewis a, e-cadherin and cathepsin-d in human breast cancer: Immunohistochemical analysis in mammary carcinoma in situ, invasive carcinomas and their lymph node metastasis. Anticancer Res 2005; 25:1615-1622.
13 Magnani J L, Nilsson B, Brockhaus M, Zopf D, Steplewski Z, Koprowski H, Ginsburg V: A monoclonal antibody-defined antigen associated with gastrointestinal cancer is a ganglioside containing sialylated lacto-n-fucopentaose ii. J Biol Chem 1982; 257:14365-14369.
14 Charpin C, Bhan A K, Zurawski V R, Scully R E: Carcinoembryonic antigen (cea) and carbohydrate determinant 19-9 (ca 19-9) localization in 121 primary and metastatic ovarian tumors: An immunohistochemical study with the use of monoclonal antibodies. Int J Gynecol Pathol 1982; 1:231-245.
15 Yamada N, Chung Y S, Takatsuka S, Arimoto Y, Sawada T, Dohi T, Sowa M: Increased sialyl lewis a expression and fucosyltransferase activity with acquisition of a high metastatic capacity in a colon cancer cell line. Br J Cancer 1997; 76:582-587.
16 Nakagoe T, Sawai T, Tsuji T, Jibiki M, Nanashima A, Yamaguchi H, Kurosaki N, Yasutake T, Ayabe H: Circulating sialyl lewis(x), sialyl lewis(a), and sialyl to antigens in colorectal cancer patients: Multivariate analysis of predictive factors for serum antigen levels. J Gastroenterol 2001; 36:166-172.
17 Heimburg-Molinaro J, Lum M, Vijay G, Jain M, Almogren A, Rittenhouse-Olson K: Cancer vaccines and carbohydrate epitopes. Vaccine 2011; 29:8802-8826.
18 Durrant L G, Harding S J, Green N H, Buckberry L D, Parsons T: A new anticancer glycolipid monoclonal antibody, sc104, which directly induces tumor cell apoptosis. Cancer Res 2006; 66:5901-5909.
19 Watanabe M, Ohishi T, Kuzuoka M, Nudelman E D, Stroud M R, Kubota T, Kodairo S, Abe O, Hirohashi S, Shimosato Y: In vitro and in vivo antitumor effects of murine monoclonal antibody ncc-st-421 reacting with dimeric le(a) (le(a)/le(a)) epitope. Cancer Res 1991; 51:2199-2204.
20 Mårtensson S, Due C, Påhlsson P, Nilsson B, Eriksson H, Zopf D, Olsson L, Lundblad A: A carbohydrate epitope associated with human squamous lung cancer. Cancer Res 1988; 48:2125-2131.
21 Jewett A, Tseng H C: Tumor induced inactivation of natural killer cell cytotoxic function; implication in growth, expansion and differentiation of cancer stem cells. J Cancer 2011; 2:443-457.

22 D'Adamo P J, Kelly G S: Metabolic and immunologic consequences of abh secretor and lewis subtype status. Altern Med Rev 2001; 6:390-405.

23 Kim M J, Kim H S, Song K S, Noh S H, Kim H G, Paik Y K, Kim H O: Altered expression of lewis antigen on tissue and erythrocytes in gastric cancer patients. Yonsei Med J 2002; 43:427-434.

24 Akhter S, Kibria G, Akhter N, Habibullah M, Islam S, Zakariah M: Abo and lewis blood grouping with abh secretor and non-secretor status: A cross sectional study in dhaka. Faridpur Med Coll J 2011; 6:38-40.

25 Ward E S, Güssow D, Griffiths A D, Jones P T, Winter G: Binding activities of a repertoire of single immunoglobulin variable domains secreted from *escherichia coli*. Nature 1989; 341:544-546.

26 Bird R E, Hardman K D, Jacobson J W, Johnson S, Kaufman B M, Lee S M, Lee T, Pope S H, Riordan G S, Whitlow M: Single-chain antigen-binding proteins. Science 1988; 242:423-426.

27 Huston J S, Levinson D, Mudgett-Hunter M, Tai M S, Novotny J, Margolies M N, Ridge R J, Bruccoleri R E, Haber E, Crea R: Protein engineering of antibody binding sites: Recovery of specific activity in an anti-digoxin single-chain fv analogue produced in *escherichia coli*. Proc Natl Acad Sci USA 1988; 85:5879-5883.

28 Holliger P, Prospero T, Winter G: "Diabodies": Small bivalent and bispecific antibody fragments. Proc Natl Acad Sci USA 1993; 90:6444-6448.

29 Holliger P, Winter G: Engineering bispecific antibodies. Curr Opin Biotechnol 1993; 4:446-449.

30 Traunecker A, Lanzavecchia A, Karjalainen K: Bispecific single chain molecules (janusins) target cytotoxic lymphocytes on hiv infected cells. EMBO J 1991; 10:3655-3659.

31 Karlin S, Altschul S F: Methods for assessing the statistical significance of molecular sequence features by using general scoring schemes. Proc Natl Acad Sci USA 1990; 87:2264-2268.

32 Karlin S, Altschul S F: Applications and statistics for multiple high-scoring segments in molecular sequences. Proc Natl Acad Sci USA 1993; 90:5873-5877.

33 Altschul S F, Gish W, Miller W, Myers E W, Lipman D J: Basic local alignment search tool. J Mol Biol 1990; 215:403-410.

34 Altschul S F, Madden T L, Schaffer A A, Zhang J, Zhang Z, Miller W, Lipman D J: Gapped blast and psi-blast: A new generation of protein database search programs. Nucleic Acids Res 1997; 25:3389-3402.

35 Myers E W, Miller W: Approximate matching of regular expressions. Bull Math Biol 1989; 51:5-37.

36 Torelli A, Robotti C A: Advance and adam: Two algorithms for the analysis of global similarity between homologous informational sequences. Comput Appl Biosci 1994; 10:3-5.

37 Pearson W R, Lipman D J: Improved tools for biological sequence comparison. Proc Natl Acad Sci USA 1988; 85:2444-2448.

38 Marks J D, Griffiths A D, Malmqvist M, Clackson T P, Bye J M, Winter G: By-passing immunization: Building high affinity human antibodies by chain shuffling. Biotechnology (N Y) 1992; 10:779-783.

39 Stemmer W P: Rapid evolution of a protein in vitro by dna shuffling. Nature 1994; 370:389-391.

40 Gram H, Marconi L A, Barbas C F, Collet T A, Lerner R A, Kang A S: In vitro selection and affinity maturation of antibodies from a naive combinatorial immunoglobulin library. Proc Natl Acad Sci USA 1992; 89:3576-3580.

41 Barbas C F, Hu D, Dunlop N, Sawyer L, Cababa D, Hendry R M, Nara P L, Burton D R: In vitro evolution of a neutralizing human antibody to human immunodeficiency virus type 1 to enhance affinity and broaden strain cross-reactivity. Proc Natl Acad Sci USA 1994; 91:3809-3813.

42 Schier R, McCall A, Adams G P, Marshall K W, Merritt H, Yim M, Crawford R S, Weiner L M, Marks C, Marks J D: Isolation of picomolar affinity anti-c-erbb-2 single-chain fv by molecular evolution of the complementarity determining regions in the center of the antibody binding site. J Mol Biol 1996; 263:551-567.

43 Sidman K R, Steber W D, Schwope A D, Schnaper G R: Controlled release of macromolecules and pharmaceuticals from synthetic polypeptides based on glutamic acid. Biopolymers 1983; 22:547-556.

44 Langer R, Brem H, Tapper D: Biocompatibility of polymeric delivery systems for macromolecules. J Biomed Mater Res 1981; 15:267-277.

45 Remington R P: Remington's pharmaceutical sciences, ed 16th. Mack Pub. Co, 1980.

46 Stewart J MaY, J. D.: Solid phase peptide synthesis, ed 2nd. Rockford, Ill., Pierce Chemical Company, 1984.

47 Bodanzsky M, Bodanzsky, A.: The practice of peptide synthesis. New York, Springer Verlag, 1984.

48 Pluckthun A: Antibody engineering: Advances from the use of *escherichia coli* expression systems. Biotechnology (N Y) 1991; 9:545-551.

49 Reff M E: High-level production of recombinant immunoglobulins in mammalian cells. Curr Opin Biotechnol 1993; 4:573-576.

50 Trill J J, Shatzman A R, Ganguly S: Production of monoclonal antibodies in cos and cho cells. Curr Opin Biotechnol 1995; 6:553-560.

51 Sambrook J: Molecular cloning: A laboratory manual, ed 2nd. Cold Spring Harbor Laboratory Press, 1989.

52 Ausubel F M: Short protocols in molecular biology, ed 2nd. John Wiley & Sons, 1992.

53 Zhong L T, Manzi A, Skowronski E, Notterpek L, Fluharty A L, Faull K F, Masada I, Rabizadeh S, Varsanyi-Nagy M, Ruan Y, Oh J D, Butcher L L, Bredesen D E: A monoclonal antibody that induces neuronal apoptosis binds a metastasis marker. Cancer Res 2001; 61:5741-5748.

54 Zhang G, Zhang H, Wang Q, Lal P, Carroll A M, de la Llera-Moya M, Xu X, Greene M I: Suppression of human prostate tumor growth by a unique prostate-specific monoclonal antibody f77 targeting a glycolipid marker. Proc Natl Acad Sci USA 2010; 107:732-737.

55 Loo D, Pryer N, Young P, Liang T, Coberly S, King K L, Kang K, Roberts P, Tsao M, Xu X, Potts B, Mather J P: The glycotope-specific rav12 monoclonal antibody induces oncosis in vitro and has antitumor activity against gastrointestinal adenocarcinoma tumor xenografts in vivo. Mol Cancer Ther 2007; 6:856-865.

56 Alvarez-Rueda N, Leprieur S, Clémenceau B, Supiot S, Sébille-Rivain V, Faivre-Chauvet A, Davodeau F, Paris F, Barbet J, Aubry J, Birklé S: Binding activities and antitumor properties of a new mouse/human chimeric antibody specific for gd2 ganglioside antigen. Clin Cancer Res 2007; 13:5613s-5620s.

57 Hellström I, Garrigues H J, Garrigues U, Hellström K E: Highly tumor-reactive, internalizing, mouse monoclonal antibodies to le(y)-related cell surface antigens. Cancer Res 1990; 50:2183-2190.

58 Chou H H, Takematsu H, Diaz S, Iber J, Nickerson E, Wright K L, Muchmore E A, Nelson D L, Warren S T, Varki A: A mutation in human cmp-sialic acid hydroxylase occurred after the homo-pan divergence. Proc Natl Acad Sci USA 1998; 95:11751-11756.
59 Lefranc M P, Giudicelli V, Ginestoux C, Jabado-Michaloud J, Folch G, Bellahcene F, Wu Y, Gemrot E, Brochet X, Lane J, Regnier L, Ehrenmann F, Lefranc G, Duroux P: Imgt, the international immunogenetics information system. Nucleic Acids Res 2009; 37:D1006-1012.
60 Jones S T, Bendig M M: Rapid per-cloning of full-length mouse immunoglobulin variable regions. Biotechnology (N Y) 1991; 9:88-89.
61 Sambrook J, Russell D W: Molecular cloning: A laboratory manual, ed 3rd. Cold Spring Harbor, N.Y., Cold Spring Harbor Laboratory Press, 2001.

PATENT REFERENCES

WO 2005/108430
EP-A-184187
GB 2188638A
EP-A-239400
EP-A-0120694
EP-A-0125023
U.S. Pat. No. 5,225,539
U.S. Pat. No. 4,816,567
US 92/09965
WO 94/13804
WO 92/01047
EP-A-0058481
EP-A-0052522
EP-A-0036676
EP-A-0088046
EP-A-0143949
EP-A-0142541
JP-A-83-11808
U.S. Pat. No. 4,485,045
U.S. Pat. No. 4,544,545

The invention claimed is:

1. An isolated antibody capable of binding galβ1-3GlcNacβ1-3Galβ1-4(Fucα1-3)GlcNAc, wherein the isolated antibody comprises binding domains comprising the amino acid sequence of residues 27 to 38 (CDRH1), 56-65 (CDRH2) and 105 to 121 (CDRH3) of FIG. 1a or 2a; and binding domains comprising the amino acid sequence of residues 27 to 38 (CDRL1), 56-65 (CDRL2) and 105 to 121 (CDRL3) of FIG. 1b or 2b.

2. The isolated antibody of claim 1, further capable of binding glycans containing:

galβ1-3(Fucα1-4)GlcNAcβ1-3Galβ1-4(Fucα1-3)GlcNAc, galβ1-3(Fucα1-4)GlcNAcβ1-3Galβ1-3(Fucα1-4)GlcNAc, Galβ1-4(Fucα1-3)GlcNAc; or
Galβ1-3(Fucα1-4)GlcNAc, and directly inducing cell death without the need for immune effector cells.

3. The isolated antibody of claim 1, comprising a binding domain and wherein the binding domain comprises the amino acid sequence of residues 105 to 121 (CDRH3) of FIG. 1a or 2a.

4. The isolated antibody of claim 1, comprising a human antibody framework.

5. The isolated antibody of claim 1, comprising the amino acid sequence of residues 1 to 133 (VH) of FIG. 1a or 2a.

6. The isolated antibody of claim 1, comprising a human antibody constant region.

7. The isolated antibody of claim 1, comprising the amino acid sequence of residues 1 to 123 (VL) of FIG. 1b or 2b.

8. The isolated antibody of claim 1, wherein the binding member is an antibody is an antibody fragment, Fab, (Fab')$_2$, scFv, Fv, dAb, Fd or a diabody.

9. The isolated antibody of claim 1, wherein the antibody is a polyclonal or monoclonal antibody.

10. The isolated antibody of claim 1, wherein the antibody is a humanised, chimeric or veneered antibody.

11. A pharmaceutical composition comprising the isolated antibody capable of binding galβ1-3 GLcNacβ1-3 Galβ1-4(Fucα1-3)GlcNAc of claim 1 and a pharmaceutically acceptable excipient, diluent, carrier, buffer or stabiliser.

12. An isolated antibody comprising residues 1 to 133 (VH) of the amino acid sequence of FIG. 1a or 2a, and residues 1 to 123 (VL) of the amino acid sequence of FIG. 1b or 2b.

13. The isolated antibody of claim 12, further comprising a human constant region.

14. An isolated antibody capable of binding 3GlcNacβ1-3Galβ1-4(Fucα1-3)GlcNAc, which competes for binding to glycans containing:
galβ1-3GLcNacβ1-3Galβ1-4(Fucα1-3)GlcNAc
galβ1-3(Fucα1-4)GlcNAcβ1-3Galβ1-4(Fucα1-3)GlcNAc,
galβ1-3(Fucα1-4)GlcNAcβ1-3Galβ1-3(Fucα1-4)GlcNAc,
Galβ1-4(Fucα1-3)GlcNAc; or
Galβ1-3(Fucα1-4)GlcNAc
with an antibody comprising a VH chain having the amino acid sequence of residues 1 to 133 of FIG. 1a or 2a and a VL chain having the amino acid sequence of residues 1 to 123 of FIG. 1b or 2b.

15. The binding member of claim 1, An isolated antibody which competes for binding to 3GlcNacβ1-3Galβ1-4(Fucα1-3)GlcNAc with an antibody comprising a VH chain having the amino acid sequence of residues 1 to 133 of FIG. 1a or 2a and a VL chain having the amino acid sequence of residues 1 to 123 of FIG. 1b or 2b.

16. An isolated antibody which competes for binding to glycans containing:
galβ1-3GLcNacβ1-3Galβ1-4(Fucα1-3)GlcNAc
galβ1-3(Fucα1-4)GlcNAcβ1-3Galβ1-4(Fucα1-3)GlcNAc,
galβ1-3(Fucα1-4)GlcNAcβ1-3Galβ1-3(Fucα1-4)GlcNAc,
Galβ1-4(Fucα1-3)GlcNAc; or
Galβ1-3(Fucα1-4)GlcNAc
with an antibody comprising a VH chain having the amino acid sequence of residues 1 to 133 of FIG. 1a and a VL chain having the amino acid sequence of residues 1 to 123 of FIG. 1b, or with an antibody comprising a VH chain having the amino acid sequence of residues 1 to 133 of FIG. 2a and a VL chain having the amino acid sequence of residues 1 to 123 of FIG. 2b.

* * * * *